(12) United States Patent
Jacobson et al.

(10) Patent No.: US 9,821,169 B2
(45) Date of Patent: *Nov. 21, 2017

(54) SYSTEMS AND METHODS FOR PROVIDING A MAGNETIC RESONANCE TREATMENT TO A SUBJECT

(71) Applicant: Applied Magnetics, LLC, Clearwater, FL (US)

(72) Inventors: Jerry Jacobson, Jupiter, FL (US); Allen Braswell, Clearwater, FL (US)

(73) Assignee: Applied Magnetics, LLC, Littleton, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,542

(22) Filed: Jun. 26, 2017

(65) Prior Publication Data

US 2017/0291039 A1    Oct. 12, 2017

Related U.S. Application Data

(63) Continuation of application No. 12/546,385, filed on Aug. 24, 2009, now Pat. No. 9,724,534.
(Continued)

(51) Int. Cl.
*G06F 15/18*    (2006.01)
*A61N 2/02*    (2006.01)
(Continued)

(52) U.S. Cl.
CPC .............. *A61N 2/02* (2013.01); *A61B 5/4836* (2013.01); *G06F 19/3481* (2013.01); *A61B 5/01* (2013.01);
(Continued)

(58) Field of Classification Search
None
See application file for complete search history.

(56) References Cited

U.S. PATENT DOCUMENTS

| 781,448 A | 1/1905 | McIntyre |
| 2,099,511 A | 1/1934 | Caesar |

(Continued)

FOREIGN PATENT DOCUMENTS

| AU | B-45680/89 | 6/1990 |
| CN | 2822512 Y | 10/2006 |

(Continued)

OTHER PUBLICATIONS

European Patent Office Application No. 09791851.0, Summons to Oral Proceedings dated May 22, 2015.
(Continued)

*Primary Examiner* — Paulinho E Smith
(74) *Attorney, Agent, or Firm* — Kilpatrick Townsend & Stockton LLP

(57) ABSTRACT

Disclosed here in are a system and method for providing a magnetic resonance treatment to a subject. In one described embodiment, a system for providing a magnetic resonance treatment to a subject is provided, the system including components that provide the system with an ability to treat pain and relieve symptoms of the subject. In another embodiment, a method of providing a magnetic resonance treatment to a subject is provided, wherein the system includes components that provide the system with an ability to treat pain, relieve symptoms, provide relaxation, and improve the overall comfort and well-being of the subject.

20 Claims, 24 Drawing Sheets

Related U.S. Application Data

(60) Provisional application No. 61/091,582, filed on Aug. 25, 2008.

(51) Int. Cl.
*A61B 5/00* (2006.01)
*G06F 19/00* (2011.01)
*A61B 5/0205* (2006.01)
*A61B 5/021* (2006.01)
*A61B 5/01* (2006.01)
*A61B 5/0402* (2006.01)
*A61B 5/0476* (2006.01)

(52) U.S. Cl.
CPC ............ *A61B 5/021* (2013.01); *A61B 5/0205* (2013.01); *A61B 5/02055* (2013.01); *A61B 5/0402* (2013.01); *A61B 5/0476* (2013.01); *A61B 5/4266* (2013.01); *A61B 5/6806* (2013.01)

(56) References Cited

U.S. PATENT DOCUMENTS

| | | | |
|---|---|---|---|
| 2,103,440 A | 4/1934 | Weissenberg | |
| 3,659,282 A | 4/1972 | Tada | |
| 3,738,369 A | 6/1973 | Adams et al. | |
| 3,890,953 A | 6/1975 | Kraus et al. | |
| 3,967,215 A | 6/1976 | Bellak | |
| 4,047,068 A | 9/1977 | Ress et al. | |
| 4,271,392 A | 6/1981 | Outram et al. | |
| 4,323,056 A | 4/1982 | Borrelli et al. | |
| 4,524,079 A | 6/1985 | Hofmann | |
| 4,576,172 A | 3/1986 | Bentall | |
| 4,611,599 A | 9/1986 | Bentall et al. | |
| 4,674,481 A | 6/1987 | Boddie et al. | |
| 4,723,536 A | 2/1988 | Rauscher et al. | |
| 4,889,526 A | 12/1989 | Rauscher et al. | |
| 5,019,076 A | 5/1991 | Yamanashi | |
| 5,088,976 A | 2/1992 | Liboff et al. | |
| 5,170,784 A | 12/1992 | Ramon et al. | |
| 5,198,181 A | 3/1993 | Jacobson | |
| 5,214,383 A * | 5/1993 | Perlmutter | G01R 33/24 324/300 |
| 5,269,746 A | 12/1993 | Jacobson | |
| 5,366,435 A | 11/1994 | Jacobson | |
| 5,453,072 A | 9/1995 | Anninos et al. | |
| 5,470,846 A | 11/1995 | Sandyk | |
| 5,496,258 A | 3/1996 | Anninos et al. | |
| 5,691,324 A | 11/1997 | Sandyk | |
| 5,691,325 A | 11/1997 | Sandyk | |
| 5,697,883 A | 12/1997 | Anninos et al. | |
| 5,733,247 A * | 3/1998 | Fallon | A61B 5/0017 324/309 |
| 5,885,976 A | 3/1999 | Sandyk | |
| 5,964,759 A | 10/1999 | Yamanashi | |
| 6,004,257 A | 12/1999 | Jacobson | |
| 6,022,479 A | 2/2000 | Smirnov | |
| 6,059,781 A | 5/2000 | Yamanashi | |
| 6,099,459 A * | 8/2000 | Jacobson | A61N 2/02 128/897 |
| 6,154,031 A * | 11/2000 | Hughes | G01R 33/3852 324/318 |
| 6,155,968 A | 12/2000 | Parker | |
| 6,280,376 B1 | 8/2001 | Holcomb | |
| 6,287,614 B1 | 9/2001 | Peiffer | |
| 6,301,506 B1 | 10/2001 | Den Boer et al. | |
| 6,458,071 B1 | 10/2002 | Jacobson | |
| 6,466,813 B1 * | 10/2002 | Shukla | A61B 5/055 382/128 |
| 6,476,607 B1 * | 11/2002 | Dannels | G01R 33/4824 324/307 |
| 6,488,617 B1 | 12/2002 | Katz | |
| 6,494,370 B1 | 12/2002 | Sanchez | |
| 6,523,009 B1 * | 2/2003 | Wilkins | G06Q 30/06 705/2 |
| 6,527,697 B2 | 3/2003 | Bashford | |
| 6,579,375 B2 | 6/2003 | Beckett et al. | |
| 6,733,434 B2 | 5/2004 | Jacobson | |
| 6,804,558 B2 | 10/2004 | Haller | |
| 6,842,645 B2 | 1/2005 | Dalal | |
| 6,858,000 B1 | 2/2005 | Schukin et al. | |
| 6,917,833 B2 | 7/2005 | Denker et al. | |
| 6,995,700 B2 | 2/2006 | Roger et al. | |
| 7,186,209 B2 | 3/2007 | Jacobson et al. | |
| 7,324,850 B2 | 1/2008 | Persen | |
| 7,395,117 B2 | 7/2008 | Mazar | |
| 8,049,504 B2 | 11/2011 | Findeklee | |
| 2001/0010732 A1 * | 8/2001 | Oosawa | G06T 3/0081 382/128 |
| 2001/0019264 A1 * | 9/2001 | Shattil | H05K 9/00 324/225 |
| 2001/0049609 A1 * | 12/2001 | Girouard | G06F 19/3481 705/3 |
| 2002/0026228 A1 | 2/2002 | Schauerte | |
| 2002/0087859 A1 * | 7/2002 | Weeks | G06F 21/604 713/156 |
| 2002/0161664 A1 * | 10/2002 | Shaya | G06Q 30/02 705/26.1 |
| 2003/0031992 A1 * | 2/2003 | Laferriere | G09B 23/28 434/262 |
| 2004/0136489 A1 | 7/2004 | Takahashi et al. | |
| 2004/0181115 A1 | 9/2004 | Sandyk et al. | |
| 2004/0189301 A1 | 9/2004 | Biglieri et al. | |
| 2005/0080459 A1 | 4/2005 | Jacobson et al. | |
| 2005/0222625 A1 | 10/2005 | Laniado et al. | |
| 2005/0283330 A1 | 12/2005 | Laraia et al. | |
| 2007/0004957 A1 | 1/2007 | Hilburg | |
| 2009/0094063 A1 | 4/2009 | Ennett | |
| 2010/0010288 A1 | 1/2010 | Von Ohlsen et al. | |
| 2010/0057655 A1 | 3/2010 | Jacobson et al. | |
| 2010/0072996 A1 | 3/2010 | Jacobson et al. | |
| 2010/0241012 A1 | 9/2010 | Yin et al. | |

FOREIGN PATENT DOCUMENTS

| | | | |
|---|---|---|---|
| DE | 10157024 | 5/2003 | |
| EP | 0454298 A2 | 10/1991 | |
| EP | 37 1 504 | 1/1997 | |
| GR | 1003262 | 11/1999 | |
| WO | WO 1991/06341 | 5/1991 | |
| WO | WO 1992/03185 | 3/1992 | |
| WO | WO 1995/31939 | 11/1995 | |
| WO | WO 1997/46244 | 12/1997 | |
| WO | WO 1999/13884 | 3/1999 | |
| WO | WO 2000/13749 | 3/2000 | |
| WO | WO 2001/15775 | 3/2001 | |
| WO | WO 2001/26548 | 4/2001 | |
| WO | WO 2003/17061 A2 | 2/2003 | |
| WO | WO 2003/060750 | 7/2003 | |
| WO | WO 2007/051419 | 3/2006 | |
| WO | WO 2008/053482 A2 | 5/2008 | |
| WO | WO 2010025114 A1 * | 3/2010 | A61N 2/02 |

OTHER PUBLICATIONS

European Patent Office Application No. 09791851.0, Communication Pursuant to Article 94(3) EPC dated May 13, 2014.
European Patent Office Application No. 09791851.0, Communication Pursuant to Article 94(3) EPC dated Sep. 25, 2013.
European Patent Office Application No. 09791851.0, Communication Pursuant to Article 94(3) EPC dated Apr. 25, 2013.
European Patent Office Application No. 09791851.0, Communication Pursuant to Article 94(3) EPC dated Sep. 12, 2012.
European Patent Office Application No. 09791851.0, Communication Pursuant to Article 94(3) EPC dated Apr. 23, 2012.
International Preliminary Report on Patentability dated Mar. 10, 2011 for corresponding International Application No. PCT/US2009/054803.

(56) References Cited

OTHER PUBLICATIONS

International Search Report and Written Opinion dated Nov. 5, 2009 for corresponding International Application No. PCT/US2009/054803.
International Preliminary Report on Patentability dated Mar. 10, 2011 for corresponding International Application No. PCT/US2009/055183.
International Search Report and Written Opinion dated Nov. 5, 2009 for corresponding International Application No. PCT/US2009/055183.
International Preliminary Report on Patentability dated Jan. 20, 2011 for corresponding International Application No. PCT/US2009/050114.
International Search Report and Written Opinion dated Nov. 6, 2009 for corresponding International Application No. PCT/US2009/050114.
The State Intellectual Property Office of the People's Republic of China, Application No. 200980141414.3, Office Action dated Mar. 12, 2016.
The State Intellectual Property Office of the People's Republic of China, Application No. 200980141414.3, Office Action dated Aug. 26, 2015.
The State Intellectual Property Office of the People's Republic of China, Application No. 200980141414.3, Office Action dated Apr. 21, 2014.
The State Intellectual Property Office of the People's Republic of China, Application No. 200980141414.3, Office Action dated Nov. 11, 2013.
The State Intellectual Property Office of the People's Republic of China, Application No. 200980141414.3, Office Action dated Jun. 4, 2013.
Adey, W.R., "Physiological Signaling Across Cell Membranes and Cooperative Influences of Extremely Low Frequency Electromagnetic Fields," *Biological Coherence and Response to External Stimuli*, Herbert Frohlich Ed., Springer-Verlag, 1988, 148-170.
Adey, W.R., "Tissue Interactions with Nonionizing Electromagnetic Fields," *Physiological Reviews*, 1981, 61(2): 435-514.
Anninos, P.A. et al., "The Biological Effects of Magnetic Stimulation in Epileptic Patients," *Panminerva Medica*, 1999, 41(3): 207-215.
Anninos, P.A. et al., "Magnetic Stimulation in the Treatment of Partial Seizures," *Intern. J. Neuroscience*, 1991, 60: 141-175.
Beall, P.T. et al., "Distinction of Normal, Preneoplastic, and Neoplastic Mouse Mammary Primary Cell Cultures by Water Nuclear Magnetic Resonance Relaxation Times," *JNCI.*, 1980, 64(2): 335-338.
Bistolfi, F., "Biostructures and Radiation Order Disorder," *Edizioni Minerva Medica, Corso Bramante 83/85-Torino*, 1991, 61-92, 261.
Cheng, D.K., *Field and Wave Electromagnetics*, Addison Wesley Publishing Company, 1983, 255-261, 569-576.
Clegg, J.S., "Intracellular Water and the Cytomatrix: Some Methods of Study and Current Views," *The Journal of Cell Biology*, 1984, 99(1): 167-171.
Clegg, J.S., "Intracellular Water, Metabolism and Cell Architecture; Part 2," *Coherent Excitations in Biological Systems*, Herbert Frohlich Ed., Springer-Verlag, 1983, 162-177.
Clegg, J.S., "Properties and Metabolism of the Aqueous Cytoplasm and Its Boundaries," *The American Physiological Society*, 1984, R133-R151.
Cohen, D., "Magnetoencephalography: Detection of the Brain's Electrical Activity with a Superconducting Magnetometer," *Science*, 1971, 175: 664-666.
Cremer-Bartels, G., "Influence of Low Magnetic-Field-Strength Variations on the Retina and Pineal Gland of Quail and Humans," *Graefe's Archive Ophthalmology*, 1983, 220: 248-252.
Egan, T.F. et al., "Molecular Basis of Contrast in MRI," *Cell Function and Disease*, Candeo et al, (eds), Plenum Press, New York and London, 1988, 405-413.

Eichhorn, G.L., "Aging, Genetics and the Environment: Potential Errors Introduced Into Genetic Information Transfer by Metal Ions," *Mechanisms of Ageing and Developments*, 1979, 9: 291-301.
Hazlewood, C.F., "Implications of Cellular Water in Health and Disease," Second Annual Advanced Water Sciences Symposium, Dallas, TX, Oct. 4-6, 1996, 1-5.
Hazlewood, C.F., "A Role for Water in the Exclusion of Cellular Sodium—Is a Sodium Pump Needed?" *Cardiovascular Diseases, Bulletin of the Texas Heart Institute*, 1975, 2(1): 83-104.
Hazlewood, C.F., "A View of the Significance and Understanding of the Physical Properties of Cell-Associated Water," Cell-Associated Water, Academic Press, Inc., 1979, 165-259.
Hazlewood, C.F., "Diffusion of Water in Tissues and MRI," *Magnetic Resonance in Medicine*, 1991, 19: 214-216.
IEEE "IEEE Xplore 2.0 User Guide", Nov. 11, 2006, via the web http://ieeexplore.ieee.org/otherfiles/x20_guide_full.pdf, pp. 1-76.
Jacobson, J.I., "Jacobson Resonance: The Quantum-Mechanical Basis for a Novel Radiological Approach to Treating Cancer and AIDS," Frontier Perspectives, Fall/Winter 1996, 6(1):17-26.
Jacobson, J. I. and Yamanashi, W. S., "A Possible, Physical Mechanism in the Treatment of Neurologic Disorders with Externally Applied Pico Tesla Magnetic Fields," Physiol. Chem. Phys & Med. NMR, 1994 26:287-297.
Jacobson, J.I., "Jacobson Resonance: The Coupling Mechanism for Weak Electromagnetic Field Bioeffects, and a New Way to Approach Magneto Therapy," *Panminerva Medica*, 1994, 36(1): 34-41.
Jacobson, J.I., "Exploring the Potential of Magneto-Recrystallization of Genes and Associated Structures with Respect to Nerve Regeneration and Cancer," *Int. Journal of Neuroscience*, 1992, 64(1-4): 153-165.
Jacobson, J.I., "Is the Fusion Process the Basis for Growth, Repair, and Aging?" *Panminerva Medica*, 1990, 32(3): 132-140.
Jacobson, J.I. et al., "Pico Tesla Range Magnetic Fields Tested in Four Site, Double Blind Clinical Study for Treatment of Osteoarthritic Knees," *Gazzetta Medica Italiana-Arch. Sci. Med.*, 2001, 160: 1-21.
Jacobson, J.I., "Jacobson Resonance: The Quantum-mechanical Basis for a Novel Radiological Approach to Treating Cancer and AIDS," *Frontier Perspectives*, 1996, 6(1): 17-26.
Jacobson, J.I., "Jacobson Resonance is the Basis From Which to Evaluate Potential Hazard and Therapeutic Benefit from Extrinsic Magnetic Fields," *Panminerva Medica*, 1993, 35(3): 138-148.
Jacobson, J.I. "A Look at the Possible Mechanism and Potential of Magneto Therapy," *Journal of Theoretical Biology*, 1991, 149(1): 97-119.
Jacobson, J.I., "Physics in Medicine: A Potential Unfolding in the Radiological Sciences," *Panminerva Medica*, 1996, 39(2): 111-127.
Jacobson, J.I., "Pineal-Hypothalamic Tract Mediation of Picotesla Magnetic Fields in the Treatment of Neurological Disorders," *Panminerva Medica*, 1994, 36(4): 201-205.
Jacobson, J.I., "A Theoretical Look at Gravity in the Human Cell: Its Role in Normal Cell Division as Well as Neoplasia," *Panminerva Medica*, 1992, 34(3): 96-106.
Jacobson, J.I. et al., "A Possible, Physical Mechanism in the Treatment of Neurologic Disorders with Externally Applied Pico Tesla Magnetic Fields," *Physiol. Chem. Phys. & Med. NMR*, 1994, 26: 287-297.
"Jacobson Resonance Enterprises, Inc. Announces Research Findings in Breast Cancer Cells from the College of Veterinary Medicine at Mississippi State University," press release Apr. 30, 2004.
Kasturi, S.R., "Study of Anisotropy Nuclear Magnetic Resonance Relaxation Times of Water Protons in Skeletal Muscle," *Biophys. J.*, 1980, 30: 369-381.
Kasturi, S.R., "The Nature and Origin of Chemical Shift for Intracellular Water Nuclei in Artemia Cysts," *Biophys. J.*, 1987, 52: 249-256.
Kasturi, S.R., "Intracellular Water in Artemia Cysts (Brine Shrimp) Investigations by Deuterium and Oxygen-17 Nuclear Magnetic Resonance," *Biophys. J.*, 1990, 58: 483-491.
Lawrence, A.F. et al., "Nonlinear Wave Mechanisms in Interactions between Excitable Tissue and Electromagnetic Fields," *Neurological Research*, 1982, 4(1-2): 115-153.

(56) References Cited

OTHER PUBLICATIONS

Mikesell, N.D., "Structured Water: Its Healing Effects on the Diseased State," web-page at http://www.naturesalternatives.com/lc/mikesell.html as created on the internet Feb. 27, 1999.

"Oklahoma University researchers report dramatic growth effects of bean sprouts using Jacobson resonance," presented to the Indian Medical Association, Calcutta, India, 2002.

Qin, C. et al., "Effects on Rats of Low Intensity and Frequency Electromagnetic Field Stimulation on Thoracic Spinal Neurons Receiving Noxious Cardiac and Esophageal Inputs," Neuromodulation, 8(2): 79-87.

Reuss, S., "Different Types of Magnetically Sensitive Cells in the Rat Pineal Gland," *Neuroscience Letters*, 1983, 40: 23-26.

Rorschach, H.E. et al., "Diffusion of Water in Biological Tissues," *Scanning Microscopy Supplement*, 1991, 5: S1-S9.

Sandyk, R., "Alzheimer's Disease: Improvement of Visual Memory and Visuoconstructive Performance by Treatment with PicoTesla Range Magnetic Fields," *Intern. J. Neuroscience*, 1994, 76: 185-225.

Sandyk, R., "Clinical Case Report: Magnetic Fields in the Treatment of Parkinson's Disease," *Intern. J. Neuroscience*, 1992, 63: 141-150.

Sandyk, R., "Clinical Case Report: Successful Treatment of Multiple Sclerosis with Magnetic Fields," *Intern. J. Neuroscience*, 1992, 66: 237-250.

Saxena, A. et al, "Hypothetical Mathematical Construct Explaining the Mechanism of Biological Amplification in an Experimental Model Utilizing PicoTesla (PT) Electromagnetic Fields," *Medical Hypotheses*, 2003, 60(6): 821-839.

Scherlag, B.J. et al., "The Application of Low-Level Electromagnetic Fields to the Autonomic Nerve Inputs to the Heart: Effects on Heart Rate and Atrioventricular Conduction," abstract presented at annual meeting of the American Institute of Stress, in Hawaii, 2000.

Scherlag, B.J. et al., "Magnetism and Cardiac Arrhythmias," *Cardiology in Review*, 2004, 12(2): 85-96.

Scherlag, B.J. et al., "Use of Low-Level Electromagnetic Fields and Vago-Sympathetic Stimulation to Detect and Induce the Paroxysmal Atrial Fibrillation Syndrome," abstract presented at annual meeting of the American Institute of Stress, in Hawaii, 2000.

Schmidt et al.; "Case-Based Reasoning for Antibiotics Therapy Advice", 1999; Lecture Notes in Computer Science, vol. 1650/1999, pp. 550-560.

Seitz, P.K. et al., "Proton Magnetic Resonance Studies on the Physical State of Water in Artemia Cysts," *The Brine Shrimp Artemia*, 1980, 2: 545-554.

Trostel, C.T., DVM, et al., "Effects of Pico-Tesla Electromagnetic Field Treatment on Wound Healing in Rats," *Am.J.Veterinary Res.*, 2003, 64(7): 845-854.

Wangsness, R.K., *Electromagnetic Fields*, John Wiley & Sons, Chapter 14, 1986, 225-236.

Welker, H.A., "Effects of an Artificial Magnetic Field on Serotonin N-Acetyltransferase Activity and Melatonin Content of the Rat Pineal Gland," *Exp. Brain. Res.*, 1983, 50: 426-432.

Yamanashi, W. et al., "The Effect of Low-Level Electromagnetic Fields on a Simple Model of Osmosis, in Vitro," abstract presented at annual meeting of the American Institute of Stress, in Hawaii, 2000.

Zotev et al.; "Microtesla MRI of the Human Brain Combined with MEG"; Jun. 21, 2008; Journal of Magnetic Resonance; pp. 115-120.

* cited by examiner

Method 145

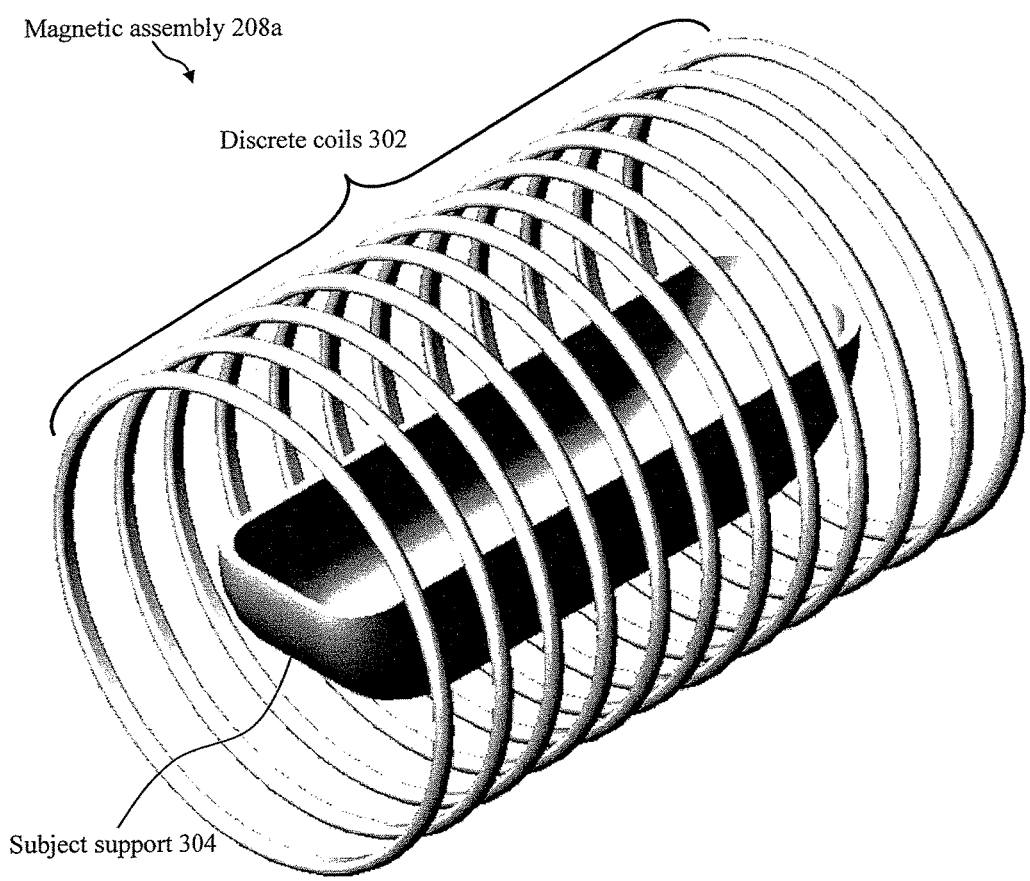

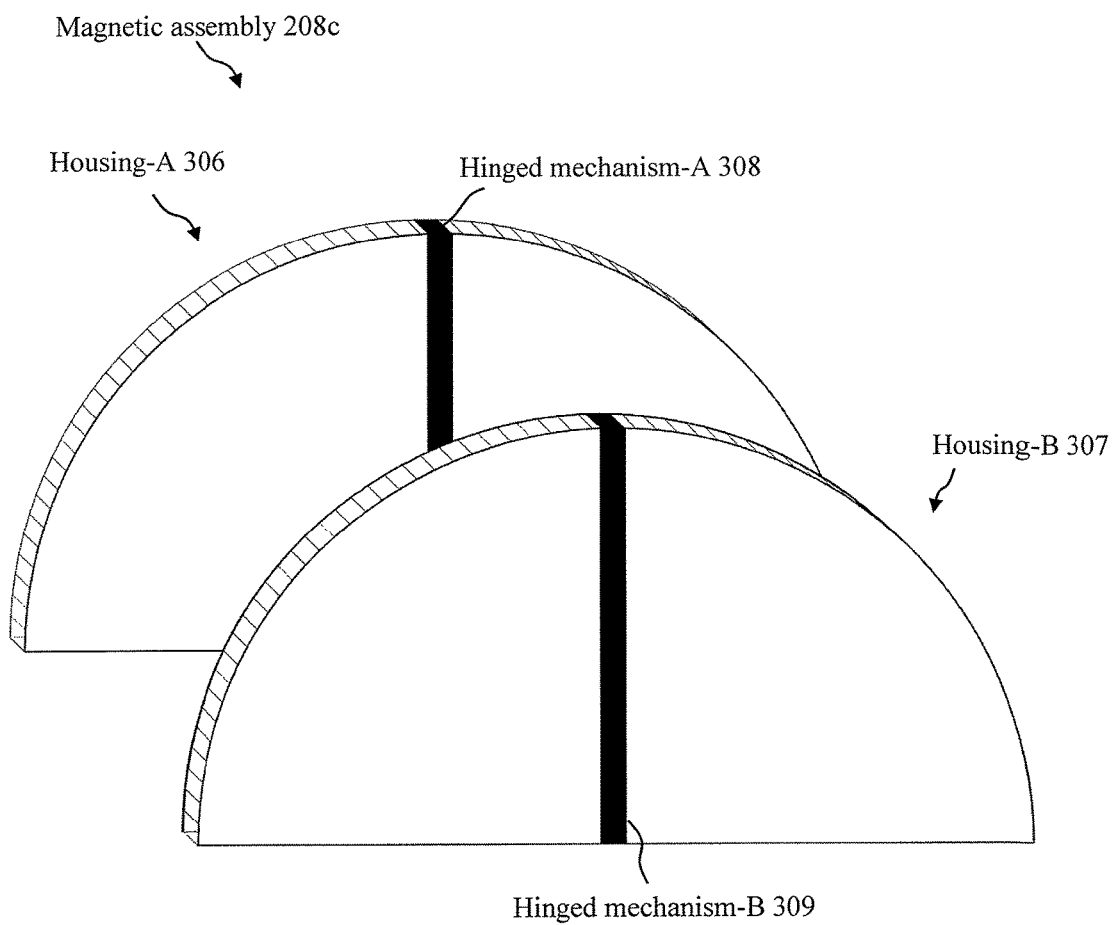

Magnetic assembly 208f

Magnetic assembly 208g

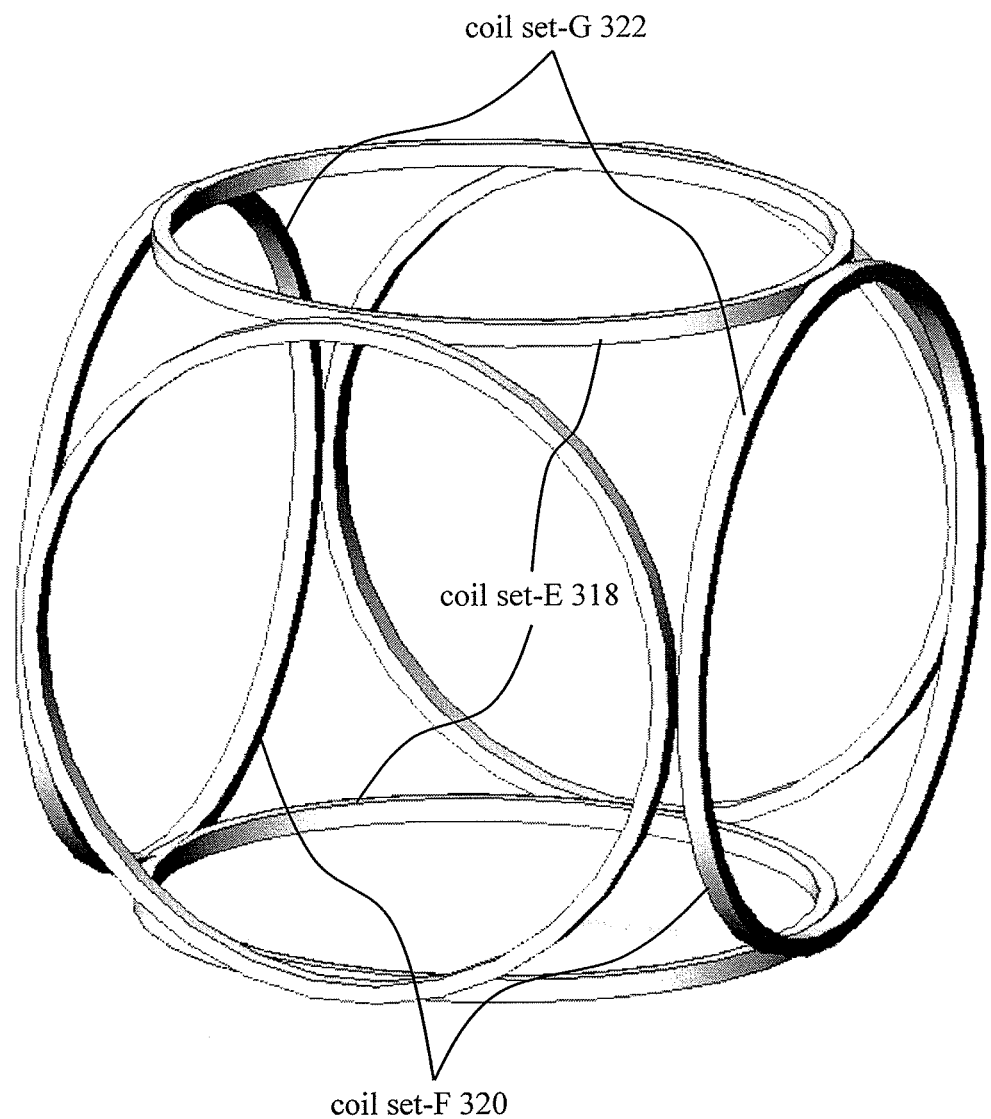

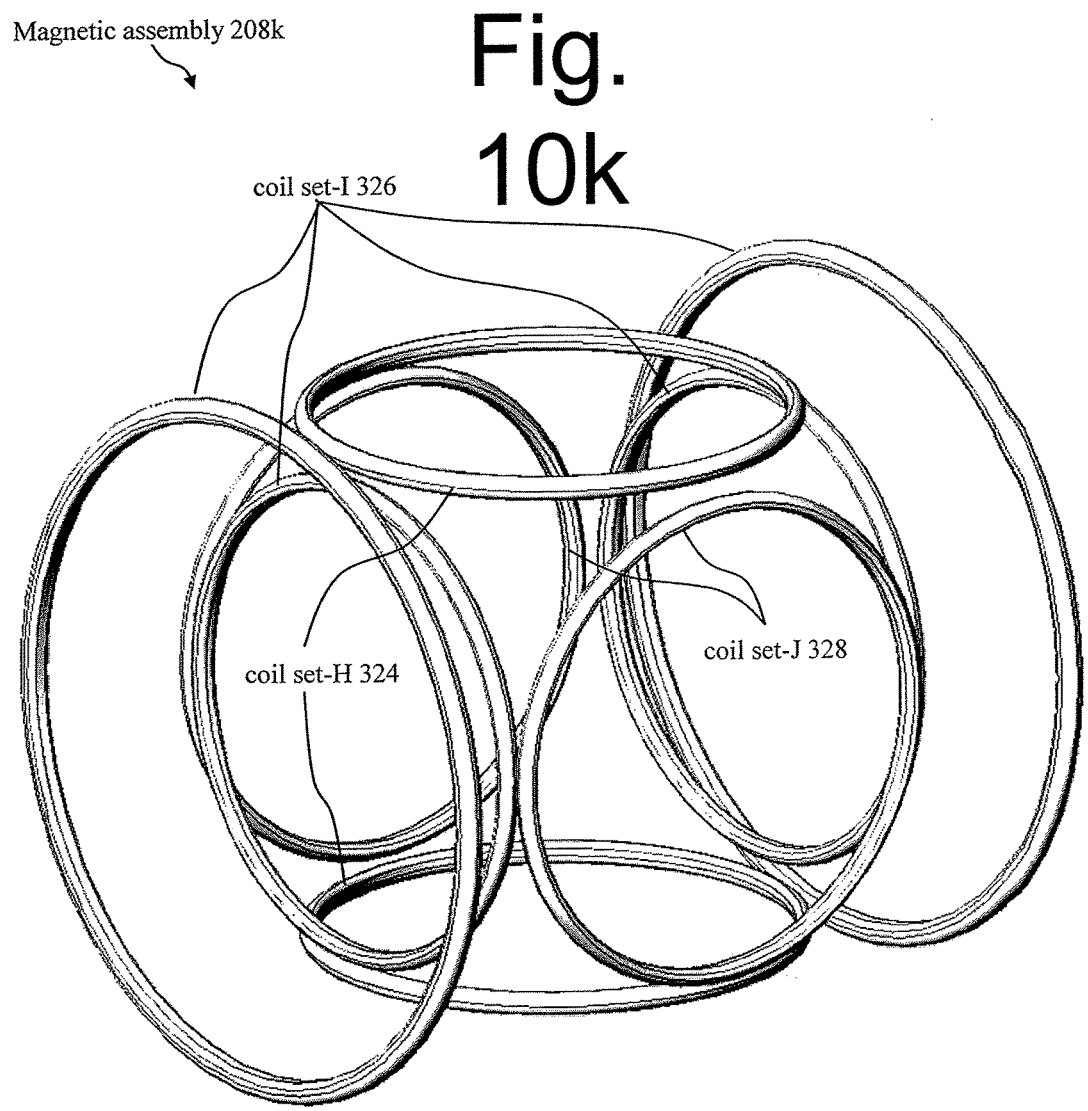

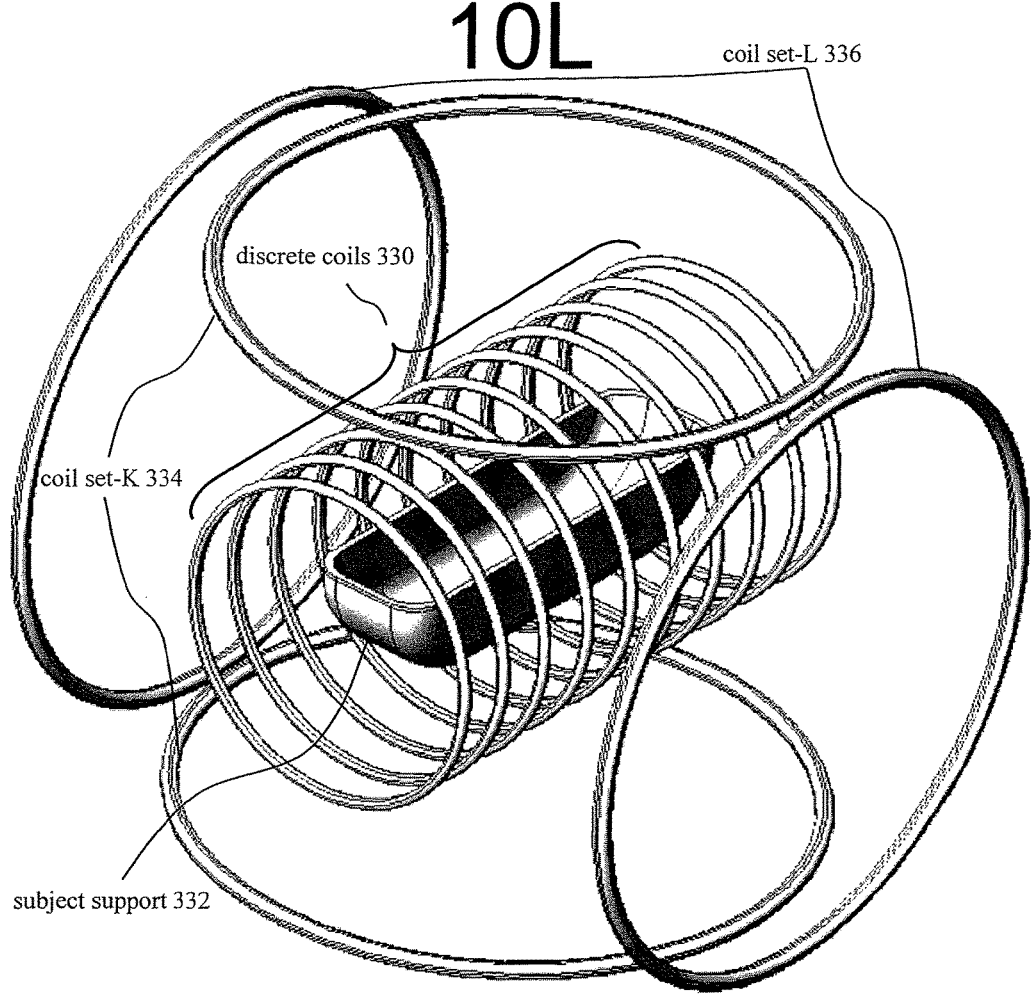

SYSTEMS AND METHODS FOR PROVIDING A MAGNETIC RESONANCE TREATMENT TO A SUBJECT

CROSS-REFERENCE TO RELATED APPLICATION

This application is a continuation of and claims priority to U.S. patent application Ser. No. 12/546,385, filed on Aug. 24, 2009, and entitled "Systems And Methods For Providing A Magnetic Resonance Treatment To A Subject," which claims priority to U.S. Provisional Patent Application Ser. No. 61/091,582, for "Systems and Methods for Providing a Magnetic Therapy Treatment to a Subject," filed on Aug. 25, 2008, the entirety of both of which is hereby incorporated herein by reference.

FIELD OF THE INVENTION

The present invention relates to systems and methods for providing magnetic resonance to a subject. In particular, this invention relates to a magnetic resonance treatment system and methods for using a system to treat pain, relieve symptoms, provide relaxation, and improve the overall comfort and well-being of the subject.

BACKGROUND

Magnetic resonance (MR) is a widely practiced and growing alternative treatment for many indications (i.e., illness, disease, medical condition, or ailment). Magnetic resonance devices have been known to be a natural and economical means of treating body pains and common injuries. Many methods have been used to apply magnets to comfort or heal body areas and thereby, avoiding the use of injections, pills, salves, or body-invasive procedures. Overall, the basis of magnetic resonance involves artificially produced fields. These fields interact with components such as, but not limited to, atomic or molecular components of living tissue, which then have a beneficial effect on that living tissue.

One form of magnetic resonance uses static magnetic fields. Static magnetic fields may be produced by permanent magnets incorporated into items such as bracelets, belts, back pads, mattress pads, and mattresses. It is believed that static magnetic fields have some efficacy in the treatment of broken bones and soft tissue injuries and tend to promote the circulation of blood as well as relieve stiffness in muscles.

More recent attempts to employ the therapeutic effects of magnetic fields have focused on devices that generate an electromagnetic field and the methods of treatment employing such devices in conjunction with computers. Various devices have been made to create time-varying magnetic fields for use on the human body. Specifically, in this time-varying magnetic field device are pulsed electromagnetic fields (PEMFs) which are generated when a current is forced to move through a conductor in discrete impulses of electric charge moving in the same direction. These devices have been used to treat pain and relieve symptoms, as disclosed, for example, in Jacobson, et al., in U.S. Pat. No. 5,269,746.

The ability of PEMFs to affect changes in the body is dependant on the ability of PEMFs to positively affect human physiologic or anatomic systems. The pulsed magnetic waves use low power electromagnetic fields that stimulate the cells in the body to trigger healing. One implementation of PEMFs involves selecting field strengths and frequencies that resonate with the cellular frequencies in the body. Recent research has found improved efficacy when very low PEMFs are tuned precisely to the indication or condition of the subject. Thus, there exists a need to enable this type of PEMF delivery to subjects.

Currently, medical practitioners and medical researchers worldwide, generalists or specialists, treat a broad range of diseases through the use of conventional medicine. With the use of magnetic resonance devices and treatment protocols, these practitioners and researchers have the potential to treat subjects who suffer from a wide range of diseases in a more efficient and minimally invasive manner. Present magnetic resonance device systems, however, require the expertise of a magnetic therapist who understands magnetic resonance, as well as subject treatments and diseases in order to treat a subject. Additionally, in research settings, current magnetic resonance devices are only used by magnetic resonance experts to develop new magnetic resonance protocols. Consequently, only magnetic resonance experts can administer the treatment, limiting its use while the public suffers from a shortage of magnetic resonance treatment professionals.

By creating a simplified magnetic resonance device system that allows a broader range of users such as, but not limited to, medical practitioners, alternative medicine providers, or home users, more patients suffering from a wide range diseases may be treated by either treating themselves or with the assistance of a general practitioner. Additionally, such a device can be used by non-medical personnel in connection with other uses, such as relaxation. Medical researchers who do not have a special expertise in magnetic resonance may contribute to the development of new and improved magnetic resonance treatment parameters and protocols for a broad range of diseases. Additionally, users such as patients can operate and treat themselves using the magnetic resonance device remotely, such as at home, eliminating the need to travel to or make appointments with a medical practitioner. Accordingly, there exists a need for a system that does not require an expertise in magnetic resonance such that more health-care practitioners, researchers, and subjects are able to use magnetic resonance devices and treatment protocols. Thus, there exists a need for a simplified magnetic resonance device system that allows a broad range of users to administer magnetic resonance treatments and to contribute to the development of new and improved magnetic resonance parameters and protocols.

Furthermore, current systems do not aggregate, analyze, and improve subject magnetic resonance development data and thus, do not provide the most current treatment protocols available. These systems do not provide therapies for subjects suffering across multiple disease states and/or conditions ("co-morbidities") in addition to their primary disease. Although there are a broad range of applications for treatment with PEMFs, the results of magnetic resonance treatment depend not only on the parameters of the fields, but also on the individual sensitivity of the person. A subject's predominant indication, medical history, biographical history, and prior treatment data, influence the subject's treatment parameters. Without using a subject's current state of health, prior medical history, and therapies that cover multiple disease states and/or conditions, current systems merely provide efficacious results to small homogenous populations found in clinical trials, rather than effective results across the diverse populations found in the real world, leaving the real subjects without the intended result.

Moreover, current systems lack the ability to capture and immediately consider the subject's sensitivity or biometric data through real-time data monitoring, increasing the risk of treatment error. An individual subject is generally required to heavily rely on the physician to set-up, administer, and adjust their treatment parameters without the benefit of receiving real-time data measurements during their treatment session. These real-time measurements can provide a compilation of data useful for analytical purposes in selecting future treatment protocols for subjects.

Additionally, if the system does not provide a systematic method of evaluating the subject's progress as the subject receives the treatment, the treatment parameters may not be readily adaptable. The treatment parameters may not be able to be modified at the subject's point of care if the operator does not have an expertise in magnetic resonance theory. In order to provide a method of evaluating a subject's progress as the subject receives a treatment, there exists a need for a system to capture and aggregate biometric measurement information for making real-time adjustments to current treatment parameters and a need to store information for analysis of future treatment protocols.

Also, currently a subject may provide verbal feedback of a treatment to his or her physician immediately after being given their magnetic resonance treatment. However, this may cause poor or incomplete information to be relayed to the physician when working with certain subject populations such as elderly subjects, children, patients suffering from dementia, or subjects within the general population who are inconvenienced (e.g., lack of time). In that case, the subject may not provide any feedback at all, or will provide a hastily given, and possibly less thorough, feedback response. Moreover, the feedback provided by the subject may typically be recorded in the subject's file by a physician and may not be in a format that lends itself to reporting. This creates a hindrance in quickly assessing the subject's treatment results and feedback data and stunts the research and development of better treatment protocols since non-identifiable subject data may be unable to be shared in a readily accessible and interactive medium.

In addition, current systems generally lack the ability to automatically understand a subject's progress through a systematic method of gathering feedback before, during, and after his treatment, regardless of the subject's location. Likewise, current systems lack the ability to for a subject to modify or to update his feedback responses after a treatment. The subject is expected to either make another appointment with the physician at a later date or wait until his next treatment in order to modify or update the feedback response to their prior treatment. This may cause the subject to fail to remember what modifications he wanted to make or to forget to address the modification at all. Consequently, a need exists for a flexible and accommodating method for the subject to provide and modify treatment feedback after his treatment and at his convenience. Thus, there exists a need for a readily accessible and interactive system to track and store reportable feedback given by subjects verbally, physically, biometrically, or by any other method of obtaining feedback, before, during, and after treatment.

Experts in the field of magnetic resonance continue to research the effect of PEMFs on various indications. For example, researchers test the effects of various PEMF parameters. As a result, researchers discover new and improved treatment parameters to apply in a clinical setting. One challenge is that these experts in the field of magnetic resonance may be isolated with their research and findings. It would be beneficial to compile and analyze this parameter data in order to use it to develop, improve, and define magnetic resonance treatment parameters. But current systems do not have this functionality, which negatively affects the ability of the physician to successfully treat or significantly benefit the myriad of symptoms presented to him with magnetic resonance treatment and the ability of the subject to receive new or improved treatment parameters.

Moreover, the current system lacks the ability to compile and measure actual subject results and feedback and provide improved treatment parameters based upon the compilation and analysis of those results and feedback. Each subject's results and feedback remain isolated. Thus, there exists a need for a system to compile, measure, and analyze subject results and feedback from magnetic resonance treatment and provide new or improved treatment parameters based upon the subject's results and feedback data. Additionally, there exists a need to integrate the system with web-based Health Insurance Portability and Accountability Act ("HIPAA") compliant systems to gather results, feedback, and additional data from subjects, clinical or medical organizations, hospitals, or medical offices across a broad range of the subject population. Integrating these systems may allow information to be constantly updated, thereby creating more customized treatments and provide for new or improved treatment parameters.

Presently, magnetic resonance treatments are designed to treat or benefit symptoms associated with a specific indication. Existing treatment parameters typically treat only a specific symptom or indication, failing to take into account a subject's medical history. Current systems lack the ability to take into account a subject's medical history when setting magnetic resonance treatment parameters. A subject may have underlying conditions that need to be treated with magnetic resonance in addition to the subject's predominant indication. Furthermore, two subjects suffering from a common indication but with different medical histories are often treated with the same treatment parameters. This method of treatment ignores the different medical histories of each subject and does not reflect the reality of a living being.

Furthermore, current systems generally lack the ability to personalize treatment parameters to treat an individual subject. As a result, subjects may not receive the correct treatment parameters to directly treat their conditions. Moreover, a subject who is suffering from various indications may be required to receive multiple treatments to remedy his indications. For example, a subject may have a medical history that includes Parkinson's disease, as well as heart disease. A second subject may suffer only from heart disease. Using current systems, both subjects may receive similar treatment parameters to treat their heart disease. However, the first subject, who is suffering from multiple indications, may not receive the most appropriate treatment parameter to treat his multiple indications. This is inefficient, time-consuming, and may be mentally and physically exhausting for a subject suffering from multiple indications. Thus, there exists a need for a system to predict which treatments may be most useful in treating subjects with various subject histories, including subjects with multiple indications.

Additionally, current systems lack the ability to promptly access, analyze, and determine a subject's treatment regimen, past and current medical history, treatment results and feedback, and biographical data. The ability to perform these tasks would provide more efficient, reliable, and effective treatment, providing information for future treatment enhancements and reducing treatment errors. Presently, a physician is required to search through a subject's file for the subject's treatment regimen, past and current medical history, treatment results and feedback, and biographical data. Then, to provide magnetic resonance treatment to the subject, a physician must compute the magnetic resonance treatment parameters, or have such computation performed, which generally requires a specific level of expertise.

When determining the treatment parameters, however, a physician may lack the ability to consider all of the subject's parameters into his computation. Although a physician may consider the subject's indication and the subject's past treatment regimen, a physician may not have the ability, in the time allotted during the subject's magnetic resonance visit, to consider other variables that may have an impact on the computation of treatment parameters such the subject's past and current medical history, the medications the subject may be taking, the subject's physiological data (e.g., blood pressure, weight, tremor rate, or pulse rate), as well as the time, date, latitude and location of the subject's magnetic resonance treatments.

Although current systems may allow a physician to refine treatment parameters based upon the subject's verbal feedback and/or the physician's physical observation of the subject, the physician may lack the ability to calculate the subject's non-verbal, real-time data and feedback, such as physiological data, into the adjusted treatment parameters. As a result, the subject may not receive the most accurate treatment parameters. Thus, there exists a need for a system that incorporates multiple subject data and feedback parameters, as well as magnetic treatment data, into algorithms to compute the best magnetic resonance treatment parameters and protocols.

SUMMARY

Embodiments of the present invention provide methods and systems that provide a magnetic resonance treatment to a subject.

Some embodiments of the present invention provide methods of providing a magnetic resonance treatment to a subject. A feature of such embodiments is that the method may comprise the steps of beginning a treatment of a subject, updating a treatment of a subject, and ending a treatment of a subject. Advantages of such embodiments may include, but are not limited to, treating pain, relieving symptoms, and/or increasing the effectiveness of drugs or other treatments, among others.

In some embodiments, the present invention provides a system that provides a magnetic resonance treatment to a subject. A feature of such embodiments is that the system may comprise a magnetic resonance device that may be in communication with a client computer that may be in communication with a network that may be in communication with a system server. Advantages of such embodiments may include, but are not limited to, treating pain, relieving symptoms, and/or increasing the effectiveness of drugs or other treatments, among others.

BRIEF DESCRIPTION OF THE DRAWINGS

These and other features, aspects, and advantages of the present disclosure are better understood when the following Detailed Description is read with reference to the accompanying drawings, wherein.

DETAILED DESCRIPTION

Figure 1:
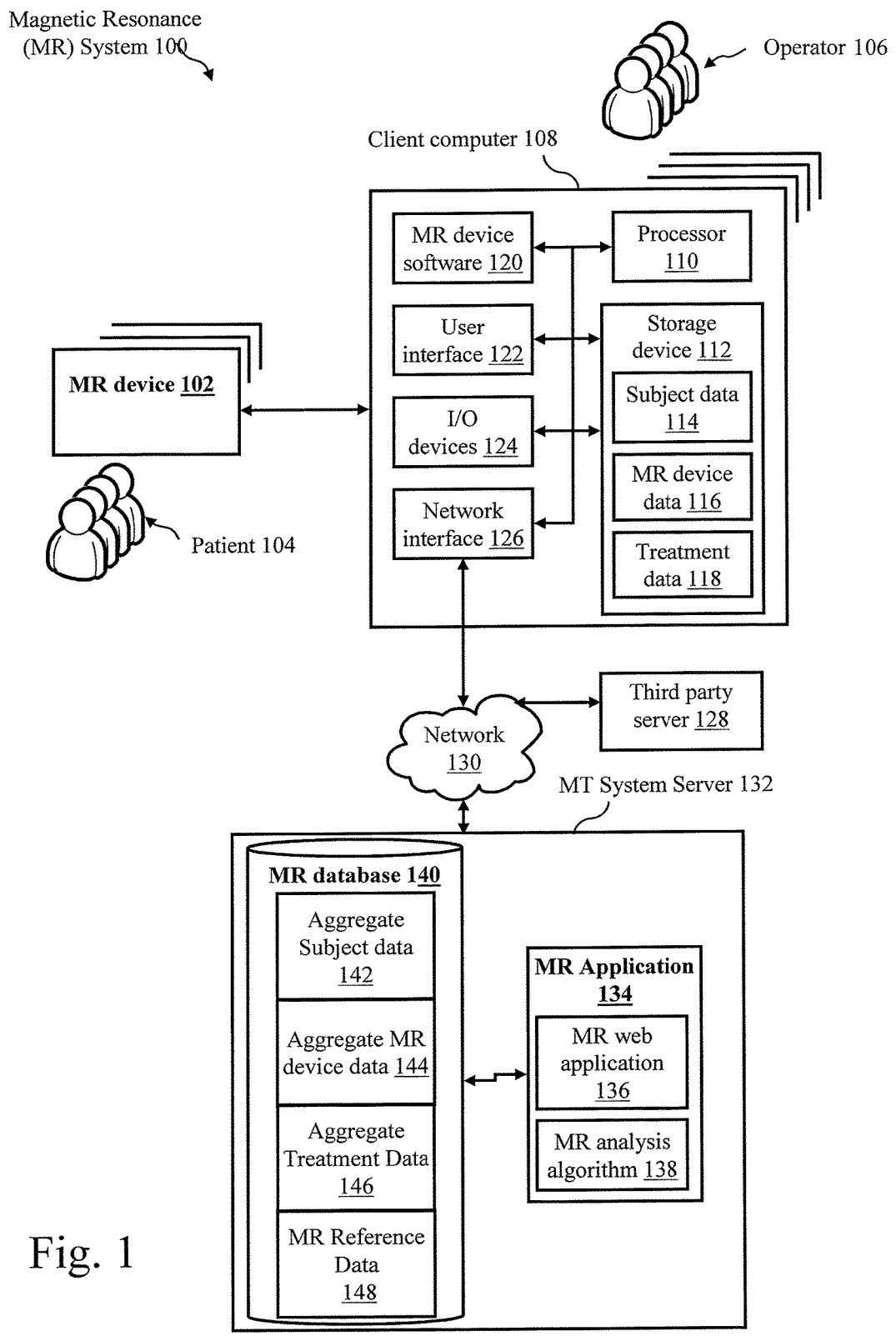
FIG. 1 is a diagram illustrating a system for providing a magnetic resonance treatment to a subject according to one embodiment of the invention.

Embodiments of the present invention provide methods and systems for providing a magnetic resonance treatment to a subject. Numerous modifications and adaptations are apparent to those skilled in the art without departing from the scope of this disclosure.

As set forth above, there is a need for a system that controls a magnetic resonance device and provides magnetic resonance treatments in an interactive and controlled manner. There is also a need for a simplified magnetic resonance device system that allows a broad range of users to administer magnetic resonance treatments and to contribute to the development of new and improved magnetic resonance parameters and protocols. Furthermore, there is a need for a readily accessible and interactive system to track and store reportable feedback given by subjects verbally, physically, biometrically, or by any other method of obtaining feedback, before, during, and after treatment. Still further, there is a need for a system to compile, measure, and analyze subject results and feedback from magnetic resonance treatment and provide new or improved treatment parameters based upon the subject's results and feedback data. Similarly, there is a need for a system that incorporates multiple subject data and feedback parameters, as well as magnetic treatment data, into algorithms to compute the best magnetic resonance treatment parameters and protocols.

The methods and systems described herein can be used to promote health and wellness. In various embodiments, the systems and methods may assist in providing relaxation and stress relief. Further, the systems and methods may be used in the context of traditional medicine or complementary alternative medicine. For example, some embodiments of the present invention are advantageously used to treat pain and relieve symptoms of a subject. The symptoms may be symptoms of a condition. The condition may be a disease, injury, or any other condition. It will be apparent to those of skill in the art, however, that methods and systems of the present invention may be advantageously used in many different environments.

By way of example, in a traditional medicine environment, it may be advantageous to provide a treatment to a subject based on a recommended treatment protocol from a system server. In another example, in a research environment, it may be advantageous to provide an electromagnetic field to a subject or object based on a protocol from a system server to observe the resulting effect.

In one embodiment of the invention, a method for providing a magnetic resonance treatment to a subject may be provided. In some embodiments, the method comprises beginning a treatment of a subject, updating a treatment of a subject, and ending a treatment of a subject.

In one embodiment, beginning the treatment of the subject comprises querying a database of a plurality of MR treatment protocols and/or parameters, generating treatment protocols based on a result of the query, and providing a treatment to the subject according to the selected treatment protocol. In a further embodiment, treatment of the subject comprises providing treatment protocols to a processor, selecting a treatment protocol on the processor, and initializing a magnetic resonance device. In another embodiment, subject data is collected and provided to a database.

In one embodiment, the subject data may be collected from the subject. In other embodiments the subject data may be collected from a third party, such as the subject's physician or a third-party network such as WebMD, Google Health, or others. In some embodiments, the subject data also comprises various types of information, including one or more of: demographic information, lifestyle information, time of treatment, date of treatment, location of treatment, health information, and magnetic resonance treatment history information.

In one embodiment, generating a future treatment protocol comprises at least one of acquiring prior treatment data of the subject, searching the database for a treatment of a subject with a medical history similar to the subject, or searching the database for a subject population trend. Acquiring prior treatment data of the subject may include any known method of obtaining data, for example, querying a database or obtaining the information from the patient or a representative of the patient. Such patient information may be provided verbally, in written form, in electronic form, or in any other known format. Prior treatment data may include records of prior treatments, protocols, or devices used. Prior treatment data may also include a subject's response to such prior treatments, protocols, or devices. The subject's response may take place during, before, or after treatment. The subject's response can include clinical measurement(s), patient-subjective outcome(s), sensor data, test data, and/or any other response.

In one embodiment, querying the database comprises searching the database for prior treatment data of the subject. Or querying the database may comprise searching the database for a treatment of a subject with a treatment history similar to the subject and/or searching the database for a subject population trend.

In some embodiments, generating a treatment protocol based on the result of the query comprises using an analysis algorithm to find an appropriate treatment for the subject. In one embodiment, the analysis algorithm comprises using prior treatment data. In one embodiment, the analysis algorithm comprises using similar treatment history to search for subjects with similar medical history and characteristics. In one embodiment, the analysis algorithm comprises using a subject population trend to find the appropriate treatment for the subject. A subject population trend may include data related to a population of which the subject is a member.

Further, the subject population trend may include information regarding how various pieces of data associated with the population are trending over a period of time. In one embodiment, the analysis algorithm comprises using treatment information regarding at least one of the time, season, latitude, or location of the magnetic resonance treatment to find the appropriate treatment for the subject.

In one embodiment, initializing the magnetic resonance device comprises selecting a treatment protocol from one or more recommended treatment protocols. In one embodiment, initializing the magnetic resonance device comprises applying a setting to the magnetic resonance device that is appropriate for the selected treatment and the subject. In another embodiment, initializing the magnetic resonance device comprises activating the magnetic resonance device. In an embodiment, the method comprises updating the treatment of the subject. In still other embodiments, initializing the magnetic resonance device comprises applying a setting to the magnetic resonance device that may be appropriate for the selected treatment and the subject. In a further embodiment, updating the treatment of the subject comprises at least one of monitoring the subject during the treatment, providing subject data to a processor, determining whether a treatment adjustment is needed (and if it is determined that the treatment adjustment is needed, identifying the needed adjustment), identifying a proper treatment protocol (based at least in part on whether the treatment adjustment is needed), selecting the treatment protocol on the processor, initializing a magnetic resonance device, and applying a treatment to the subject according to the selected treatment protocol.

In one embodiment, monitoring the subject during the treatment comprises using at least one of the following: a clinical measurement, a subject-reported outcome, a physician-reported outcome, a sensor, or a recording device. Furthermore, in some embodiments, determining whether a treatment adjustment may be needed comprises comparing an intended result of the treatment to an actual result of the treatment.

In one embodiment, ending the treatment of the subject comprises at least one of commanding a processor to end the treatment, collecting and storing subject data on the processor, providing the subject data to a database, querying the database, and/or generating a future treatment protocol based on a result of the query. In some embodiments, querying the database comprises searching the database for prior treatment data of the subject and/or searching the database for a treatment of a subject with a medical history similar to the subject and/or searching the database for a subject population trend. In still further embodiments, generating a future treatment protocol based on the result of the query comprises using an analysis algorithm to find an appropriate future treatment for the subject, and the analysis algorithm comprises using at least one of the following: prior treatment data, medical history, similar treatment history, time, date, latitude of location of MR treatment, or a subject population trend to find the appropriate treatment for the subject.

In one embodiment, the method for providing a magnetic resonance treatment to a subject further comprises attaining access to data of a treatment protocol. In some embodiments, attaining access to data of the treatment protocol comprises requesting access to data. In some embodiments, attaining access to data of the treatment protocol comprises determining if the requested data requires a subscription. If the requested data requires a subscription, attaining access to data of the treatment protocol may comprise determining if an operator has the subscription. In some embodiments, if the operator has the subscription, the operator may then access the data. In some embodiments, if the operator does not have the subscription, attaining access to data of the treatment protocol may comprise registering the operator for the subscription, purchasing the subscription, and accessing the data. In some embodiments, if the requested data does not require the subscription, attaining access to data of the treatment protocol may comprise accessing the requested data.

In one embodiment of the invention, attaining access to data of the treatment protocol comprises requesting access to data and subsequently determining whether the requested data requires a prescription. If the requested data requires a prescription, attaining access to data of the treatment protocol may comprise determining whether the subject has the prescription. In some embodiments, if the requested data does not require the prescription, or of the subject has the prescription, then the operator may access the data. In some embodiments, if the requested data requires the prescription, and the subject does not have the prescription, then the operator may be denied access to the data. In some embodiments, the method may further comprise adding treatment protocol data to a repository.

In some embodiments, the method may further comprise requesting a data and/or software update and downloading the data and/or software update. The data and/or software update may be provided to a magnetic resonance device. In some embodiments, the data and/or software update is provided to a computer.

In some embodiments, the method may further comprise executing a sweep protocol, generating a treatment protocol based on a result of the subject's feedback during the sweep protocol, providing the treatment protocol to a processor, selecting a treatment protocol on the processor, initializing a magnetic resonance device, and providing a treatment to the subject according to the selected treatment protocol.

In one embodiment of the invention, a system that provides a magnetic resonance treatment to a subject may be provided. In some embodiments, the system comprises components that may provide the system with an ability to treat and heal a subject. In further embodiments, the system is used for non-medical applications, such as comfort, relaxation, and/or wellness. Such embodiments may promote the general health and wellness of the subject. Examples of such components are identified and described herein.

In one embodiment, the system comprises a magnetic resonance device, wherein the magnetic resonance device may be in communication with a computer. In an embodiment, the computer comprises MR device software. In some embodiments, the computer is a client computer. In other embodiments, the computer is a system server. In some embodiments, the client computer may be in communication with a system server. In some embodiments, the client computer and system server may be in communication with a network. In some embodiments, the computer further comprises at least one of: a processor, a storage device, a magnetic resonance device software, a user interface, an input/output device, or a network interface.

In one embodiment, the storage device may be capable of storing at least one of: subject data, magnetic resonance device data, or treatment data. In some embodiments, the client computer may possess a shielding element that prevents electromagnetic radiation emanating from the client computer from interfering with the magnetic resonance device. In still further embodiments, the client computer may be connected to a magnetic resonance driver via a cable for operating the magnetic resonance device. In some embodiments, the client computer may be wirelessly connected to a magnetic resonance driver for operating the magnetic resonance device.

In various embodiments, the subject data comprises one or more of the following: subject characteristics, demographic information, lifestyle information, date of treatment, time of treatment, location of treatment, health information, medical history, magnetic resonance treatment history information, and information about responses to treatments. In some embodiments, magnetic resonance treatment history information comprises at least one of: the magnetic resonance protocols used, responses to magnetic resonance protocols used, the time of day, date, latitude, or location of the magnetic resonance treatments. Furthermore, in some embodiments, the magnetic resonance device data comprises a record of a setting for a magnetic resonance device. In one embodiment, the record of a setting for a magnetic resonance device comprises at least one of: information about the type of magnetic resonance device, information about a coil used in the magnetic resonance device, the order of steps in a magnetic resonance protocol, flux density, frequency, amplitude, intensity, voltage, waveform shape, or resonation duration of electromagnetic energy. Similarly, in another embodiment the treatment data comprises at least one of: a primary indication for which the subject may be treated, one or more secondary indication(s) for which the subject may be treated, sensor and recording device data, or a result of a treatment.

In one embodiment, the magnetic resonance device software may provide an ability to manage a setting of the magnetic resonance device. In some embodiments, the user interface may be a graphical user interface associated with the magnetic resonance device and the magnetic resonance device software.

In one embodiment, the network interface comprises a standard wired or wireless communication link for connecting to the network. In still further embodiments, the network comprises a wide area network (WAN) and/or a local area network (LAN) and/or a wireless network and/or a public telephone network and/or an intranet and/or the Internet.

In one embodiment, the system server comprises an application and a database. In a further embodiment, the application comprises a web application and an analysis algorithm. In some embodiments, the database may store one or more of the following: aggregate subject data, aggregate magnetic resonance device data, aggregate treatment data, and magnetic resonance reference data. In one embodiment, the aggregate subject data comprises a collection of subject data from the client computer of the magnetic resonance system. In other embodiments, the aggregate magnetic resonance device data comprises a collection of magnetic resonance device data from the client computer of the magnetic resonance system. In still other embodiments, the aggregate treatment data comprises a collection of treatment data from the client computer of the magnetic resonance system.

In one embodiment, the aggregate treatment data comprises data from at least one of: a subject-reported outcome, a physician-reported outcome, a sensor, a recording device, a magnetic assembly, or an environmental sensor. In some embodiments, the magnetic resonance reference data comprises a collection of a magnetic resonance treatment regimen and an associated result that may have been performed by use of the magnetic resonance system. Similarly, in further embodiments, the magnetic resonance device comprises a magnetic assembly that may be attached to a coil housing that may be in communication with a magnetic resonance driver.

In one embodiment, the magnetic resonance device further comprises a sensor. The sensor may comprise at least one of an environmental sensor or a recording device. In some embodiments, the magnetic resonance device further comprises at least one of: a magnetometer, a compensation network, or a cable. In still further embodiments, the sensor may have an ability to measure and record physiological data of the subject.

In one embodiment, the sensor or sensors comprise at least one of a blood pressure sensor, a perspiration sensor, a body weight sensor, a body temperature sensor, a haptics glove sensor, an electroencephalograph, or an electrocardiograph. In some embodiments, the environmental sensor may have an ability to measure and monitor an external force that influences a magnetic resonance treatment. Furthermore, in other embodiments, the sensor and the environmental sensor may be connected to a magnetic resonance driver via a wired or wireless communication means. In one embodiment, the recording device may have an ability to capture and record observational data. Similarly, in another embodiment, the recording device comprises a video camera. In still further embodiment, the recording device may be connected to a magnetic resonance driver via a wired or wireless communication means.

In one embodiment, the magnetic assembly comprises a magnetic coil configuration that produces a uniform magnetic field over a specific area of sufficient volume to accommodate a subject receiving a magnetic resonance treatment. In some embodiments, the magnetic coil comprises at least one of: a Helmholtz coil, a poloidal coil, a Maxwell coil, a solenoid coil, a toroidal coil, or a planar coil. In other embodiments, the magnetic assembly may be wired in parallel with the compensation network and may be electrically connected to the magnetic resonance driver. In still further embodiments, the coil housing comprises a chassis that provides an enclosure for the magnetic assembly and another component of the magnetic resonance device. In some embodiments, the coil housing may be made of a non-magnetic and non-conductive material.

In one embodiment, the magnetometer may have an ability to measure a magnetic field between coils of the magnetic assembly. In some embodiments, the magnetometer may allow the magnetic resonance driver to sense an ambient magnetic environment and to adapt its output to account for a magnetic field.

In one embodiment, the magnetic resonance driver comprises a low-level electronic waveform generator. In some embodiments, the magnetic resonance driver may possess a shield element that prevents electromagnetic radiation emanating from the magnetic resonance driver from interfering with the magnetic resonance device.

MR Systems and Methods of Use

Thus, in certain embodiments, the present invention relates to a system for and method of providing a magnetic resonance (herein "MR") treatment, where a system server may generate an actionable set of treatment recommendations, and a client with appropriate authorization may select one of the computer-generated treatment recommendations from his computing device, which then directs the MR device to provide the best MR treatment for that subject. Users such as subjects, general practitioners, service personnel, and research personnel employing a client computer may communicate with a MR system server via a network. The MR system server may store, collate, and analyze MR treatment and subject specific data and generates actionable MR treatment recommendations. All references to MR systems include electro-gravitational and/or electromagnetic-gravitational systems.

The term "patient" is used herein to describe any living system, such as any living animal, plant, and/or human, that may be the subject of the magnetic resonance treatment by use of the MR system of the invention. A patient may include any user of the MR system in any location, for example at home. The term "subject" is used herein to include a patient or any other person, animal, plant, or object upon which the MR system operates. The term "practitioner" is used herein to include, for example, physicians, physician assistants (PA), nurses, any other health care provider, or other professionals involved in complementary alternative medicine or promoting general health and wellness, such as chiropractors or acupuncturists. In further embodiments, the practitioner is also the subject. The term "research personnel" used herein includes, for example, clinical groups, medical scientists, or regulatory agencies. Additionally, the term "service personnel" includes, for example, device manufacturers, MR system maintenance personnel, database specialists, or computer specialists. All references to MR systems include electro-gravitational systems.

FIG. 1 is a diagram illustrating a system for providing a magnetic resonance treatment to a subject according to one embodiment of the invention. The MR system 100 may include an MR device 102, one or more client computers 108, a network 130, and an MR system server 132.

In one embodiment, an operator 106 utilizes the client computer 108. The operator 106 may be, for example, a subject 104, a general practitioner, a research personnel, a service personnel, and/or any individual trained to operate the MR device 102. The client computer 108 may be representative of a standard computing device, such as a personal computer, laptop, or host computer, capable of running the system control software for operating the MR device 102 and interfacing with the network 130. In one embodiment, the client computer 108 is a personal computer (PC) which includes at least one of a processor 110, a storage device 112, a MR device software 120, a user interface 122, a set of input/output (I/O) devices 124, and a network interface 126. In an alternate embodiment, the client computer 108 may contain a combination of one or more of these elements. The storage device 112 may include data such as, but not limited to, subject data 114, MR device data 116, and treatment data 118.

The client computer 108 may be a dedicated device for use only with the MR system 100, or a shared computing device, including other types of computing devices such as handheld devices, tablet PCs, personal digital assistants (PDA), cellular telephones, Web appliances or any machine or computing device capable of executing a sequence of instructions that specify actions to be taken by that machine or computing device.

In further embodiments, the client computer 108 possesses one or more shielding elements (not shown) that prevent electromagnetic radiation emanating from the PC from interfering with the operation of the MR device 102, for example, a chassis exterior having 20-thousands (0.02") steel, or 10-thousands (0.01") mu metal. In one embodiment, the client computer 108 is electrically connected to the MR driver 218 via one or more cables 216 (shown in FIG. 2) for operating the MR device 102 and interfacing with the network 130. In another embodiment, the client computer 108 may be connected via wired or wireless means and is capable of communicating with the MR system server 132.

The processor 110 may be any central processing unit (CPU), controller, or microcontroller device that is capable of managing the overall operations of the client computer 108, such as managing I/O devices, network communication, data exchange and storage, and executing the program instructions of any software applications that may be loaded on the client computer 108.

The storage device 112 may be, for example, any volatile or non-volatile data storage mechanism, such as, but not limited to, a random access memory (RAM) or other dynamic storage device, a computer hard drive, a floppy disk drive, a DVD, a CD-ROM, and any combinations thereof.

In one embodiment, the subject data 114, MR device data 116, and treatment data 118 are associated with the MR device 102 and the MR device software 120 and may be stored upon the storage device 112. The subject data 114 may be user-specific data of, for example, one or more subjects 104 of the MR system 100. The subject data 114 may include, for example, each subject's demographic information (e.g., age, gender, ethnicity, address), health information (e.g., personal medical history, family medical history), lifestyle information (e.g., smoker or non-smoker), and MR history information (e.g., a record of MR treatments). Subject data may also include the primary and secondary indication(s) that the subject is suffering from.

The MR device data 116 may include, for example, a record of the operational settings of the MR device 102 for each MR treatment of each subject 104. The operational settings of the MR device used to determine the treatment protocol may include flux density, frequency, amplitude, intensity, voltage, waveform shape, and resonation duration of the electromagnetic energy. In some embodiments, these determinations are based upon one or more of: the configuration of the MR device 102 (e.g., 7-foot or 22-inch MR device), the type of device (e.g., whole body immersion, partial body immersion), and the sequencing of the parameters. In one embodiment, the MR device data values of the operational settings are not disclosed to the operator 106 who is treating the subject 104. Rather, these values may be initially entered and stored by select operators such as a MR researcher with special access. The treatment data 118 may include, for example, the primary and secondary indication(s) that the subject is being treated for, sensor and recording device data, the results of one or more MR treatments as reported by the subject (subject-reported outcomes), and the results of one or more MR treatments as reported by a physician (physician-reported outcomes).

An instance of the MR device software 120 may also reside on each client computer 108, as the user interface 122. The MR device software 120 may be the device-specific control software of the MR device 102. For example, in one embodiment, the MR device software 120 provides the ability to manage the operational settings of the MR device 102, such as but not limited to, the flux density, frequency, amplitude, intensity, voltage, waveform shape, and duration of the electromagnetic energy that is supplied by the MR device 102. In some embodiments, these determinations are based upon one or more of: the model of the MR device 102 (i.e. 7-foot or 22-inch MR device), the type of device (i.e. whole body immersion, partial body immersion, etc.), and the sequencing of the parameters. The user interface 122 may be, for example, the device-specific graphical user interface (GUI) that is associated with the MR device 102 and the MR device software 120. The device-specific GUI (not shown) may be displayed to the user via the display of the client computer 108.

The I/O devices 124 may include, for example, a display device, a keyboard, a touch screen, mouse, speaker, voice recognition, system, and/or printer. The network interface 126 may be any standard wired (e.g., USB and/or Ethernet connection) and/or wireless (e.g., IEEE 802.11 and/or Bluetooth® technology) communications link for connecting to a network, such as the network 130. Third party servers 128 utilized by the operators 106, such as, but not limited to: research personnel; medical records sources, such as a web-based HIPAA compliant system; or doctor's offices, may also connect via the network 130. The network 130 may be, for example, a wide area network (WAN), a local area network (LAN), a wireless network, a public telephone network, an intranet, the Internet, or any other means of communication known in the art.

In some embodiments, the one or more client computers 108 that are associated with the one or more MR devices 102 are in communication with a centralized server via the network 130. More specifically, the magnetic resonance system 100 may include an MR system server 132, which may be any centralized computer that is accessible by other computers (e.g., client computers 108) via the network 130 and that is capable of hosting certain applications that are likewise accessible via the network 130. In one embodiment, the MR system server 132 is a centralized server that may store, collate, and analyze magnetic resonance treatment and subject-specific data in order to generate an actionable magnetic resonance treatment recommendation.

In one embodiment, the MR system server 132 includes an MR application 134. The MR application may, in certain embodiments, further include an MR web application 136 and/or an MR analysis algorithm 138. An MR database 140 may also reside on the MR system server 132. Stored on the MR database 140 may be a collection of any data that is related to magnetic resonance system 100, such as, but not limited to, aggregate subject data 142, aggregate MR device data 144, aggregate treatment data 146, and one or more tables of MR reference data 148.

The MR application 134 may be, for example, a custom application for managing the overall operations of the magnetic resonance system 100. The MR application 134 may manage the operations to store, collate, and analyze magnetic resonance treatment and subject-specific data in order to generate an actionable magnetic resonance treatment recommendation. The MR application 134 of the MR system server 132 may also be used to distribute any system data and/or software updates to authorized client computers 108 that are connected to the network 130. The MR application 134 may also be used to provide test, troubleshoot, and support services and activities.

Additionally, the MR application 134 may facilitate the use of the magnetic resonance system 100 by any authorized system administrator, authorized users of the one or more MR devices 102, and/or authorized operators 106 (e.g., general practitioners) of the one or more MR devices 102. That is, the MR application 134 may handle a security and authentication function for the magnetic resonance system 100 using standard security and authentication methods. The MR web application 136 of the MR application 134 may be, for example, a custom web application for accessing and using the MR application 134 of the MR system server 132 from a remote location, such as from any authorized client computer 108. Additionally, in one embodiment, by use of the MR analysis algorithm 138, the MR application 134 is able to query and analyze information that resides on the MR database 140 for information that may be used to develop a magnetic resonance treatment regimen for a certain user and/or indication.

As described herein, a need exists for a system that can provide treatment to heterogeneous subject populations. For example, in clinical trials, the subject populations are very homogenous (with strict inclusion/exclusion criteria involving subject's history and characteristics). But, when a drug or treatment is then approved to be practiced, the subject population is no longer the homogenous clinical trial group. Rather, the subject population is a heterogeneous group of subjects with any number of a variety of histories, characteristics, sicknesses, diseases, and/or conditions. One way in which embodiments of the present invention meet this need is by taking into account this very diverse population and developing treatment protocols through, for example, one or more of: the MR database 140, MR analysis algorithm 138, and protocol modification capabilities.

The MR database 140 may be created and maintained by any suitable database software, such as Oracle Database® from Oracle Corporation (Redwood Shores, Calif.). In one embodiment, the MR database 140 stores relationships between, for example, unique user information, MR device information, and/or information about certain indications. The contents of the MR database 140 may be organized in any user-defined relational database structure.

The aggregate subject data 142 may be a collection of all subject data 114 (e.g., user-specific data of subjects 104) from all authorized client computers 108 of the magnetic resonance system 100. The aggregate subject data 142 may be compiled from the subject data 114 that is transmitted from all client computers 108 to the MR system server 132 via the network 130. The aggregate subject data 142 may be updated in an ongoing fashion as new or updated subject data 114 is received.

The aggregate MR device data 144 may be a collection of all MR device data 116 (e.g., MR device-specific data of the MR devices 102) from all authorized client computers 108 of the magnetic resonance system 100. The aggregate MR device data 144 may be compiled from the MR device data 116 that is transmitted from all client computers 108 to the MR system server 132 via the network 130. The aggregate MR device data 144 may be updated in an ongoing fashion as new or updated MR device data 116 is received.

The aggregate treatment data 146 may be a collection of all treatment data 118 from all authorized client computers 108 of the magnetic resonance system 100 for primary and/or secondary indication(s) for which the subject is being treated. The aggregate treatment data 146 may be compiled from the treatment data 118 that is transmitted from all client computers 108 to the MR system server 132 via the network 130. For example, the aggregate treatment data 146 may include data from one or more sensors 204, environmental sensors 220, recording devices 206, and magnetic assemblies 208, shown, e.g., in FIG. 2. Further, the aggregate treatment data may include at least one of: subject-reported outcomes, physician-reported outcomes, or time, date, latitude and/or location of said treatments. In various embodiments, the latitude can be derived from a provided location by using, for example, GPS technology. The aggregate treatment data 146 may be updated in an ongoing fashion as new or updated treatment data 118 is received.

In one embodiment, the MR reference data 148 is a collection of MR empirical data that may be compiled over time. The MR reference data 148 may contain a record of all magnetic resonance treatment regimens and associated results that have been performed by use of the magnetic resonance system 100. The MR reference data 148 may include information from the aggregate subject data 142, aggregate MR device data 144, and aggregate treatment data 146 that is organized in an easily searchable fashion in order to accommodate the search and analysis operations of the MR analysis algorithm 138. While the information within the MR reference data 148 may include empirical data that is compiled from aggregate subject data 142, aggregate MR device data 144, and aggregate treatment data 146, the MR reference data 148 may also include data that is scientifically derived. More details of example records that may be contained in the MR reference data 148 are shown in Tables 1a to 1c. Tables 1a to 1c are exemplary and thus is non-limiting.

| S = Sex | A = Age |
| W = Weight | R = Race |

TABLE 1a

Aggregate Subject Data

| Record | Subect ID | 1° Subject Indication | 2° Subject Indication | S | R | A | W | Rec. Habits |
|---|---|---|---|---|---|---|---|---|
| 1 | A-84 | Parkinson's | Arthritis | F | Asian | 60 | 110 | Smoker |
| 2 | A-84 | Parkinson's | Arthritis | F | Asian | 60 | 110 | Smoker |
| 3 | A-84 | Parkinson's | Arthritis | F | Asian | 60 | 110 | Smoker |
| 4 | A-84 | Parkinson's | Arthritis | F | Asian | 60 | 110 | Smoker |
| 5 | A-96 | Parkinson's | Arthritis | F | Asian | 59 | 98 | Smoker |
| 6 | A-96 | Parkinson's | Arthritis | F | Asian | 59 | 98 | Smoker |
| 7 | A-96 | Parkinson's | Arthritis | F | Asian | 59 | 98 | Smoker |
| 8 | A-96 | Parkinson's | Arthritis | F | Asian | 59 | 98 | Smoker |
| 9 | B-21 | Parkinson's | Arthritis | F | Asian | 63 | 122 | |
| 10 | B-21 | Parkinson's | Arthritis | F | Asian | 63 | 122 | |
| 11 | B-21 | Parkinson's | Arthritis | F | Asian | 63 | 122 | |
| 12 | B-21 | Parkinson's | Arthritis | F | Asian | 63 | 122 | |
| 13 | C-37 | Parkinson's | Arthritis High BP Diabetes | F | Asian | 55 | 125 | |
| 14 | C-37 | Parkinson's | Arthritis High BP Diabetes | F | Asian | 55 | 125 | |

TABLE 1a-continued

Aggregate Subject Data

| Record | Subect ID | 1° Subject Indication | 2° Subject Indication | S | R | A | W | Rec. Habits |
|---|---|---|---|---|---|---|---|---|
| 15 | C-37 | Parkinson's | Arthritis High BP Diabetes | F | Asian | 55 | 125 | |
| 16 | C-37 | Parkinson's | Arthritis High BP Diabetes | F | Asian | 55 | 125 | |
| 17 | C-37 | Parkinson's | Arthritis High BP Diabetes | F | Asian | 55 | 125 | |
| 18 | D-58 | Parkinson's | High BP | F | Asian | 61 | 130 | |
| 19 | D-58 | Parkinson's | High BP | F | Asian | 61 | 130 | |
| 20 | D-58 | Parkinson's | High BP | F | Asian | 61 | 130 | |
| 21 | D-58 | Parkinson's | High BP | F | Asian | 61 | 130 | |

TABLE 1b

Aggregate MR Treatment

| Record | 1° Subject Indication Being Treated | 2° Indication being Treated | Sensor Data | Subjective Feedback Subject | Subjective Feedback Physician | Recording Device Data |
|---|---|---|---|---|---|---|
| 1 | Parkinson's | Arthritis | BP: 110/80; Tremor rating: 93 | Positive | Neutral | Rigidity, Slow movement, and mild postural imbalance |
| 2 | Parkinson's | Arthritis | No changes | Positive | Positive | Rigidity, Slow movement, and mild postural imbalance |
| 3 | Parkinson's | Arthritis | No changes | Positive | Positive | Rigidity, Slow movement, and mild postural imbalance |
| 4 | Parkinson's | Arthritis | Tremor Decrease by 5% | Positive | Positive | Reduced Rigidity; Slow movement; and mild postural imbalance |
| 5 | Parkinson's | None | BP: 125/75; Tremor rating: 100; | Neutral | Neutral | Rigidity |
| 6 | Parkinson's | None | No changes | Neutral | Positive | Rigidity |
| 7 | Parkinson's | None | No changes | Positive | Neutral | Rigidity |
| 8 | Parkinson's | None | Blood pressure decrease to 125/75; Tremor decrease by 5%; | Positive | Positive | Rigidity |
| 9 | Back Injury | None | BP: 120/80; Tremor rating: 95; | Neutral | Negative | mild postural imbalance |
| 10 | Back Injury | None | Tremor decrease by 10% | Positive | Positive | mild postural imbalance |
| 11 | Back Injury | None | Tremor decrease by 10% | Positive | Positive | mild postural imbalance |
| 12 | Back Injury | None | Tremor decrease by 15% | Positive | Positive | mild postural imbalance |
| 13 | Parkinson's | High BP | BP: 120/80; Tremor rating: 140; | Negative | Negative | Normal |
| 14 | Parkinson's | High BP | No changes | Negative | Neutral | Normal |
| 15 | Parkinson's | High BP | No changes | Negative | Neutral | Normal |
| 16 | Parkinson's | High BP | No changes | Neutral | Neutral | Normal |
| 17 | Parkinson's | High BP | No changes | Positive | Positive | Normal |
| 18 | Parkinson's | High BP | BP: 140/90; Tremor rating: 155; | Neutral | Negative | Slow movement |
| 19 | Parkinson's | High BP | No Change | Neutral | Neutral | Slow movement |
| 20 | Parkinson's | High BP | BP: 140/110; Tremor rating: 160 | Negative | Negative | Slow movement |
| 21 | Parkinson's | High BP | BP: 140/95; Tremor decrease by 4% | Positive | Positive | Slow movement |

TABLE 1c

Aggregate MR Device Data

| Record | Treatment Protocol # | Start/End | Date | Loc. | Dev. ID/Type | Sess. ID | O.S.* |
|---|---|---|---|---|---|---|---|
| 1 | 101 | Start | Jan. 2, YEAR | 123 Main Street | 31/7' | 1 | See Table 2 |
| 2 | 101 | — | Jan. 2, YEAR | 123 Main Street | 31/7' | 1 | See Table 2 |
| 3 | 101 | — | Jan. 2, YEAR | 123 Main Street | 31/7' | 1 | See Table 2 |
| 4 | 101 | End | Jan. 2, YEAR | 123 Main Street | 31/7' | 1 | See Table 2 |
| 5 | 101 | Start | Jan. 21, YEAR | 456 Broad Street | 31/7' | 1 | See Table 2 |
| 6 | 101 | — | Jan. 21, YEAR | 456 Broad Street | 31/7' | 1 | See Table 2 |
| 7 | 101 | — | Jan. 21, YEAR | 456 Broad Street | 31/7' | 1 | See Table 2 |
| 8 | 101 | End | Jan. 21, YEAR | 456 Broad Street | 31/7' | 1 | See Table 2 |
| 9 | 128 | Start | Jan. 21, YEAR | 789 Cherry Street | 31/7' | 2 | See Table 2 |
| 10 | 128 | — | Jan. 21, YEAR | 789 Cherry Street | 31/7' | 2 | See Table 2 |
| 11 | 128 | — | Jan. 21, YEAR | 789 Cherry Street | 31/7' | 2 | See Table 2 |
| 12 | 128 | End | Jan. 21, YEAR | 789 Cherry Street | 31/7' | 2 | See Table 2 |
| 13 | 116 | Start | Jan. 21, YEAR | 1991 Doggett Road | 31/7' | 3 | See Table 2 |
| 14 | 116 | — | Jan. 21, YEAR | 1991 Doggett Road | 31/7' | 3 | See Table 2 |
| 15 | 116 | — | Jan. 21, YEAR | 1991 Doggett Road | 31/7' | 3 | See Table 2 |
| 16 | 116 | — | Jan. 21, YEAR | 1991 Doggett Road | 31/7' | 3 | See Table 2 |
| 17 | 116 | End | Jan. 21, YEAR | 1991 Doggett Road | 31/7' | 3 | See Table 2 |
| 18 | 204 | Start | Jan. 21, YEAR | 1874 Russell Avenue | 31/7' | 4 | See Table 2 |
| 19 | 204 | — | Jan. 21, YEAR | 1874 Russell Avenue | 31/7' | 4 | See Table 2 |
| 20 | 204 | — | Jan. 21, YEAR | 1874 Russell Avenue | 31/7' | 4 | See Table 2 |
| 21 | 206 | End | Jan. 21, YEAR | 1874 Russell Avenue | 31/7' | 4 | See Table 2 |

Tables 1a to 1c represents a subset of records that may be the result of an analysis that is performed by the MR analysis algorithm 138 when determining magnetic treatment protocols to recommend to operator 106. For example, Table 1a represents a subset of records containing aggregate subject data; Table 1b represents a subset of records containing aggregate MR treatment; and Table 1c represents a subset of records containing aggregate MR device data. In this step, the MR system server 132 processes the request by searching the MR database 140 for like-situated subjects with similar aggregate subject data 142 including the primary subject indication group (e.g., illness or medical diagnosis) that the subject is suffering from, the secondary subject indication group that the subject is suffering from, sex, race, age, weight, and/or recreational habits (e.g., smoker, drug use, alcohol use). Other factors may include one or more of the time, date, latitude and location of the magnetic resonance treatment. Additionally, the MR system server 132 may search the aggregate MR treatment data 146 such as the primary indication being treated, the secondary indication(s) being treated, the treatment protocol ID number, sensor data, recording device data, subjective feedback from subject and general practitioner, clinical measurements, and subject reported outcomes. Additionally, the MR system server 132 may search for MR treatment protocols developed and stored in the MR database 140 by research personnel (not shown in Tables 1a to 1c). Afterwards, the aggregate MR device data 144 such as start/end time of MR treatment, the session ID, the device ID, and the operational settings which are shown in Table 2 are examined. While the contents of Tables 1a to 1c are specific to the Parkinson's and/or arthritis subjects example, the contents of Tables 1a to 1c may be tailored for any indication and/or condition and for any set of subject data, MR device data, and/or treatment data.

TABLE 2

Primary Indication: Parkinson's Disease
Treatment Protocol # 101

| Treatment Step # | Device ID#/Type | Frequency | Amplitude | Waveform Shape | Resonation Duration |
|---|---|---|---|---|---|
| 10 | 31/7' | 10 Hz | 0.01 microgauss | Sinusoidal | 15 minutes |
| 16 | 31/7' | 7 Hz | 0.02 microgauss | Sinusoidal | 25 minutes |
| 04 | 31/7' | 5 Hz | 0.03 microgauss | Sinusoidal | 12 minutes |
| 06 | 31/7' | 7 Hz | 0.025 microgauss | Sinusoidal | 18 minutes |

Once a subset of records of interest are identified, the MR analysis algorithm 138 may determine which record or records most closely match the circumstance of a certain subject 104 that is about to receive a treatment via a certain MR device 102. In this way, the MR analysis algorithm 138 may be used to generate a recommended magnetic resonance treatment regimen that may be transmitted to a certain client computer 108 for execution thereof.

The operational settings of the MR device 102 for each recommended treatment protocol are unique to the indication and treatment. For example, the MR device 102 may be capable of generating an electromagnetic field of a specified, but variable, flux density. Further, each MR device 102 may be capable of generating a specified, but variable, frequency. In some embodiments, the MR device 102 may be capable of producing an electromagnetic field with a variety of flux density ranges, including, for example, one or more of the following: from about 1 gauss to $10^{-50}$ gauss, or ranges within this range, such as $10^{-3}$ gauss to about $10^{-50}$ gauss; from about $10^{-10}$ gauss to $10^{-50}$ gauss; from about $10^{-20}$ gauss to $10^{-40}$ gauss; from about $10^{-5}$ gauss to $10^{-10}$ gauss; or from about $10^{-3}$ gauss to $10^{-6}$ gauss may be used. Or ranges within these ranges may be used.

In some embodiments, the MR device 102 may be capable of producing a flux density window in a variety of ranges, including from about 0.2 gauss to about 0.7 gauss. Or, ranges within this range may be used, e.g., from about 0.2 gauss to about 0.6 gauss; from about 0.4 gauss to about 0.7 gauss; from about 0.3 gauss to about 0.5 gauss; from about 0.2 gauss to about 0.4 gauss; or from about 0.2 gauss to about 0.3 gauss. Or ranges within these ranges may be used.

In some embodiments, the MR device 110 may be capable of producing a frequency in a variety of ranges, including from about 0 Hertz to about 1000 Hertz. Or, ranges within this range, e.g., from about 100 Hertz to about 900 Hertz; from about 5 Hertz to about 800 Hertz; from about 0 Hertz to about 500 Hertz; from about 0 Hertz to about 300 Hertz; or from about 10 Hertz to about 100 Hertz may be used. Or ranges within these ranges may be used.

In various embodiments, the preceding ranges may vary depending on the subject, substance, and/or intended results of the magnetic resonance treatment regimen. Examples of settings within the specified ranges include, but are not limited to: $0.075 \times 10^{-6}$ gauss at 2.1 Hz; $0.032 \times 10^{-6}$ gauss at 0.89 Hz to about 0.83 Hz; $0.343 \times 10^{-6}$ gauss at 9.6 Hz; $0.2 \times 10^{-6}$ gauss at 2.8 Hz to about 11.2 Hz; $0.3 \times 10^{-6}$ gauss at 0 Hz to about 17.0 Hz, more specifically at about 8.4 Hz; and $0.5 \times 10^{-6}$ gauss at 0 Hz to about 28.0 Hz, more specifically at about 14.0 Hz. Additionally, certain MR devices 102 may be whole body MR devices, meaning MR devices that are suitably large to resonate the whole body of the subject at one time (e.g., a whole body immersion device).

Table 2 depicts a subset of the device data used to determine the treatment protocol for a specific indication, in this case, Parkinson's disease. Table 2 is exemplary only. In one embodiment, the combination of treatment steps (steps 10, 16, 04, and 06) form treatment protocol #101 for treatment of Parkinson's disease. The values of these steps correspond to the "operational settings" column in Tables 1a to 1c. The device data values are not disclosed to the operator of the respective MR device.

Figure 2:
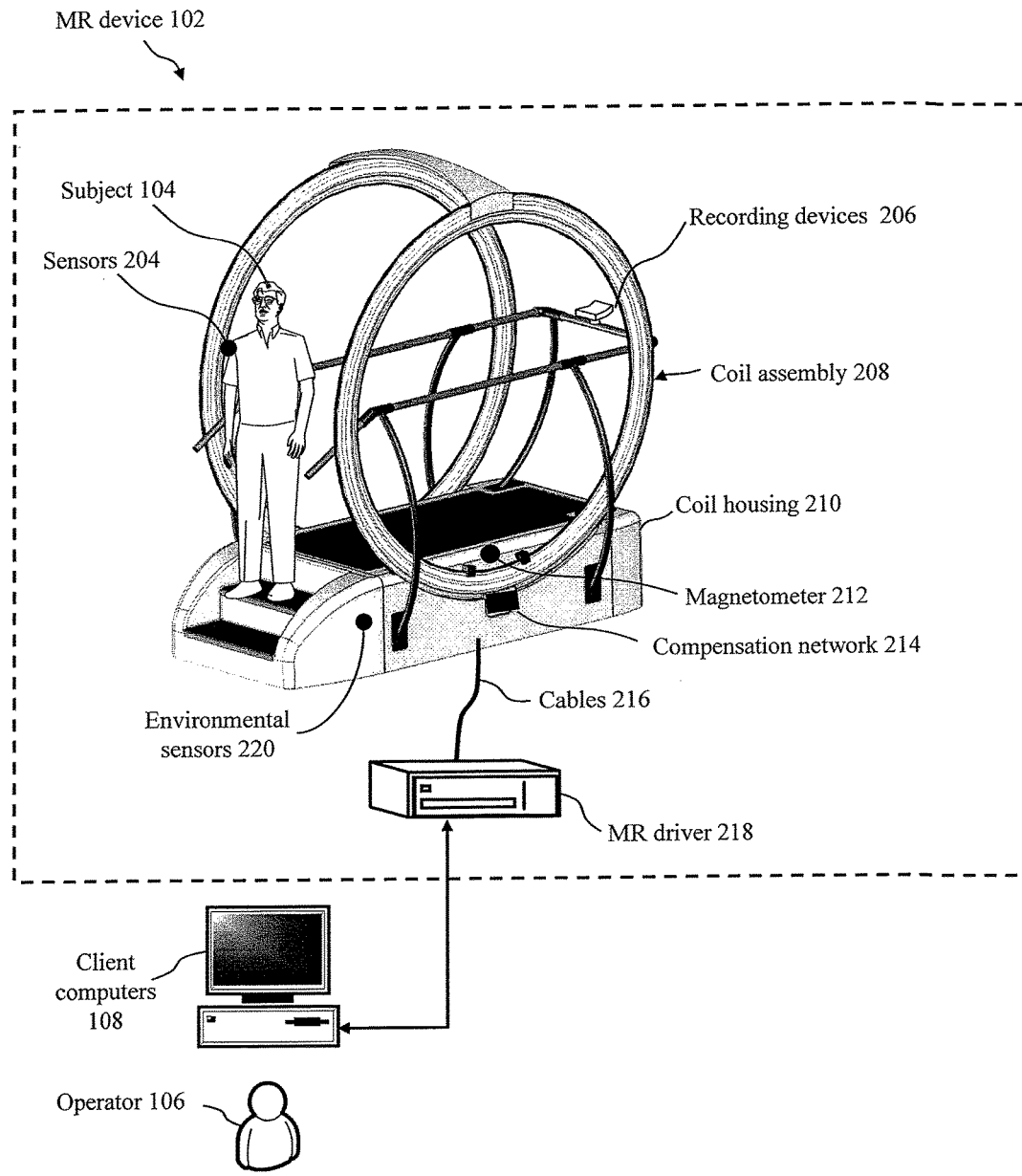
FIG. 2 is a diagram illustrating a perspective view of a magnetic resonance device according to one embodiment of the present invention.

FIG. 2 is a diagram showing a perspective view of a magnetic resonance device according to one embodiment of the present invention. The MR device 102 may include: one or more sensors 204, one or more recording devices 206, a magnetic assembly 208, a client computer 108, a coil housing 210, a magnetometer 212, a compensation network 214, one or more cables 216, an MR driver 218, and one or more environmental sensors 220. Also shown in FIG. 2 are the subject 104 receiving MR treatment and an operator 106 controlling the MR device 102.

In one embodiment, the magnetic assembly 208 and coil housing 202 are driven by a separate MR driver 218 that is electrically connected to the coil housing 202 via one or more cables 216. One or more recording devices 206 may be mounted upon the magnetic assembly 208. Also, a magnetometer 212 and a compensation network 214 may be mounted upon the coil housing 210. FIG. 2 shows a subject 104 that is receiving magnetic resonance via MR device 102. A set of sensors 204 may measure the subject 104 while the subject 104 receives the magnetic resonance treatment. For example, one or more environmental sensors 220 may be mounted upon coil housing 210. Further, in one embodiment a client computer 108, such as described in FIG. 1, is in communication with the MR driver 218 via an electrical connection.

If the client computer 108 is in physical proximity to the MR device 102, then the client computer 108 may be shielded. In one embodiment, the shielding elements (not shown) prevent electromagnetic radiation emanating from the PC from interfering with the operation of the MR device 102. For example, a chassis exterior may comprise 20-thousands (0.02") steel, or 10-thousands (0.01") mu metal.

In one embodiment, the client computer 108 is primarily used to: (1) request and select treatment protocols from the MR system server 132; (2) capture and submit data related to treatment sessions to the MR system server 132; (3) add or update treatment data to the MR system server 132; and (4) update system data and software from the MR system server 132.

In one embodiment, the one or more sensors 204 and environmental sensors 220 are connected to the MR driver 218 through any of a variety of communication means, both wired and wireless (not shown). Wired connection means may include wired communication standards such as USB and RS232 among others, while wireless connection examples may include Bluetooth (IEEE 802.15) and Wi-Fi (IEEE 802.11), among others. The sensors 204 include measuring devices which have the ability to measure and record physiological data. The sensors 204 can be introduced to the subject 104 externally or internally and can be used to measure and monitor biological data. Examples of the sensors 204 include blood pressure sensor 204a, perspiration sensor 204b, and body weight sensor 204c. Examples of the environmental sensors 220 include humidity sensors and temperature sensors (examples not shown). Additionally, the environmental sensors 220 can be placed surrounding the MR device 102 to measure and monitor external forces that may influence the overall MR treatment. These measurements can be correlated, stored, and used in developing further advancements of MR treatments.

Additionally, data taken from the sensors 204 may include measurements taken before and/or after a subject receives MR treatment. For example, a subject may be equipped with a heart rate monitor to measure the subject's heart rate between MR treatments. This data may be entered and stored in the MR database 140.

In one embodiment, the recording devices 206 are connected to the MR driver 218 through any of a variety of communication means, wired and/or wireless. These devices may have the ability to capture and record observational data. Wired connection means may include wired communication standards such as USB, while wireless connection examples may include using a wireless transmitter/receiver. Examples of the recording devices 206 include video cameras 206a, voice recorders (not shown), and motion capture devices (not shown). These measurements can be correlated, stored, and used in developing further advancements of MR treatments.

In one embodiment, the magnetic assembly 208 is representative of any magnetic coil configuration that produces a uniform magnetic field over a specified area of sufficient volume to accommodate a subject 104 receiving MR. An operator 106 of the client computer 108 can select a desired MR treatment protocol and send it to the magnetic assembly 208 for operation. Different size variations of the magnetic assembly 208 may allow the subject 104 to either receive treatment in a localized area of their body or receive whole body treatment. Additionally, in some embodiments, the magnetic assembly 208 allows the subject 104 to be in different positions when receiving the MR treatment. For example, the subject 104 may be in a supine or prone position, sitting position, standing position, in air, or submerged completely or partially in a substance such as $H_2O$.

In one embodiment, the magnetic assembly 208, as depicted in FIG. 2, includes a Helmholtz coil that further includes two co-axial 7-foot diameter coils spaced 3.5-feet apart, each coil having 30-turns of 30-gauge solid-core copper wire (not shown). However, other dimension coils with different number of turns and construction, such as 4 coil designs or 6 coil designs, are possible in accordance with the invention. In further embodiments, the magnetic assembly 208 may comprise one or more planar coils. A planar coil or planar antenna may comprise a planar spiral that can be used to create a magnetic field. Thus, one or more planar coils may be used in the system to generate the tunable and precise magnetic field Examples of other types of coils suitable for use in the magnetic assembly 208 include toroidal coils, poloidal coils, Maxwell coils, and solenoids. Various embodiments may include other types of coils, such as modified or multi-axis coils. Some examples of the types of coils that may be used are shown in FIGS. 10a-10o and the accompanying description. In some embodiments, the magnetic assembly 208 is wired in parallel with the compensation network 214, and is electrically connected to the MR driver 218, both housed within the chassis of the coil housing 210.

In one embodiment, the coil housing 210 is a chassis that provides an enclosure for the magnetic assembly 208 and other components of the MR device 102 as shown. The coil housing 210 may provide a platform for the subject 104 receiving MR to position himself within the magnetic assembly 208. The coil housing 210 may be constructed of a non-magnetic and non-conductive housing such as fiberglass or composite. A benefit of such construction is that it minimizes magnetic interference with the magnetic assembly 208. The coil housing 210 can be of a variety of sizes and shapes (i.e., form factors) capable of accommodating different sized and shaped magnetic assemblies 208. For example, in various embodiments, the magnetic assembly 208 can range in size from one inch or less to ten feet or more. Sizes commonly used in some embodiments include seven feet, four feet, and twenty-two inches. In addition, the coil housing 210 can also provide means of easily changing the position and orientation of the magnetic assembly 208. For example, in some embodiments, the coil housing may include an articulated mechanical arm for use with coils. In such embodiments, the mechanical arm may be attached to a platform. The platform may also be a structure. The structure may be movable, such as a chair, table, bed, or other structures. In other embodiments, the mechanical arm may be attached to a wall, ceiling, floor, or other structure.

In one embodiment, the magnetometer 212 is a magnetic sensor that measures the magnetic field between the coils of the magnetic assembly 208. The magnetometer 212 may be capable of measuring low-level magnetic fields, e.g., in the nano-Tesla range (i.e. 0.1 nT to 100 nT, at 5-10%), and of resolving the magnitude these fields into three orthogonal components (x-y-z). Examples of the magnetometer 212 include the GEM GSMP-20GS, a highly sensitive proton precession gradiometer with two aligned sensors, which has an RMS resolution of 0.05 pT, to the Ecoseal MAG-01H, single-axis fluxgate magnetometer with a resolution of 0.1 nT. The use of the magnetometer 212 allows the MR driver 218 to sense the ambient magnetic environment and adapting its output to account for this field. In some embodiments, the magnetometer 212 is electrically connected to the MR driver 218 via the cables 216.

In one embodiment, the compensation network 214 is a resistor and capacitor network that is matched to the impedance of the magnetic assembly 208, and used to negate the reactance of the coil over a small range of frequencies, for example, from 0 Hertz to 1000 Hertz.

The one or more cables 216 between the MR driver 218 and the coil housing 210 may include one or more coil cables. The cables 216 may include a PC communication cable which in this case, is a wired electrical connection. In one embodiment, the PC communications cable uses a power over Ethernet (POE) protocol. The PC communications cable may facilitate communications between the client computer 108 which is shielded (not shown) and the MR driver 218. In one embodiment, the coil cables are short electrical cables that have connectors that provide an analog signal that powers the magnetic assembly 208, which enables the magnetic assembly 208 to produce the specific magnetic waveform (e.g., magnitude and frequency) that is required for performing magnetic resonance. An example of these coil cables includes a shielded twisted pair that has a 156 Molex connector. Additionally, the cables 216 may include a magnetometer cable that provides a standard digital serial communication means, for example, USB or RS232, to enable the communication of magnetic field data between the magnetometer 212 and the MR driver 218. The magnetometer cable may provide power and ground to the magnetometer 212. Preferably, the MR driver 218 is located in close proximity to the magnetic assembly 208, thereby minimizing the length of the cables 216 and, therefore, minimizing electrical noise.

In one embodiment, the MR driver 218 is a custom low-level electronic waveform generator, for use in the MR device 102. In operation, the client computer 108 may communicate operational commands, such as normal operation on/off, AC calibration, and DC calibration to the MR driver 218 via the cables 216. For normal operation, the client computer 108 may further communicate specific magnetic waveform parameters, such as waveform type (e.g., sinusoidal, rectilinear, square), amplitude (e.g., 1 milli-volt) and frequency (e.g., 10 Hz) to the MR driver 218. Finally, the MR driver 218 possesses shielding elements (not shown) that prevent electromagnetic radiation emanating from the MR driver 218 from interfering with the operation of the MR device 102, for example, a chassis exterior having 20-thousands (0.02") steel, or 10-thousands (0.01") mu metal. These determinations may be based upon the type of the MR device 102 (e.g., 7-foot, 4-foot, or 22-inch MR device), the model of the MR device (e.g., whole body immersion, partial body immersion), and the sequencing of the parameters.

In one embodiment, and referring to FIGS. 1 and 2, the operation of magnetic resonance system 100 may be summarized as follows. Using the client computer 108, the operator 106 may select a certain magnetic resonance treatment and initiate operation of the MR device 102 for a subject 104 that is suffering, for example, from Parkinson's disease in a hospital or clinical setting. Before starting the magnetic resonance treatment, using the client computer 108, subject data may be collected from the subject such as the subject's primary and secondary indication(s) from which the subject is suffering from a disease, stress, pain, injury, or other discomfort. Next, the operator may determine the primary and secondary indication(s) for which the subject is being treated. The operator 106 may then generate user-specific data (e.g., subject data 114) or, optionally, may access user-specific data of the subject from the aggregate treatment data 146 of the MR system server 132 via the network 130 and display this information on the client computer 108. The operator 106 may also examine the type of the MR device 102 (e.g., 7-foot, 4-foot, or 22-inch MR device), the model of the MR device (e.g., whole body immersion, partial body immersion), and the sequencing of the parameters were used in the prior MR treatments or determine what type/model of device should be used during the treatment session. Additionally, the operator 106 may input additional subject specific data from the subject being treated into the client computer 108. Finally, the operator 106 may obtain clinical measurements, subject reported outcomes, biometric, physiological, and observational data from the subject 104 in addition to data from the sensors 204 and recording devices 206. The measurement and feedback (i.e., physiological and observational) data may be captured and stored in the client computer 108. A subject may be treated for his primary indication first and then his secondary indication(s), or may be treated simultaneously for both indications utilizing algorithms requiring certain inclusion/exclusion criteria for amplitude, frequency, wave form, duration and sequencing of magnetic field exposures. The operator 106 may make this determination based upon the subject data 114 and the treatment data 118.

During treatment, the operator 106 may measure subjective or perceptive data from the subject 104 in addition to physiological and observational data. Subjective information may include, for example, information related to the feelings, perceptions, and opinions of the subject 104. For instance, the subjective inquiries can measure responses from the subject 104 such as "How do you feel?" or "How is your pain?" In various embodiments, the feedback can be recorded through various methods. One embodiment includes the subject 104 using visual and audible cues. The subject 104 can press coded response buttons or type an appropriate response a keypad, connected to the client computer 108. Alternatively, the subject 104 can speak into a microphone and the client computer 108 will employ speech recognition software to capture the subjective data.

Further to the example, if the subject 104 is a first-time or new subject who is a 59-year old, 98-pound, Asian female that is seeking treatment for her primary indication, Parkinson's disease, the MR analysis algorithm 138 searches the MR reference data 148 for one or more treatment records that are related to Parkinson's disease and to users that most closely match a 59-year old, 98-pound, Asian female. In this example, the subject 104 is suffering from a primary indication, Parkinson's disease, and a secondary indication, arthritis. However, she is only being treated for her primary indication, Parkinson's disease. Once at least one substantially matching record of a like-situated subject is found, the MR application 134 and/or MR analysis algorithm 138 may generate one or more recommended magnetic resonance treatment protocols that are based upon the empirical and/or scientific data within the MR database 140. In one embodiment, and referring to Tables 1a to 1c, the MR analysis algorithm 138 analyzes the MR reference data 148 of the MR database 140 and determines that "Record 8" is a like-situated subject. As a result, the MR analysis algorithm 138 recommends substantially the same treatment protocol that is logged in "Record 8."

Subsequently, in one embodiment the selected magnetic resonance treatment protocol is transmitted from the MR system server 132 to the client computer 108. The operator 106 may then carry out the treatment protocol upon the subject 104 according to the recommended treatment protocol. For example, the recommended magnetic resonance treatment protocol may specify a certain number and frequency of treatment events. After each magnetic resonance treatment, all related data is updated locally at the client computer 108 and/or remotely at the MR system server 132.

In another example, where the subject has a primary indication of Parkinson's Disease and a secondary indication of osteoarthritis and will be treated for both conditions. The subject may begin treatment for PD in a 7' coil (i.e., whole body immersion) in fields ranging from 0.075 to about 0.078 microgauss at 2.1 to 2.2 Hz. The subject may be then treated for OA in a 22" coil (i.e., specific body part such as the "knee") in fields ranging from 0.032 to 0.031 microgauss and 0.27 to 0.457 microgauss at 7.5 Hz to about 12 Hz. And finally, the subject may finish his or her treatment protocol back in the 7' coil with the fields ranging as described above for the beginning of the treatment.

In another example, the subject 104 is a previous or prior subject who is a 60-year old, 110-pound, Asian female. She suffers from a primary indication of Parkinson's disease and a secondary indication of arthritis. She is seeking treatment for her primary indication Parkinson's disease and her secondary indication, arthritis. She will be treated for primary indication first and her secondary indication last during a treatment session. Both treatments for each indication may use the following method, although alternate methods may be used.

In one embodiment, the MR analysis algorithm 138 first searches the MR reference data 148 for one or more prior treatment records with positive feedback for that subject. If unable to locate any of the subject's prior treatment records with positive feedback, then the MR analysis algorithm 138 may search for records that are related to the primary and/or secondary indication(s) and to users that most closely match a 60-year old, 110-pound, Asian female. Once the subject's prior treatment record with positive feedback is found, the MR application 134 and/or MR analysis algorithm 138 may present the recommended magnetic resonance treatment protocols from that prior positive feedback treatment record. In one embodiment, and referring to Tables 1a to 1c, the MR analysis algorithm 138 analyzes the MR reference data 148 of the MR database 140 and determines that the treatment protocol ID from "Record 4" is the most recent prior positive feedback treatment record for that subject. As a result, the MR analysis algorithm 138 recommends the same treatment protocol that is logged in "Record 4."

Subsequently, the selected magnetic resonance treatment protocol may be transmitted from the MR system server 132 to the client computer 108. In one embodiment, the operator 106 then carries out the treatment protocol upon the subject 104 according to the recommended treatment protocol and device type/model. For example, the recommended magnetic resonance treatment protocol may specify a certain number and frequency of treatment events. After each magnetic resonance treatment, all related data may be updated locally at the client computer 108 and/or remotely at the MR system server 132 and a treatment protocol may be generated for the next treatment session for that particular subject. After completing the treatment for the subject's first indication, the operator 106 may begin treatment for the subject's second indication, either simultaneously (i.e., in the same treatment session) or sequentially (i.e., in a different treatment session, such as a different day of treatment).

Figure 3:
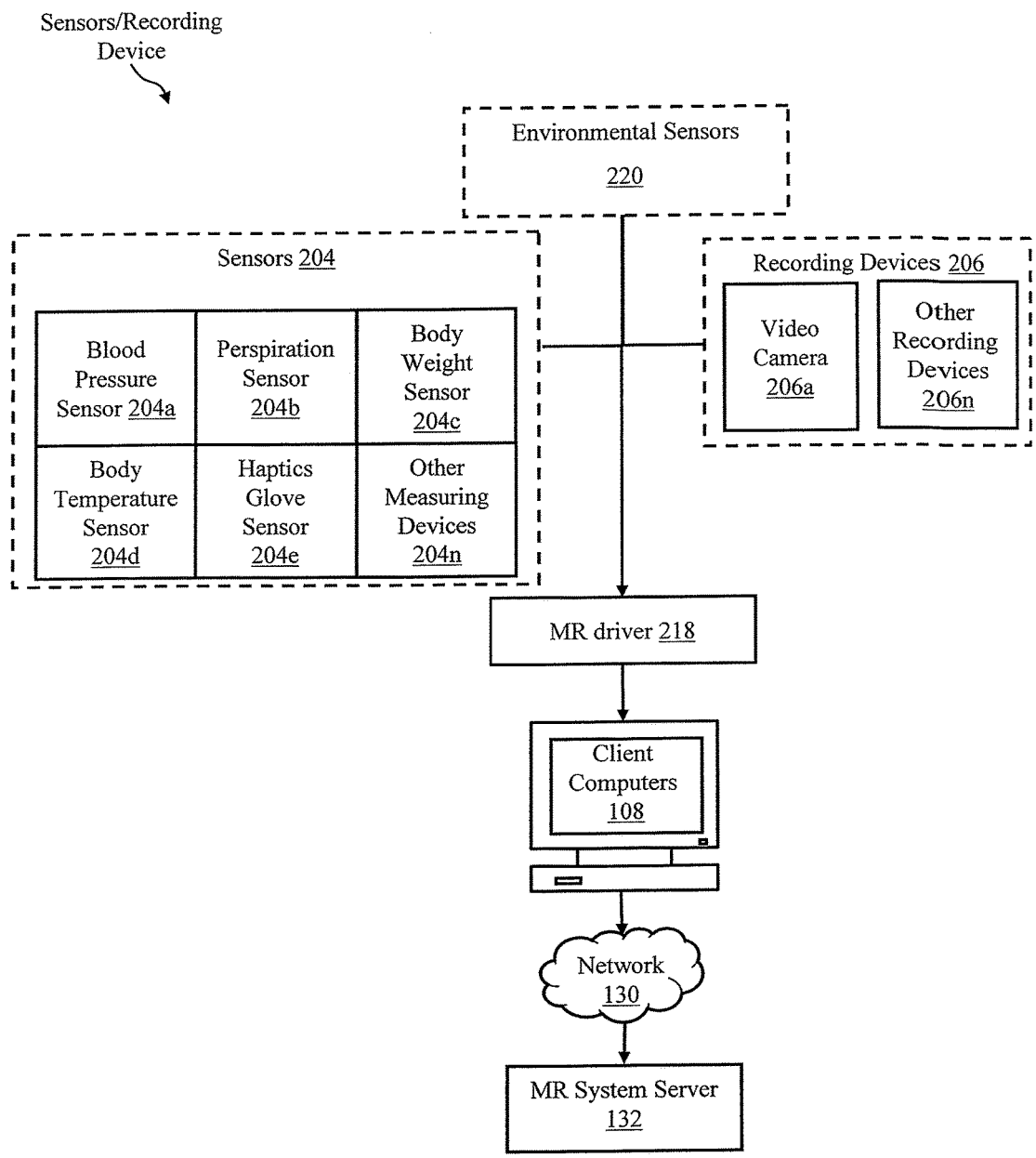
FIG. 3 is a diagram illustrating information flow from one or more sensors, environmental sensors, and recording devices to a network according to one embodiment of the present invention.

FIG. 3 is a diagram illustrating information flow from one or more sensors that are in communication with the subject, environmental sensors, and/or recording devices to a network according to one embodiment of the present invention. In this embodiment, information may flow from the sensors and recording devices to the MR System Server 132 via network 130 and the MR driver 218.

In one embodiment, the sensors 204 are representative of one or more sensors, including, for example, biometric sensors that are in communication with the subject. Biometric sensors may measure and collect sensor data before, during, and after MR treatment for a variety of physical parameters including physiological functions. These sensors 204 may measure the biological functions of the subject 104 receiving treatment in the MR device 102. The sensors 204 may include, for example, a blood pressure sensor 204a, a perspiration sensor 204b, a body weight sensor 204c, a body temperature sensor 204d, a haptics glove sensor 204e, and/or other sensors 204n to measure additional physiological functions such as heart rate, physical strength, electroencephalograph (EEG), electrocardiograph (EKG), and others. In one embodiment, the MR driver 218 relays this data to the client computer 108 and then to the MR system server 132 via the network 130. This data is stored in the MR database 140 in the MR system server 132.

An alternate embodiment of the present invention may employ sensors 204 that relate specifically to the indication or condition of the subject 104. For example, the subject 104, suffering from Parkinson's disease may employ a haptics glove sensor 204e to measure the tremor severity, range of movement, speed of movement, finger fractionation, or strength of movement of the subject 104. The haptics glove sensor may employ sensing systems which may comprise one or more of a linear sensor, an abduction angular sensor, a flexion angular sensor and/or a force sensor. The linear sensor can include a reflective infrared sensor which is activated by receipt of transmitted infrared waves which are reflected from a mirror attached to a bottom surface of the piston. The abduction angular sensor and flexion angular sensor can measure respective motions based on measurement of a magnetic field on two perpendicular axes. The force sensor can include a strain gauge for measurement of deformation of the palm base due to pressure applied by the fingertips. An example of a type of haptics glove sensor that may be used is the "Rutgers Master II-ND" glove described in "Proceedings of the 10th Symposium on Haptic Interfaces for Virtual Environment and Teleoperator Systems," in M. Bouzit, et al. (IEEE Computer Society).

In yet another embodiment of the present invention, the environmental sensors 220 may be used to record non-subject specific characteristics, such as air quality, humidity, oxygen level, barometric pressure, light intensity, and sound.

In one embodiment, the recording devices 206 include a video camera 206a and/or other recording devices 206n to capture observational data and record the subject's 104 response and feedback to an MR treatment protocol. In one embodiment, a video camera 206a is mounted to acquire video of subject 104 during treatment. Further, a wireless video receiver may receive the video signal from the video camera 206a; and a PC video/USB adapter may plug into the USB port of the client computer 108 and into the wireless video receiver. The MR driver 218 relays this data to the client computer 108 and then to the MR system server 132 via the network 130. This data is stored in the MR database 140 in the MR system server 132.

In yet another embodiment, once the data from the sensors 204, recording devices 206, and/or environmental sensors 220 is collected, an analog to digital (A/D) adapter (not shown) converts the analog data from the sensor and/or recording device into digital format and transmits it to the MR driver 218. In some embodiments, the driver may adapt its output in order to account for the data collected by the sensors 204, recording devices 206, and/or environmental sensors 220. The MR driver 218 may relay this data to the client computer 108 and then to the MR system server 132 via the network 130. In some embodiments, this data is stored in the MR database 140 in the MR system server 132.

In some embodiments, the aggregate treatment data 146 (FIG. 1) may include data from the one or more sensors 204, recording devices 206, magnetic assembly 208, and/or environmental sensors 220 within the MR device 102. In one embodiment, this collection of data is also transmitted to the MR system server 132 via network 130

For instance, in an embodiment, an analog to digital adapter (not shown) converts data collected from the blood pressure sensor 204a to digital format to MR driver 218. The blood pressure sensor data may then be transmitted to the client computer 108 and stored in the MR system server 132 via the network 130.

Figure 4:
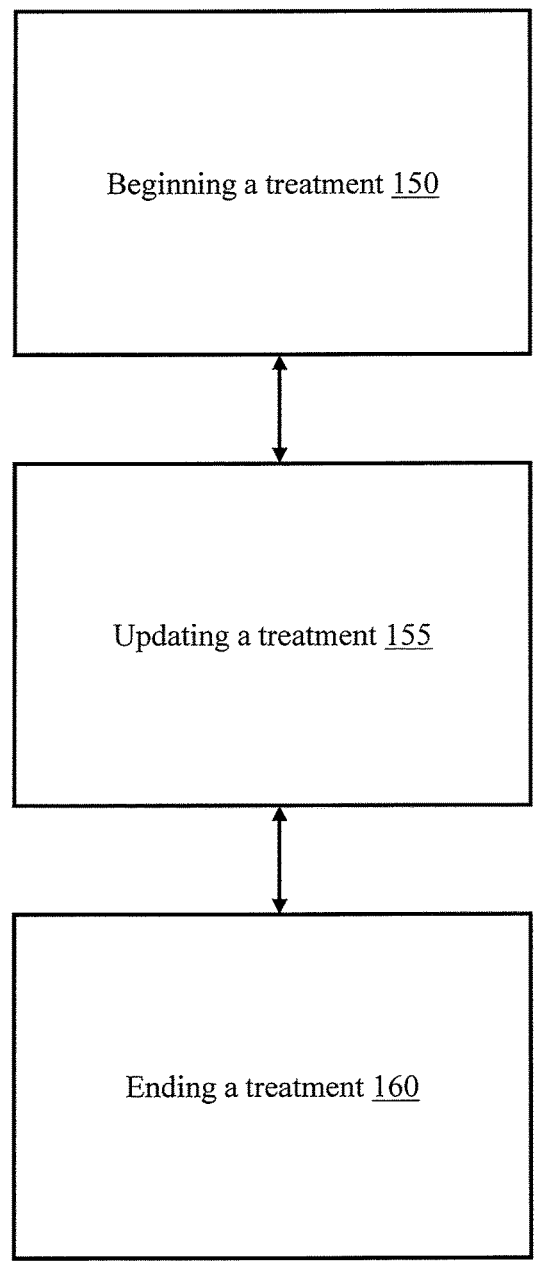
FIG. 4 is a diagram illustrating a method of providing a magnetic resonance treatment to a subject according to one embodiment of the invention.

FIG. 4 is a diagram illustrating a method of providing a magnetic resonance treatment to a subject according to one embodiment of the invention. The method 145 begins with step 150. In this step, an operator begins a magnetic resonance treatment of a subject. In some embodiments, step 150 comprises at least one of collecting subject data, providing the subject data to a database, querying the database, generating treatment protocols based on a result of the query, providing the treatment protocols to a processor, selecting a treatment protocol on the processor, initializing a magnetic resonance device, and/or providing a treatment to the subject according to the selected treatment protocol.

The method 145 may proceed to step 155, where the operator updates the treatment of the subject. In one embodiment, the operator may update the treatment of a subject at any time after the operator begins the treatment in step 150. Step 155 may comprise at least one of monitoring the subject during the treatment, providing subject data to a processor, determining whether a treatment adjustment is needed, and if it is determined that the treatment adjustment is needed, identifying the needed adjustment, identifying a proper treatment protocol, based at least in part on whether the treatment adjustment is needed, selecting the treatment protocol on the processor, initializing a magnetic resonance device, and/or applying a treatment to the subject according to the selected treatment protocol.

The operator may proceed to step 160, where the operator ends the treatment of the subject. Step 160 may comprise at least one of commanding a processor to end the treatment, collecting and storing subject data on the processor, providing the subject data to a database, querying the database, or generating a future treatment protocol based on a result of the query.

Figure 5:
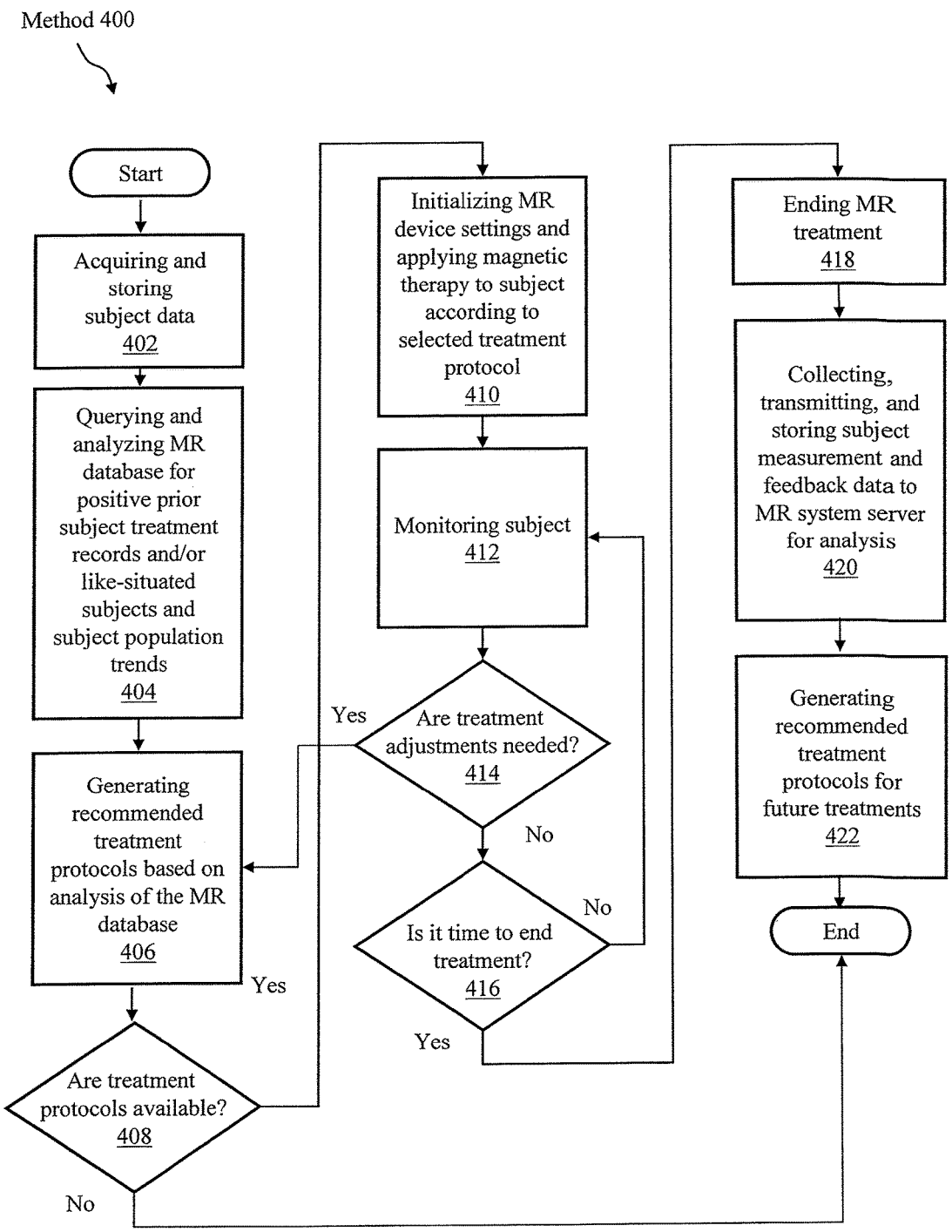
FIG. 5 is a diagram illustrating a method of utilizing a magnetic resonance treatment system according to one embodiment of the present invention.

FIG. 5 is a diagram illustrating a method 400 of utilizing a magnetic resonance treatment system according to one embodiment of the present invention. As described herein, a need exists for a system that can provide treatment to heterogeneous subject populations with any number of a variety of medical histories, characteristics, sicknesses, diseases, and/or conditions. One way in which embodiments of the present invention meet this need is by taking into account this very diverse population and developing treatment protocols through utilizing, for example, one or more of: the MR database 140, MR analysis algorithm 138, and protocol modification capabilities. One embodiment meets this need by performing method 400. In one embodiment, method 400 of utilizing the MR system 100 includes the following steps:

Step 402: Acquiring and Storing Subject Data:

In this step, according to one embodiment, the operator 106 of the client computer 108 acquires and stores subject data 114. The subject data 114 may be acquired from third party networks (e.g., web-based systems) via the third party server 128. Then, the operator 106 may login to the MR application 134 of the MR system server 132 using the MR web application 136. The operator 106 may ask the subject 104 the reason he or she is seeking MR treatment (e.g., questions such as "what brings you here today?" or "what caused you to seek treatment today?"). In one embodiment, the operator 106 may determine the primary and secondary indication(s) for which the subject is being treated. This may be different than the indication(s) that the subject may be suffering from. Based upon the response by the subject 104, the operator 106 will initiate a search for that primary indication to be treated. If the subject 104 has had previous magnetic resonance treatments and was treated for the same indication, the operator 106 may retrieve prior subject-specific and MR treatment information of the subject 104 from the aggregate subject data 142 and aggregate treatment data 146 on the MR database 140 of the MR system server 132 via the network 130. Once retrieved, the operator 106 completes subject registration and stores subject-specific information in the subject data 114 of the client computer 108. In some embodiments, the subject-specific information includes primary and secondary indication(s) that the subject is suffering from, subject biographical data (e.g., name, address, and date of birth); past and current subject medical history (e.g., individual and family medical history, and prior methods of treatment); results of disease-specific tests such as the Unified Parkinson's Disease Rating Score (UPDRS); and medications currently and previously administered. In one embodiment, the operator 106 also examines the type of the MR device 102 (e.g., 7-foot, 4-foot, or 22-inch MR device), the model of MR device (e.g., whole body immersion, partial body immersion), and the sequencing of the parameters were used in the prior MR treatments. It should be noted that in various embodiments, the MR device 102 can range in size from one inch or less to ten feet or more, and these listed sizes are not intended to limit the scope of the invention described herein. If no subject-specific information is present on the MR database 140 for the subject 104, then the operator 106 may acquire (e.g., by oral or written questionnaire) subject-specific information from the subject 104. In one embodiment, this information is recorded in the subject data 114 of the client computer 108.

For example, a subject 104 may be suffering from a primary indication of Parkinson's disease and a secondary indication of arthritis. However, the subject 104 injures his back and seeks MR treatment for only his back injury. Thus, although the subject 104 is suffering from multiple indications, he may only be treated for his back injury. In which case, the primary indication for which he is being treated is his back injury and he will not be treated for any secondary indication(s). Thus when the operator 106 treats the subject, the operator will determine that the primary reason of subject 104 to seek treatment is his back injury. In some embodiments, when seeking recommended treatment protocols the MR analysis algorithm 138 will search for treatment protocols for the primary indication for which to be treated (in this example, back injury) by first searching for positive prior subject treatment records, and then for records with similar primary and secondary indication(s) (in this example, Parkinson's disease and arthritis, respectively) from which the subject is suffering. In such cases one or more specific algorithms may be utilized to therein effectively treat back injury and not interfere with the Parkinson's Disease signs and symptoms which require different magnetic treatment parameters. In some cases, it may be necessary to amend the "back injury" treatment parameters in such a manner so as to include a PD signal protocol in the 7' coil to conclude the treatment for the back injury. An example of this type of subject is shown in Tables 1a to 1c "Records 9-12." Method 400 may proceed to step 404.

Step 404: Querying and Analyzing Magnetic Resonance Database for Positive Prior Subject Treatment Records and Like-Situated Subjects and Subject Population Trends:

In this step, according to one embodiment, the operator 106 submits a request for magnetic resonance treatment protocols for the subject being treated. The request may be made via the client computer 108 and transmitted and processed at the MR system server 132. Subsequently, the MR database 140 may be queried and analyzed first for prior subject treatment data and then for like-situated subjects (e.g., matching diseases with similar test scores or ratings for that particular indication), and subject population trends (e.g., substantially matching user information and indications). Method 400 may proceed to step 406. As used herein, a "like-situated subject" is a subject having similar lifestyle habits, gender, ethnicity, diagnosis (including primary and/or secondary indications), medical history, and/or physical characteristics. As used herein, "subject population trends" may include data regarding changes in information about a plurality of subjects. For example, a subject population trend may include a rate of change in one or more symptoms over a period of time.

Step 406: Generating Recommended Treatment Protocols Based on Analysis of the Magnetic Resonance Database:

In this step, according to one embodiment, by use of the MR analysis algorithm 138 and/or MR application 134, recommended magnetic resonance treatment protocols are generated based on the results from analyzing the information in the MR database 140. In one embodiment, the MR analysis algorithm 138 and/or MR application 134 initially searches prior subject treatment data and if none is found, then searches data of like-situated subjects. Additionally, the MR analysis algorithm 138 uses subject specific data from prior subject treatment data and then from like-situated subjects and subject population trends for that particular illness stored in the MR database 140. Subject population trends may include clinical data for MR treatment protocols for various illnesses provided by other operators 106, such as research personnel.

In one example, the subject-specific information specifies a 55-year old, 125-pound, Asian female that is seeking treatment for her primary indication, Parkinson's disease. She has multiple secondary indications (in this instance, high blood pressure, arthritis, and diabetes). She will first be treated for her primary indication, Parkinson's disease. After her treatment for Parkinson's disease is completed, she will then be treated for one of her secondary indications (in this instance, high blood pressure). She may be treated for more than one secondary indication. Therefore, in one embodiment, the MR analysis algorithm 138 of the MR system server 132 initially searches the MR reference data 148 for her prior subject treatment data and then for one or more treatment records that are related to Parkinson's disease, and to subjects that most closely match a 55-year old, 125-pound, Asian female. One example of the result of the query that is performed by the MR analysis algorithm 138 is shown in Tables 1a to 1c, "Records 13-17." In one embodiment, if positive prior treatment data is found for that subject, then the MR application 134 and/or MR analysis algorithm 138 of the MR system server 132 generates the recommended magnetic resonance treatment protocols with the corresponding device type/model from that prior subject treatment data and transmits the protocol to the client computer 108 of the requesting general practitioner as demonstrated in "Row 1A" in Table 3. In Table 3, "Record 1A" may be selected as the record that 100% matches this scenario and, thus, a treatment protocol that is substantially the same as shown in "Record 1A" is recommended. An example of how the MR analysis algorithm 138 performs the query is demonstrated in Method 500, depicted in FIG. 6 and discussed herein.

TABLE 3

Today's Date: February 8, YEAR

| Subject ID | Age | Race | Sex | Weight (lbs) | Recreational Habit(s) | Primary Indication (subject is suffering from) | Secondary Indication(s) (subject is suffering from) |
|---|---|---|---|---|---|---|---|
| C-37 | 55 | Asian | F | 125 | Smoker | Parkinson's Disease | Arthritis<br>High BP<br>Diabetes |

| | | Primary | Secondary | Prior Magnetic Therapy Treatments Device Type: 7' | | | |
|---|---|---|---|---|---|---|---|
| Subject ID | Current Medication | Indication To Be Treated | Indication (s) To Be Treated | Loc. | Date | Treatment Protocol | Feedback |
| C-37 | 1. Lipitor<br>2. Actonel<br>3. Vioxx | Parkinson's Disease<br>Initial Observations<br>1. Rigidity;<br>2. Slow Movement<br>3. Mild Posture Imbalance | High BP | 1991 Doggett Road<br>1991 Doggett Road<br>1991 Doggett Road<br>1991 Doggett Road<br>1991 Doggett Road | 01-21-YY<br>12-05-YY<br>11-15-YY<br>11-08-YY<br>10-24-YY | 116<br>116<br>103<br>103<br>102 | Positive<br>Positive<br>Neutral<br>Neutral<br>Negative |

| | Row | Protocol | Loc. | Match % | Ave. Age | Ave. Weight (lbs) | No. of sessions treatment protocol used | Overall Feedback of Treatment Protocol (% Positive) |
|---|---|---|---|---|---|---|---|---|
| Primary Subject Indication | 1A | 116 | 1991 Doggett Road | 100% | 55.0 | 125 | 40 | 98.6 |
| Group To Be Treated: | 1B | 102 | 1991 Doggett Road | 90.0 | 56.5 | 126 | 42 | 98.6 |
| Parkinson's Disease | 1C | 103 | 1991 Doggett Road | 80.0 | 58.8 | 126 | 31 | 95.3 |
| Device Type: 7' | 1D | 108 | 1991 Doggett Road | 70.0 | 59.6 | 120 | 12 | 92.1 |

| | Row | Protocol | Match % | Average Age | Average Weight (lbs) | No. of sessions treatment protocol used | Overall Feedback of Treatment Protocol |
|---|---|---|---|---|---|---|---|
| Primary Subject Indication | 2A | 101 | 90.0 | 59.8 | 109 | 40 | 96.3 |
| Group To Be Treated: | 2B | 129 | 70.0 | 61.6 | 106 | 106 | 94.1 |
| Parkinson's Disease | 2C | 124 | 70.0 | 62.4 | 115 | 30 | 92.5 |
| Device Type: 7' | | | | | | | |

| | Row | Treatment Protocol | Match % | Average Age | Average Weight (lbs) | No. of sessions treatment protocol used | Overall Feedback of Treatment Protocol |
|---|---|---|---|---|---|---|---|
| Primary Subject Indication | 3A | 110 | 70.0 | 59.1 | 112 | 105 | 87.5 |
| Group To Be Treated: | 3B | 115 | 60.0 | 62.3 | 105 | 108 | 83.4 |
| Parkinson's Disease | 3C | 117 | 60.0 | 62.9 | 104 | 104 | 81.2 |
| Device Type: 4' | 4A | 112 | 60.0 | 59.5 | 112 | 21 | 87.3 |
| | 4B | 114 | 50.0 | 62.7 | 105 | 34 | 82.4 |
| | 4C | 108 | 50.0 | 62.8 | 104 | 55 | 87.2 |

Continuing the example, if no prior subject treatment data is found, but one or more treatment records are found that substantially match treatment for Parkinson's disease in combination with users that are about 55-year old, 125-pound, Asian female, the MR application 134 and/or MR analysis algorithm 138 of the MR system server 132 may generate one or more recommended magnetic resonance treatment protocols with the corresponding device type/model that are most suited for the subject 104 being treated and may transmit the protocol(s) to the client computer 108 of the requesting general practitioner as demonstrated in Table 3. In Table 3, "Record 1B" may be selected as the record that 90% matches this scenario and, thus, a treatment protocol that is substantially the same as shown in "Record 1B" may be recommended if no prior subject treatment data is available.

Another method of generating recommended treatment protocols with corresponding device types/models may include administering a "sweep" of magnetic resonance treatment protocols for that subject's particular primary and/or secondary indication(s). This method is known as a "sweep protocol." As used herein, in a sweep protocol, MR is applied through a range of parameters (e.g., flux density, amplitude, frequency, or other), often keeping other variables constant. The operator 106 may administer a range of magnetic resonance treatment protocols by conducting a "sweep" of treatment protocols using varying parameters with corresponding device types/models, on the subject being treated and then selecting the best treatment protocol in response to the feedback of the subject being treated for that particular illness. In a sweep protocol according to one embodiment, the amplitude may change through a predefined range of values and the frequency may be held constant. In a further embodiment, the amplitude value may be held constant and the frequency may change through a predefined range of values. In yet another embodiment, both the amplitude and frequency may both change through a pre defined range of values. Typically, the values of the treatment protocols are not disclosed to the operator 106. The magnetic resonance treatment protocols administered and the subject feedback is captured and then transmitted and/or stored in the MR database 140 for future treatment sessions.

Subsequently, when the subject returns for future treatments, the operator 106 may administer another "sweep" of magnetic resonance treatment protocols and/or use the MR analysis algorithm 138 and/or MR application 134 to generate recommended magnetic resonance treatment protocols for that subject's particular illness.

In one example, the subject-specific information specifies a 50-year old, 130-pound, Asian male that is seeking treatment for his primary indication, arthritis in the knee. In one embodiment, the operator 106 may administer a series of "sweep" magnetic resonance treatment protocols using varying parameters while the subject is being treated in a 22-inch MR device. The first sweep may include the following parameters at 3 minutes each for the following values: $3.300 \times 10^{-8}$ gauss at 0.92375 Hz, $3.299 \times 10^{-8}$ gauss at 0.92347 Hz, $3.298 \times 10^{-8}$ gauss at 0.92319 Hz, $3.297 \times 10^{-8}$ gauss at 0.92291 Hz. The second sweep may include the following parameters at 2 minutes each for the following values: $3.43 \times 10^{-7}$ gauss at 9.60400 Hz, $3.34 \times 10^{-7}$ gauss at 9.352 Hz, $3.21 \times 10^{-7}$ gauss at 8.988 Hz, $3.03 \times 10^{-7}$ gauss at 8.484 Hz, $2.8 \times 10^{-7}$ gauss at 7.840 Hz, and $2.74 \times 10^{-7}$ gauss at 7.700 Hz. The third sweep may repeat the same steps identified above in the first sweep. In one embodiment, as the operator 106 administers a "sweep" of magnetic resonance treatment protocols, the operator 106 selects the best magnetic resonance treatment protocol in response to the subject's feedback. The selected treatment protocol and subject feedback is transmitted and stored in the MR database 140 for future treatment sessions.

In one example, the subject-specific information specifies a 55-year old, 140-pound, Caucasian male that is seeking treatment for his primary indication, diabetic neuropathy. In one embodiment, the operator 106 may administer a series of "sweep" magnetic resonance treatment protocols using varying parameters while the subject is being treated in a 22-inch MR device. The sweep protocol may include the following parameters at 3 minutes each for the following values: $5.00136 \times 10^{-7}$ gauss at 14.00001 Hz, $5.00135 \times 10^{-7}$ gauss at 13.99998 Hz, $5.00134 \times 10^{-7}$ gauss at 13.99995 Hz, $5.00133 \times 10^{-7}$ gauss at 13.99992 Hz, and $4.9998 \times 10^{-7}$ gauss at 13.997 Hz. As the operator 106 administers a "sweep" of magnetic resonance treatment protocols, the operator 106 selects the best magnetic resonance treatment protocol in response to the subject's feedback. The selected treatment protocol and subject feedback is transmitted and stored in the MR database 140 for future treatment sessions.

In one example, the subject-specific information specifies a 65-year old, 110-pound, Caucasian female that is seeking treatment for her primary indication, headache. In one embodiment, the operator 106 may administer a series of "sweep" magnetic resonance treatment protocols using varying parameters while the subject is being treated in a 7' coil MR device. The first sweep protocol may include the following parameters at 4 minutes each for the following values: Amplitude remains constant at $3.2 \times 10^{-8}$ gauss while frequencies are changed or "swept" from 0.89 Hz to 0.83 Hz over 7 incrementally even steps. The second sweep protocol may include the following parameters at 4 minutes each for the following values: Amplitude is swept from $3.1 \times 10^{-8}$ gauss to $3.2 \times 10^{-8}$ gauss over seven incrementally even steps while frequencies are changed or "swept" from 0.89 Hz to 0.83 Hz over 7 incrementally even steps. As the operator 106 administers a "sweep" of magnetic resonance treatment protocols, the operator 106 selects the best magnetic resonance treatment protocol in response to the subject's feedback. The selected treatment protocol and subject feedback is transmitted and stored in the MR database 140 for future treatment sessions.

Other methods of generating recommended treatment protocols with corresponding device types/models may include artificial intelligence using an intelligent agent to perceive its environment. Method 400 may proceed to step 408.

Step 408: Are Treatment Protocols Available?:

In this decision step, according to one embodiment, if the MR analysis algorithm 138 and/or MR application 134 recommends magnetic resonance treatment protocols generated from positive prior subject treatment records and/or analyzing the information in the MR database 140, then Method 400 may proceed to Step 410. If the MR analysis algorithm 138 and/or MR application 134 cannot generate magnetic resonance treatment protocols based on the information in the MR database 140, then Method 400 to utilize MR system 100 may end.

Step 410: Initializing Magnetic Resonance Device Operational Settings and Applying Magnetic Resonance to Subject According to Selected Treatment Protocol:

In this step, according to one embodiment, the operator 106 reviews one or more recommended MR treatment protocols and selects the MR protocol that best fits the subject being treated. An operator may choose a recommended MR protocol or may choose to select another MR treatment protocol if that has been providing better results for the subject. In one embodiment, the MR device 102 is activated in order to apply magnetic resonance to the subject 104 according to selected treatment protocol. Examples of operational settings include the flux density, frequency, amplitude, intensity, voltage, waveform shape of the electromagnetic energy, and the resonation duration is set according to selected treatment protocol. These determinations may be based upon the size of the MR device 102 (e.g., 7-foot, 4-foot, or 22-inch MR device), the configuration of MR device (e.g., whole body immersion, partial body immersion), and the sequencing of the parameters. It should be noted that in various embodiments, the MR device 102 can range in size from one inch or less to ten feet or more, and these listed sizes are not intended to limit the scope of the invention described herein. The MR device 102 may be activated according to these settings and magnetic resonance is applied. Table 2 demonstrates a subset of MR device data values used as operational settings for the MR device 102 after the operator 106 reviews and selects the MR treatment protocol. These values may not be disclosed to the operator 106. Method 400 may proceed to step 412.

Step 412: Monitoring Subject:

In this step, according to one embodiment, the subject 104 is monitored by, for example, the operator 106 before, during, and/or after a MR session. The monitoring step may take place using subject measurement and feedback data such as, but not limited to, clinical measurements, subject reported outcomes, sensors, recording devices, and/or other methods of clinical observations. In one embodiment, the client computer 108 displays various operational, physiological (sensor), and observational (recording device) data it periodically receives from the magnetometer 212, sensors 204, and/or recording devices 206 via the MR driver 218 as normal operation continues over a period of time. The sensor data may represent a variety of physical parameters including physiological data from subjects being treated with MR, for example, abnormally high blood pressure sensor during MR treatment. The recording device data may represent a variety of observations including symptoms with physical manifestations. In some embodiments, the feedback data includes information provided by the patient before, during, and/or after treatment. Method 400 may proceed to step 414.

Step 414: Are Treatment Adjustments Needed?:

In this decision step, according to one embodiment, the operator 106 examines the results of the recommended magnetic resonance treatment and determines whether the results are satisfactory, e.g., reduced or eliminated symptoms, improved performance, and so on. Alternatively, in response to the subject measurement and feedback data, the operator 106 may be prompted to determine whether changes to the operational or therapeutic parameters are necessary in response to a medically significant event alert. In the event that the subject 104 suffers a medically significant event (i.e. abnormally high heart rate or high blood pressure) during treatment, the client computer 108 may display a medically significant event alert on the display (not shown) of the client computer 108 and may also automatically cease operation of the MR device 102.

Thus, if treatment adjustments are needed, method 400 may return to step 406. In some embodiments, the operator 106 selects from the possible MR treatment protocols generated and the MR device 102 applies the adjusted treatment protocol. Alternatively, the client computer 108 may optionally alter the output of the MR device 102 directly under algorithmic control by recalculating and communicating new electrical waveform parameters to the MR driver 218. See "Records 18-21" in Tables 1a to 1c for an example of a subject (subject ID: D-58) requiring MR treatment protocol adjustments during treatment.

If treatment adjustments are not needed, method 400 may proceed to step 416.

Step 416: Is it Time to End Treatment?:

In this decision step, according to one embodiment, the operator 106 determines whether adjustments of the recommended magnetic resonance treatment protocol have been satisfied in order to end the treatment session. If operator 106 ends treatment, subject data, treatment data, sensor data, and recording device data may be updated and then method 400 may proceed to step 418. If the operator 106 of the client computer 108 does not end treatment, then method 400 may return to steps 412 and 414.

Step 418: Ending MR Treatment:

In this step, according to one embodiment, the operator 106 selects to end the MR treatment. The client computer 108 may then communicate the operational mode to the MR driver 218, and ends the MR treatment session. Method 400 may proceed to step 420.

Step 420: Collecting, Transmitting, and Storing Subject Measurement and Feedback Data to MR System Server for Analysis:

In this step, according to one embodiment, the subject's measurement and feedback data that is associated with the MR session is stored in the treatment data 118 of the local client computer 108. Additionally, the treatment data 118 may be transmitted to the MR system server 132 via the network 130, whereby the treatment data 118 is integrated into the aggregate treatment data 146 and stored in the MR database 140 for analysis of possible future MR treatment protocols for the subject being treated, future subjects, and for future analysis of subject population trends.

The transmission of the treatment data may be done in real time or periodically, for example in batches, daily, weekly, or monthly. In the event the client computer 108 does not have a network connection to the MR system server 132, then the client computer 108 will experience a delay when attempting to transmit the treatment data to the MR system server 132 via the network 130. Once a network connection is established, the client computer 108 may transmit treatment data from the storage device 112 in the client computer 108 to the MR system server 132 via the network 130. Upon receiving the data, it may be extracted and stored in the MR database 140 and the MR system server 132 stores a record of file receipt in the MR database 140 and transmits a copy of the file receipt to the client computer 108 via the network 130. Method 400 may proceed to step 422.

Step 422: Generating Recommended Treatment Protocols for Future Treatments:

In this step, according to one embodiment, by use of the MR analysis algorithm 138 and/or MR application 134, recommended magnetic resonance treatment protocols are generated based on the results from analyzing the subject's clinical measurements and observations, subject reported outcomes, sensor data, recording device and subjective feedback data, and device type/model that is associated with the MR treatment session. Additionally, the MR analysis algorithm 138 may use positive prior subject treatment records, and/or subject specific data from like-situated subjects and subject population trends for that particular illness stored in the MR database 140.

The recommended treatment protocols generated may be stored in the MR database 140 for future treatments. When the same subject returns for future treatments, the MR database 140 may recommend prior subject treatment protocols and/or like-situated treatment protocols stored in the MR database 140.

Once the full spectrum of treatments is completed, method 400 of utilizing MR system 100 may end.

Figure 6:
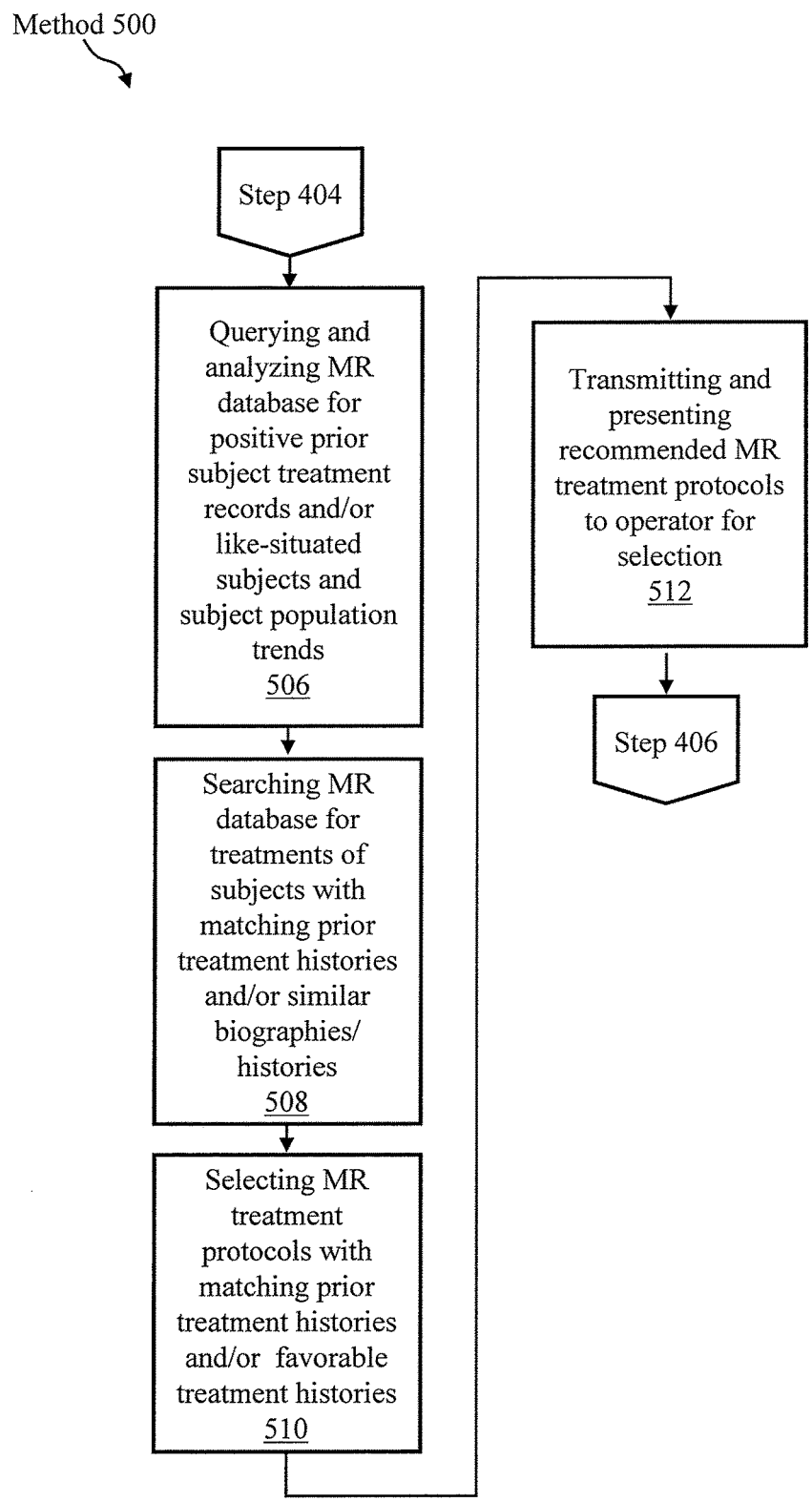
FIG. 6 is a diagram illustrating a method of querying and analyzing a database according to one embodiment of the present invention.

FIG. 6 is a diagram illustrating a method 500 of querying and analyzing a database according to one embodiment of the present invention. In this embodiment, a method 500 may query and analyze a MR database for like-situated subjects and subject population trends for the subject 104. This method describes in more detail steps taken during step 404 in FIG. 5. Method 500 of analyzing data and recommending MR treatment protocols for subjects includes the following steps:

Step 506: Querying and Analyzing Magnetic Resonance Database for Positive Prior Subject Treatment Records and/or Like-Situated Subjects and Subject Population Trends:

In one embodiment, method 404 from FIG. 5 begins with step 506. In this step, the operator 106 may submit a request for magnetic resonance treatment protocols for the primary (and possibly later for the secondary) indication of the subject being treated. The request may be made via the client computer 108 and transmitted and processed at the MR system server 132. Method 500 may proceed to step 508.

Step 508: Searching Magnetic Resonance Database for Treatments of Subjects with Positive Prior Subject Treatment Records and/or Similar Subject Biographies/Histories:

In this step, according to one embodiment, the MR system server 132 processes the request by searching the MR database 140 initially for positive prior subject treatment records and then for like-situated subjects with similar aggregate subject data including device type/model, primary subject indication group (e.g., illness or medical diagnosis), secondary indication group, sex, race, age, weight, recreational habits (e.g., smoker, drug use, alcohol use), and then for aggregate MR treatment data such as the treatment protocol ID number, sensor data, recording device data, and subjective feedback from subject and general practitioner. Method 500 may proceed to step 510.

Step 510: Selecting MR Treatment Protocols with Matching Prior Treatment Histories and/or Favorable Treatment Histories:

In this step, according to one embodiment, once a subset of records of interest are identified, various MR analysis algorithms 138 and mathematical modeling, for example, data mining and trend/statistical analysis (e.g., Bayesian, statistical regression analysis, "best fit" analysis methods, expert systems, artificial intelligence) may determine which record or records completely match or most closely match the circumstance of the subject 104 that is about to receive a treatment via a certain MR device 102. In this way, the MR analysis algorithm 138 may be used to generate and select a recommended magnetic resonance treatment protocols with exactly matching and/or most favorable treatment histories that may be transmitted to the client computer 108 for execution thereof.

Additionally, the MR analysis algorithms 138 may perform deterministic and probabilistic calculations to select possible MR treatment protocols. Deterministic calculations may include algorithms for which a clear correlation is known between the data analyzed and a given outcome. For example, there may be a clear correlation between an indication such as Parkinson's disease, and the data captured by a sensor, such as the rate of tremors measured by a haptics glove sensor. Probabilistic calculations involve the correlation between the data and a given outcome. Probabilistic determinations may require an analysis of several possible outcomes and an assignment of probabilities for those outcomes, as for example, determining possible MR treatment protocols based on the subject data 114 and aggregate subject data 142. As the amount of analyzed aggregate subject data 142 grows, the recommended possible MR treatments may become more accurate based on data patterns and successful treatment outcomes for various illnesses.

In order to identify records of interest, the MR analysis algorithm 138 runs a query against the MR database 140 to identify the records that either match completely or most closely match the subject data 114 of the subject 104 as referred to in Step 422. The query follows a system of steps and then calculates the "match" percentage of the record or records to the subject data 114 of the subject 104.

In one example, a 55-year old, 125-lb Asian female subject with primary indication of Parkinson's disease and multiple secondary indications (arthritis, high BP, and diabetes) ("Subject ID C-37") is being treated for her primary indication and then for her secondary indication(s) with MR treatment. The operator 106 of the client computer 108 may acquire and store Subject ID C-37's subject data 114. The operator 106 may determine the primary indication to be treated and then the secondary indication(s) to be treated. A request for MR treatment protocols to treat the primary indication may be sent by operator 106 to the MR system server 132 via the network 130. The MR system server 132 may process the request by the client computer 108. In order to identify records of interest, the MR analysis algorithm 138 may run a query against records in the MR database 140, searching for positive prior treatment protocols that Subject ID C-37 has received in the past (identifying a complete 100% record match) or for subjects with biographical data and medical histories similar to Subject ID C-37 as shown in records 1-21 as shown in Tables 1a to 1c (identifying a <100% record match).

In one embodiment, to obtain a complete 100% record match, the data from the subject's previous treatments in the identified record must match the subject data 114 and device type/model of Subject ID C-37. In other words, the subject indication group that the subject is suffering from, sex, race, age, weight, and recreational habits from the subject's prior treatments along with the device/type must completely match the subject data 114 of Subject ID C-37. In one embodiment, if the prior treatment data matches the subject data 114 of Subject ID C-37, then a subquery is run against the MR database 140 to retrieve the 100% match record from Subject C-37's prior MR treatment which had an overall positive feedback. The treatment protocol in this record is then presented to the operator 106 of the client computer 108 as a recommended MR treatment protocol. A demonstration of this example is shown as Record 17 in Tables 1a to 1c, where the subject indication group, sex, race, age, weight, recreational habits, and device type/model from Subject ID C-37's prior treatment completely matches the subject data of Subject ID C-37, and Record 17 contains positive feedback to the MR treatment for treatment protocol #116. Therefore, treatment protocol #116 is presented to the operator 106 of the client computer 108 as a recommended MR treatment protocol as shown in Table 3.

In one embodiment, in the event that the MR analysis algorithm 138 is not able to identify a 100% record match to data from the subject's prior treatment, the MR system server 132 defaults, and may run subqueries against the MR database 140 to identify historical records with positive feedback or results which closely match the subject data 114 as referred to in Step 422. The subqueries may run by searching limited portions of matching data (i.e. 90%, 80%, 70% of the aggregate subject and treatment data) against the MR database 140 in order to seek close match historical records with positive feedback. For example, the first subquery may eliminate "race" data as part of its search and run by searching for records that only match 90% of the data such as the subject indication group, sex, age, weight, and recreational habits of the subject being treated for treatment protocols that have received overall positive feedback. If records containing treatment protocols that have received overall positive feedback are found to have a certain degree of matching, an additional subquery is run to rank and qualify those treatment protocols in these records by the number of sessions each treatment protocol was used. The treatment protocol used in the highest number of treatment sessions with overall positive feedback may be qualified as a GOOD match, and the treatment protocol used in the least number of treatment sessions may be qualified as a POOR match.

For example, after running a query for historical records with positive feedback or results, the MR database 140 is unable to identify any BEST matching records, so a subquery is run using 90% of matching data against the MR database 140. This search results in 40 close matched records containing treatment protocols that have received overall positive feedback or results. A subquery is run to rank and qualify the treatment protocols in each of those 40 records to identify the treatment protocol used in the highest number of sessions and the treatment protocol used in the lowest number of sessions. The MR database 140 identifies treatment protocol #102 as a GOOD match where was it used in 42 treatment sessions (the treatment protocol used in the highest number of sessions) and identifies treatment protocol #108 as a POOR match where was used in only 12 treatment sessions. Therefore, treatment protocol #102 may be presented to the operator 106 of the client computer 108 as a recommended MR treatment protocol with a GOOD match.

Additionally, in the case that there are no close matched historical records with positive feedback or results when using 90% of the aggregate subject and treatment data, then, in one embodiment, a subquery is run to look for historical records with positive feedback using 80% of the aggregate subject and treatment data. Thus, "recreational habits" data may be eliminated as part of the search. If the MR database 140 fails to find closely matched historical records with positive feedback with this portion of data, then 70% of the aggregate subject and treatment data is used, eliminating "sensor" data. In the case that there are no closely matched historical records with positive feedback using 70% of the aggregate subject and treatment data, then 60% of the aggregate subject and treatment data is used and a limit is placed on the age using an age range to search the records that are ±5 years from the age of the subject being treated. If no close matched historical records with positive feedback can be located, the subqueries may continue to eliminate other portions of the data such as weight, feedback, and subject indication group. If no close matched historical records with positive feedback can be found, then a new record may be created.

The set of queries and subqueries described above are but one example of many different methods that could be used to find a "best match" and the intent is to provide a thorough example, without limiting the disclosure to this specific implementation. Method 500 may proceed to step 512.

Step 512: Transmitting and presenting recommended MR treatment protocols to operator for selection: In this step, according to one embodiment, one or more recommended MR treatment protocols with positive prior treatment protocols and/or favorable treatment histories determined by the MR analysis algorithms 138 are transmitted and presented to the operator 106 of the client computer 108. This data is shown in Table 3 and may include, for example, the applicable subject indication group(s) that the subject is suffering, the percent that the recommended MR treatment protocol matches the subject data 114 of the subject 104, the average age and weight of like-situated subjects with similar biographies/histories, the number of sessions the recommended MR treatment protocol was used, the overall feedback of the recommended MR treatment protocol, and the device type/model. Additionally, subject specific data of the subject being treated, including the age, weight, subject indication group, prior MR treatment protocol data with feedback, currently administered medications, and initial visual observations made by the operator 106 would be displayed to give the operator 106 the ability to review the recommended MR treatment protocols with respect to the subject's current condition.

For example, a 55 year old Asian female subject with a primary indication of Parkinson's disease and secondary indications of high blood pressure, arthritis, and diabetes ("Subject ID C-37") is being treated first for Parkinson's disease and then for high blood pressure with MR treatment. In one embodiment, a request for MR treatment protocols to treat the primary indication is sent by the operator 106 of the client computer 108 to the MR system server 132 via the network 130. The MR system server 132 may process the request from the client computer 108 by searching the MR database 140 for prior treatment protocols that Subject ID C-37 has received in the past and for subjects with biographical data and medical histories similar to Subject ID C-37 as shown in Tables 1a to 1c, and analyzing this data with the MR analysis algorithms 138 to determine MR treatment protocols. In one embodiment, the operator 106 is presented with recommended MR treatment protocols with matching device type/model as demonstrated in Table 3.

Table 3 shows the data used by the MR system server 132 in one embodiment of the invention to process the request by the client computer 108. In this example, subject C-37's age, race, sex, weight, recreational habits, current medications, subject primary and secondary indication groups from which the subject is suffering, initial observations, prior MR treatment protocols, device type/model, and the primary and secondary indication(s) to be treated is displayed above the recommended treatment protocols. In one embodiment, these data fields are used by the MR system server 132 to search for recommended treatment protocols. In addition to recommending treatment protocols, the MR system server 132 presents the percentage of how close each treatment protocol matches the data fields of the current subject being treated, the average age and weight of subjects who were treated with this recommended treatment protocol, the number of sessions this recommended treatment protocol was used, and the overall percentage of positive feedback when using this recommended treatment protocol.

For example in Table 3, after the MR system server 132 analyzes the data fields of subject C-37 listed above the recommended treatment protocols section and the MR analysis algorithms 138 determines the recommended treatment protocols, the MR system server 132 presents the recommended treatment protocols which best matches subject C-37 for the primary indication she is suffering from, Parkinson's disease. "Record 1A," in the primary indication group: Parkinson's disease for device type/model: 7' in Table 3 shows a record with an exact 100% match, identifying a prior treatment protocol (protocol #116) with positive feedback used by Subject ID C-37. Next, "Record 1B," shows the best closely matched treatment protocol, protocol #102, that MR system server 132 recommends should be used to treat subject C-37. In addition, "Record 1B," provides the percentage of how close protocol #102 matches the data fields of subject C-37 (90.0% match), the average age of subjects who were treated with protocol #102 (59.5 years old), the average weight of subjects who were treated with protocol #102 (126 lbs.), the number of sessions protocol #102 was used (40 times), and the overall percentage of positive feedback when using protocol #102 (98.6% positive feedback). "Records 1C and 1D" provide treatment protocols that may match subject C-37's data fields (for example, protocol #103 has an 80.0% match and protocol #104 has a 70.0% match), but are not the best treatment protocols for treating subject C-37.

In addition, in one embodiment, the MR system server 132 presents the recommended treatment protocols from subjects who suffer from subject indication groups common to subject C-37 in Table 3. For example, in records 2A-4C, the MR system server 132 recommends treatment protocols as well as the percentage of how close each treatment protocol matches the data fields of the current subject being treated, the average age and weight of subjects who were treated with this treatment protocol, the number of sessions this treatment protocol was used, and the overall percentage of positive feedback when using this treatment protocol from subjects suffering from Parkinson's disease as a primary indication. Method 500 may proceed to step 406 in FIG. 5.

Figure 7:
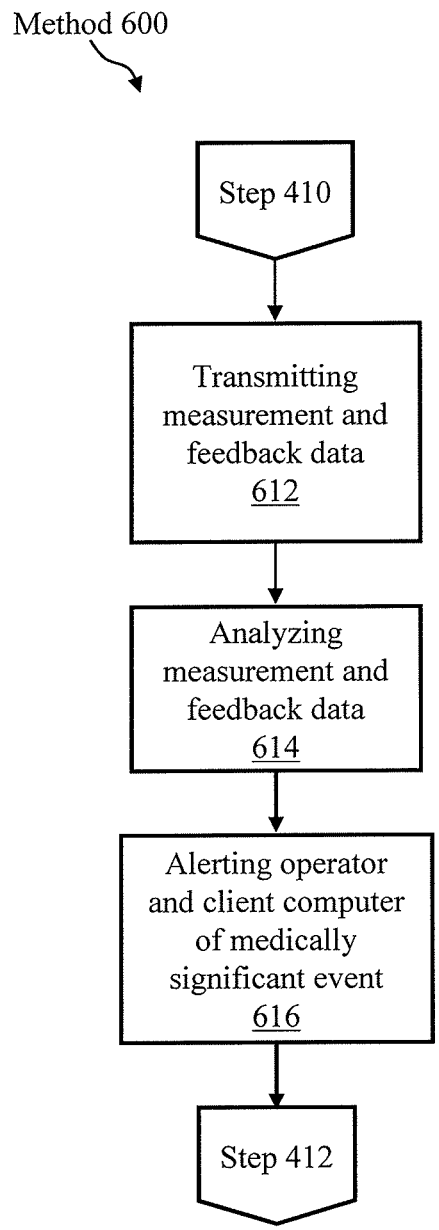
FIG. 7 is a diagram illustrating a method of alerting an operator and client computer of a medically significant event according to one embodiment of the present invention.

FIG. 7 is a diagram illustrating a method of alerting an operator and client computer of a medically significant event according to one embodiment of the present invention. In this embodiment, a method 600 may alert an operator 106 of a client computer 108 of a medically significant event based on subject measurement and feedback data captured during MR treatment. This method describes in more detail steps taken during steps 410-416 in FIG. 5. Method 600 of alerting an operator 106 of a client computer 108 of a medically significant event based on subject measurement and feedback data captured during a MR treatment session includes the following steps:

Step 612: Transmitting subject measurement and feedback data: In this step, the client computer 108 displays various operational, physiological (e.g., sensor), and observational (e.g., clinical measurements, subject reported outcomes, recording device) data it periodically receives from the magnetometer 212, sensors 204, recording devices 206, subject 104, and/or operator 106 via the MR driver 218 as normal operation continues over a period of time during a MR treatment session with a corresponding device type/model for the subject 104. The subject measurement and feedback data is transmitted from the client computer 108 to the MR system server 132 via the network 130. The subject measurement and feedback data may also be acquired from third party networks via third party server 128. Method 600 may proceed to step 614.

Step 614: Analyzing Subject Measurement and Feedback Data:

In this step, according to one embodiment, the MR application 134 in the MR system server 132 processes and analyzes the raw data by comparing the captured data to a fixed range of values. If the captured data exceeds or falls below the fixed range of values, the MR system server 132 may transmit an alert to the client computer 108 via the network 130, advising the client computer 108 that the subject being treated with MR may be experiencing a medically significant event. In one example, a subject is being treated with MR for Parkinson's disease and his blood pressure rises to 145/95 during treatment. This raw data may be captured, for example, by one or more of the sensors 204, such as the Blood Pressure Sensor 204a. The data may be transmitted to the MR driver 218. Subsequently, the MR driver 218 may transmit the data to the client computer 108. In one embodiment, the client computer 108 transmits this data to the MR system server 132 via the network 130. The MR system server 132 may process the raw data and compare the captured blood pressure 145/95 to the fixed range of values for normal blood pressure (less than 120/less than 80), initiating an alert. Method 600 may proceed to step 616.

Step 616: Alerting Operator and Client Computer of Medically Significant Event:

In this step, according to one embodiment, upon recognizing a medically significant event, the MR system server 132 sends an alert to the client computer 108 via the network 130, and advises the client computer 108 that the subject being treated is experiencing a medically significant event. In response to the medically significant event alert, the operator 106 may be prompted by the client computer 108 to determine whether changes to the operational or therapeutic parameters are necessary. Additionally, the client computer 108 may automatically cease operation of the MR device 102. Method 600 of alerting an operator 106 and client computer 108 of a medically significant event based on subject measurement and feedback data captured during MR treatment may proceed through Steps 412, 414, and/or 416 in FIG. 5.

Figure 8:
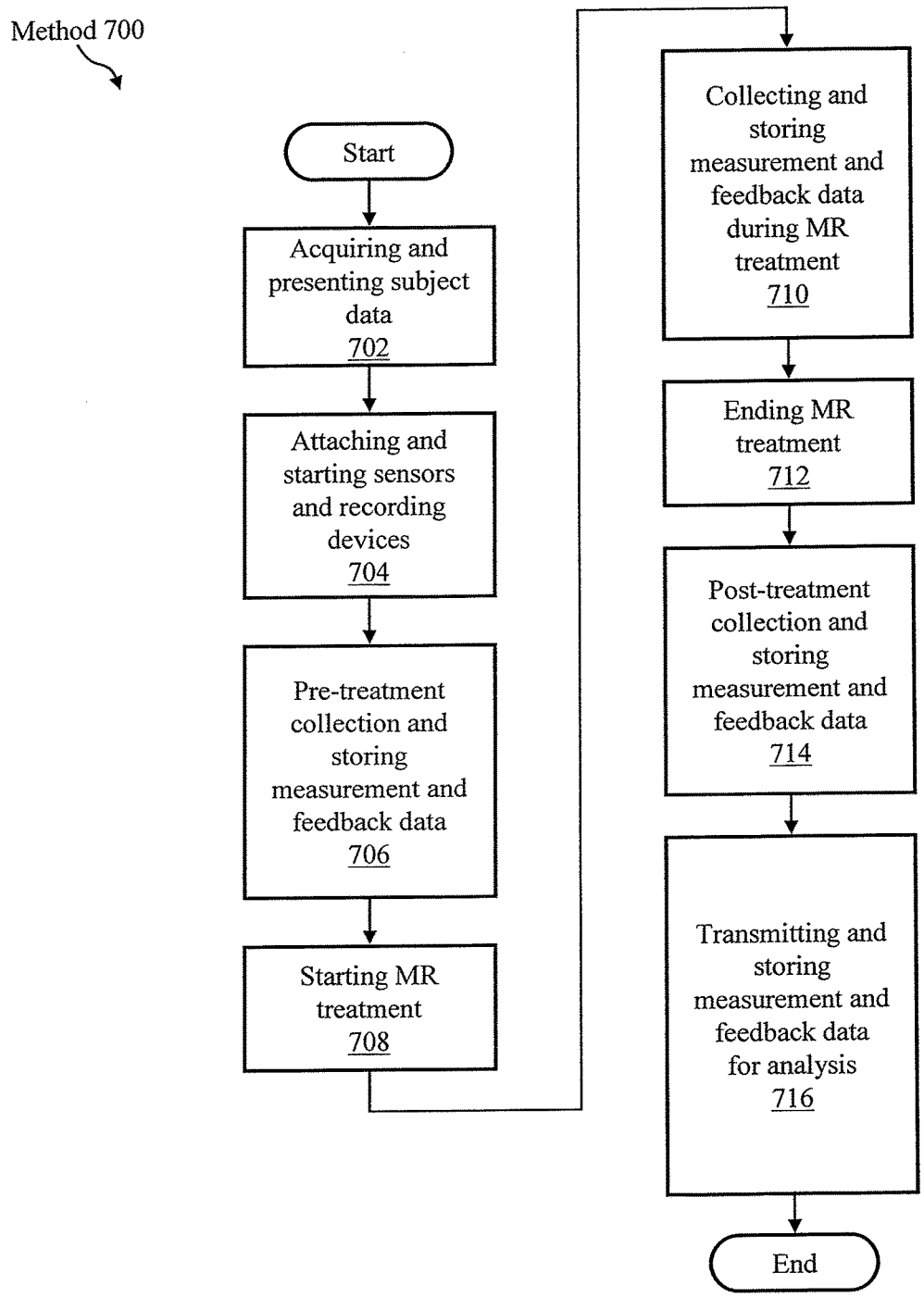
FIG. 8 is a diagram illustrating a method of capturing and storing sensor data according to one embodiment of the present invention.

FIG. 8 is a diagram illustrating a method of capturing and storing sensor data according to one embodiment of the present invention. In this embodiment, a method 700 may capture and store subject measurement and feedback data. Method 700 of capturing and storing subject measurement and feedback data may include the following steps:

Step 702: Acquiring and Presenting Subject Data:

In this step, according to one embodiment, subject data 114 is acquired and presented. For example, the operator 106 may login to the MR application 134 of the MR system server 132 using the MR web application 136. The subject data 114 may be acquired from third party networks via the third party server 128. If the subject 104 has had previous magnetic resonance treatments, the operator 106 may retrieve subject-specific information of the subject 104 from the aggregate subject data 142 and its corresponding device type/model on the MR database 140 of the MR system server 132 via the network 130. Method 700 may proceed to step 704.

Step 704: Attaching and Starting Sensors and Recording Devices:

In this step, according to one embodiment, an operator 106 attaches one or more sensors 204 and recording devices 206 within the magnetic assembly 208. The sensors 204 and recording device 206 may be attached externally or internally to the subject 104 being treated on a platform provided by the coil housing 210 or on the MR device 102 or sensors that are not attached to the subject, such as environmental sensors, may be used. Method 700 may proceed to step 706.

Step 706: Pre-Treatment Collection and Storing Measurement and Feedback Data:

In this step, according to one embodiment, an operator 106 of a client computer 108 collects the sensor and recording device data from one or more sensors 204 and recording devices 206 via the MR driver 218 before the subject 104 receives MR treatment. Additionally, the operator 106 may collect subject reported outcomes and clinical measurements from the subject 104. This data is referred to as the subject's measurement and feedback data (e.g., the sensor and recording device data, the subject reported outcomes, and the clinical measurements). In some embodiments, the subject's measurement and feedback data is then transmitted from the MR driver 218 to the client computer 108 and stored in the treatment data 118 in the storage device 112 on the client computer 108. The subject's measurement and feedback data may also be transmitted and stored on third party networks via the third party server 128. Method 700 may proceed to step 708.

Step 708: Starting MR Treatment:

In this step, according to one embodiment, the client computer 108 applies the MR treatment protocol for the corresponding device type/model selected by the operator 106. The client computer 108 may then communicate the operational mode to the MR driver 218 via one or more cables 216 in the MR device 102, to apply and start the selected MR treatment protocol. Method 700 may proceed to step 710.

Step 710: Collecting and Storing Measurement and Feedback Data During MR Treatment:

In this step, according to one embodiment, during a subject's MR treatment session, the client computer 108 receives data from the one or more sensors 204 and recording devices 206 via the cables 216 by means of the MR driver 218 as previously described. Additionally, the operator 106 may collect subject-reported outcomes and clinical measurements from the subject 104. In one embodiment, the subject's measurement and feedback data is stored as treatment data 118 in the storage device 112 on the client computer 108. The subject's measurement and feedback data may be also be stored on third party networks via the third party server 128. Method 700 may proceed to step 712.

Step 712: Ending MR Treatment:

In this step, according to one embodiment, the display on the client computer 108 prompts the operator 106 to end the MR treatment. The operator 106 of the client computer 108 may select to end the MR treatment session. In one embodiment, the client computer 108 then communicates the operational mode to the MR driver 218 via the cables 216 in the MR device 102, to end the MR treatment protocol. Method 700 may proceed to step 714.

Step 714: Post-Treatment Collection and Storing Measurement and Feedback Data:

In this step, according to one embodiment, the client computer 108 collects data from the one or more sensors 204 and recording devices 206 via the MR driver 218 after the subject receives MR treatment. Additionally, the operator 106 may collect subject reported outcomes and clinical measurements from the subject 104. In one embodiment, the subject's measurement and feedback data is then transmitted from the MR driver 218 to the client computer 108 and stored as treatment data 118 in the storage device 112 on the client computer 108. The subject's measurement and feedback data may also be transmitted and stored on third party networks via the third party server 128. Method 700 may proceed to step 716.

Step 716: Transmitting and Storing Measurement and Feedback Data for Analysis:

In this step, according to one embodiment, the subject's measurement and feedback data stored as treatment data 118 in the client computer 108 from the subject 104 before, during, and/or after the MR treatment session, is transmitted to the MR system server 132 via the network 130. Alternatively, the subject measurement and feedback data may be transmitted from the client computer 108 to the MR system server 132 via the network 130 in "real time" as the sensor and recording device data is collected and transmitted to the client computer 108.

In this step, according to one embodiment, the subject's measurement and feedback data collected from the subject before, during, and/or after the MR treatment is stored in the MR database 140 for analysis of possible MR treatment protocols for the subject being treated, future subjects, and/or for future analysis of subject population trends. The subject's measurement and feedback data may also be transmitted and stored on third party networks via the third party server 128. Method 700 of capturing and storing subject measurement and feedback data may end.

Figure 9:
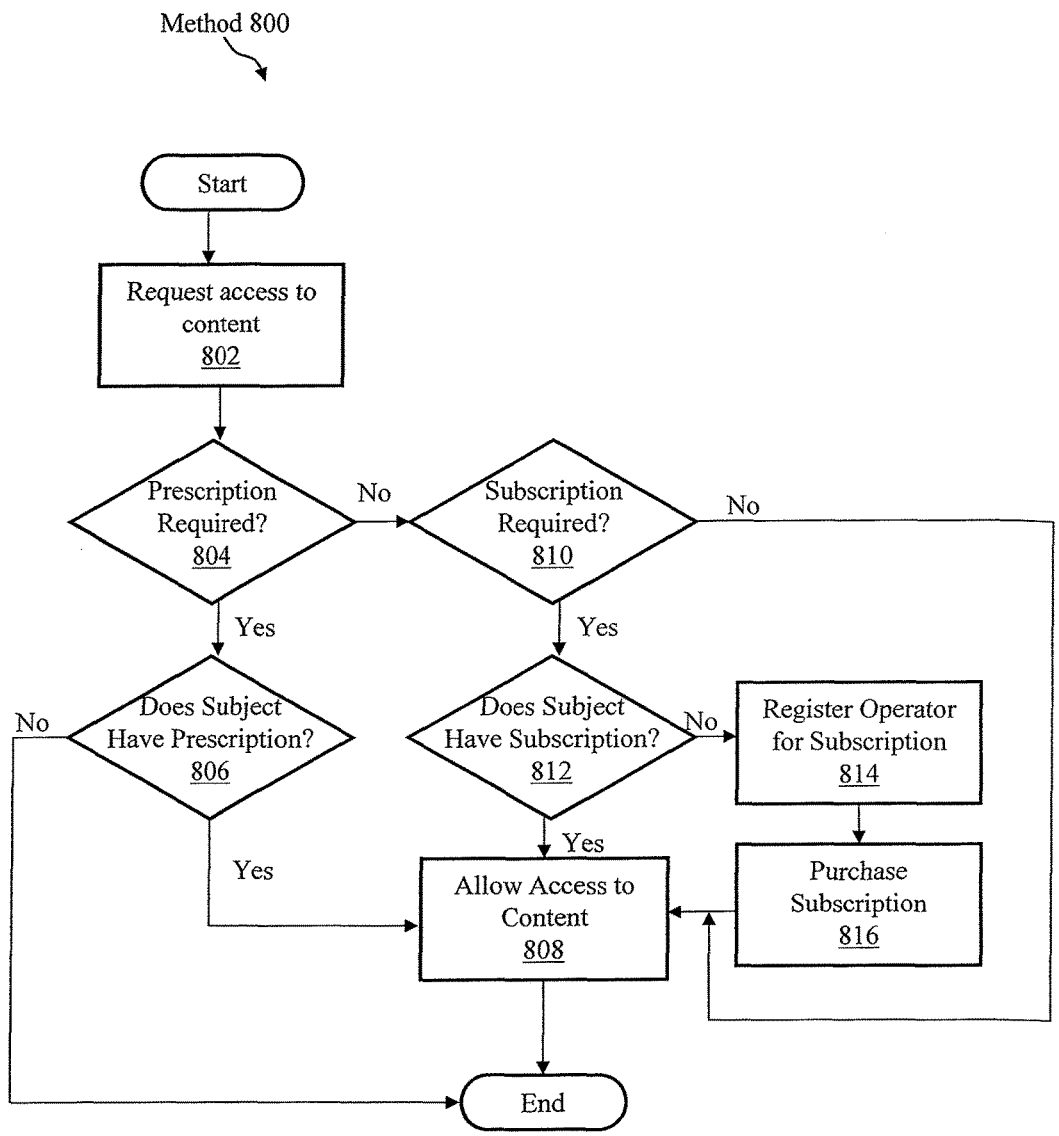
FIG. 9 is a diagram illustrating a method of subscribing to research data or receiving data via a prescription according to one embodiment of the present invention.

FIG. 9 is a diagram illustrating a method of subscribing to research data or receiving data via a prescription according to one embodiment of the present invention. In this embodiment, a method 800 may allow a user to subscribe to research data of one or more MR treatment protocols for specific indications on the MR website hosted by MR system server 132. Further, the method 800 may allow a user to receive data that has been prescribed for him or her. The data of MR treatment protocols may be provided to the MR system server 132 in any of a variety of ways that comport with federal and state privacy laws, such as HIPAA. One way in which data may be provided to the MR system server 132 is by a subject signing a waiver authorizing his or her medical data to be released. Method 800 of subscribing to research and data of MR treatment protocols for specific indications on the MR website hosted by the MR system server 132 includes the following steps:

Step 802: Request Access to Content:

In this step, according to one embodiment, an operator 106 of the client computer 108 or a third party server 128, such as research personnel or third party networks, requests access to content via the network 130 on an MR website hosted by the MR system server 132. Method 800 may proceed to step 804.

Step 804: Can the Requested Content be Viewed by Prescription Holders Only?:

In this step, according to one embodiment, the MR system server 132 determines if the content requested by the client computer 108 is only accessible by prescription holders. If the content is accessible only with a prescription, then the method 800 may proceed to Step 806. If the content is accessible without a prescription, then the method 800 may proceed to Step 810.

Step 806: Does the Operator or Subject have a Prescription for the Requested Content?:

In this step, according to one embodiment, the MR system server 132 determines whether the operator 106 of the client computer 108 or the subject 104 has a prescription to access the requested content. If neither the operator 106 of the client computer 108 nor the subject 104 has a prescription to the requested content, then method 800 may end. If the operator 106 of the client computer 108 or the subject 104 has a current prescription to the requested content, then method 800 may proceed to Step 808.

Step 808: Accessing and Presenting the Requested Content:

In this step, according to one embodiment, an operator 106 of the client computer 108 accesses the requested content. The requested content that is not password-protected and open to the public may be initially presented to the operator 106 of the client computer 108. However, if the requested content requires user name and password because it is under subscription, then the operator 106 of the client computer 108 may enter his user name and password and submit it to the MR system server 132 via the network 130. In one embodiment, the MR system server 132 processes his request, and presents the requested content to the client computer 108 via network 130. Method 800 of subscribing to research and data of MR treatment protocols and/or device types/models for specific indications on the MR website hosted by MR system server 132 ends.

Step 810: Can the Requested Content be Viewed by Subscription Holders Only?:

In this step, according to one embodiment, the MR system server 132 determines if the content requested by the client computer 108 is only accessible by subscription holders. If the content is accessible with a subscription, then the method 800 may proceed to Step 812. If the content is accessible without a subscription, then the method 800 may proceed to Step 808.

Step 812: Does the Operator have Subscription Rights to the Requested Content?:

In this step, according to one embodiment, the MR system server 132 determines whether the operator 106 of the client computer 108 has subscription rights to access the requested content. If the operator 106 of the client computer 108 does not have subscription rights to the requested content, then method 800 may proceed to Step 814. If the operator 106 of the client computer 108 has current subscription rights to the requested content, then method 800 may proceed to Step 808.

Step 814: Registering the Operator for a Subscription:

In this step, according to one embodiment, the operator 106 of the client computer 108 can renew an expired subscription or purchase a new subscription from the MR system server 132. The operator 106 of the client computer 108 may fill out and submits a registration form to the MR system server 132 via the network 130. In some embodiments, the registration form includes one or more of: the name, company or organization name, address, phone number, job title, the indications which interest the operator 106, and other biographical data. The MR system server 132 may store the operator's 106 registration information in the MR database 140. Afterwards, the MR system server 132 presents the client computer 108 with options to purchase various subscriptions to content related to specific indications and/or device types/models. For example, a researcher working for the ABC Foundation for Parkinson's Research, may only want to purchase a subscription to gain access to research and data for MR treatment protocols and corresponding device types/models related to Parkinson's disease. Additionally, organizations such as the National Institute of Health (NIH), one of the world's foremost medical research centers, may want to purchase multiple subscriptions for all types of indications and device types/models to promote research for better MR treatment protocols in those different types of indications. Method 800 may proceed to Step 816.

Step 816: Purchasing a Subscription:

In this step, according to one embodiment, an operator 106 of the client computer 108 selects subscription(s) and submits the selection to the MR system server 132 via the network 130. The MR system server 132 may present the client computer 108 with an agreement between the operator 106 of the client computer 108 and the MR system server 132 including a commitment by the operator 106 of the client computer 108 to purchase the subscription(s) from the MR system server 132 at a specified price and for a fixed duration. In one embodiment, after the operator 106 of the client computer 108 accepts the agreement, the MR system server 132 receives the acceptance from the client computer 108 and processes the request. Then the MR system server 132 presents the client computer 108 with the details of the purchase, including the terms of the subscription, the purchase price, and/or the methods of payment. The operator 106 of the client computer 108 may accept the terms of the subscription, select the method of payment, and submit the payment to the MR system server 132.

In one embodiment, a transaction of funds takes place between the client computer 108 and the MR system server 132 when the MR system server 132 processes the payment for the purchase price which formed the basis of the transaction, and withdraws the purchase price from an account maintained by the operator 106 of the client computer 108 (e.g., credit card account, checking account, or savings account). Afterwards, the MR system server 132 may transmit a confirmation number and activate the operator 106 name and password of the operator 106 of the client computer 108 so that the operator 106 of the client computer 108 can access the content from the purchased subscription. For example, a researcher studying Parkinson's disease may purchase the Parkinson's subscription package for a fixed price and duration. In one embodiment, the researcher pays the purchase price with a credit or debit card and submits the account number, expiration date, and other pertinent information to the MR system server 132 to process his payment. In other embodiments, the purchase price may be paid with any other method of payment, such as a purchase order, check, etc. Next, the MR system server 132 processes the payment and activates the researcher's user name and password so that he can access the content from the recently purchased subscription. Method 800 may proceed to Step 808.

The present invention includes several embodiments. In accordance with one embodiment of the invention, operator 106 updates, verifies, and stores subject-specific information in MR database 140. In this embodiment, the operator 106 inputs or updates subject-specific information for the subject 104 on the client computer 108. After the client computer 108 submits the subject-specific information, the MR application 134 in the MR system server 132 verifies the subject-specific information. If the subject specific information submitted by the client computer 108 does not match the subject-specific information stored in the MR database 140, then the existing subject-specific information may be updated according to rules of the MR application 134 in the MR system server 132.

If a new subject is being treated with MR device 102, an operator 106 of the client computer 108 may input the subject's current subject-specific information. The MR system server 132 can then attempt to verify the subject-specific information submitted by the client computer 108. If the MR system server 132 cannot locate the subject-specific information submitted by the client computer 108, then an alert may be sent to the client computer 108, asking if the subject is new and if a new file should be created for the subject. Upon acceptance by the client computer 108, the MR system server 132 can create a file for the new subject. After the subject-specific information may be verified and updated for a new or existing subject, the subject-specific information is stored in MR database 140 in MR system server 132.

In another embodiment in accordance with the present invention, one or more operators 106 such as research personnel can update or add new treatment protocol data for a corresponding device type/model to the MR system server 132. An operator 106 of the client computer 108 may have authorized access to the aggregate treatment data 146 based on authentication and subscription rights as previously described in Step 810. Based on their access level they may be presented with the subject indication group being treated, and limited treatment session data, such as the identity (type/model) of the MR treatment device, the treatment protocol(s) used during MR treatment, and general subjective feedback provided from the MR treatment.

In one example, an operator 106 such as a clinician, may incorporate the aggregate treatment data 146 into ongoing research for specific or multiple indications or may begin developing new treatment protocols for treating specific primary indication or multiple primary indications as well primary indications in combination with secondary indication(s) for corresponding device types/models. The clinician may be researching Parkinson's disease and may have access to the aggregate treatment data 146 related to Parkinson's disease. He may review the data and incorporate it into his existing case study or trial to continue developing better MR treatment protocols by analyzing test cases and verifying the clinical accuracy of the MR treatment protocol data.

In another example, after reviewing the aggregate treatment data 146 related to Parkinson's disease, a clinician may begin developing MR treatment protocols that treat subjects suffering from Parkinson's disease and other indications, for example, Parkinson's disease and Lou Gehrig's disease. In yet another example, an operator 106 may have subscriptions to all the aggregate treatment data 146 for multiple indications and device types/models, and may decide to begin developing MR treatment protocols for entirely new indications that have yet to be treated with MR treatment. As additional clinically satisfactory MR treatment protocols are added to the MR database 140, the MR system server 132 is able to recommend improved possible MR treatment protocols for all device types/models.

The factors taken into consideration which assess clinically satisfactory MR treatment protocols may include the subject indication group being treated, the device type/model, the MR treatment protocol being used, and/or the degree of testing required to approve the MR treatment protocol. One factor may be the regulatory requirements of the relevant governing authority. For example, in the United States, the subject treatment protocol data may require meeting a more stringent standard, such as Federal Drug Administration (FDA) approval or clinical acceptance when conducting rigorous tests to treat certain indications, such as Parkinson's disease. But other uses, such as some that promote general health, wellness, and well-being may not require FDA approval.

In another embodiment of the present invention, the operator 106 services and updates the MR device 102. During scheduled maintenance periods, an operator 106 of the client computer 108 such as service personnel, requests the MR system server 132 via the network 130 for data/software updates and/or system diagnostics. If data/software updates are available then the MR application 134 in the MR system server 132 processes the request for data/software updates and transmits the updated data and software to the client computer 108 via the network 130 and then downloads the updates on the MR driver 218 via cables 216.

In another example, an operator 106 of the client computer 108 performs system diagnostics and tests the operation of the MR device 102 by sending a request for system diagnostics to the MR driver 218 via one or more cables 216. After the operational tests are completed, the operator 106 reviews the results of the system diagnostics of the MR device 102 and makes necessary adjustments to the components or software of the MR device 102. For example, the operator 106 may adjust the AC Calibration levels (e.g., voltage, current, frequency values) (not shown) or the DC calibration levels (not shown). Upon completion, the service data is transmitted from the MR driver 218 to the client computer 108 and stored in the storage device 112.

In yet another embodiment, the operator 106 services and updates the client computer 108. During scheduled maintenance periods, an operator 106 of the client computer 108 requests the MR system server 132 via the network 130 for data/software updates for the client computer 108. If data/software updates are available, then the MR application 134 in the MR system server 132 processes the request for data/software updates. The MR system server 132 transmits update files to the client computer 108 via the network 130. Upon receipt of the data/software updates, the client computer 108 installs and tests the installation of the update files via the processor 114 in the client computer 108. Afterwards, the client computer 108 stores the record of the update in the storage device 112 in the client computer 108.

In yet another embodiment, an operator 106 of the client computer 108, such as a subject 104, may operate the MR device 102 remotely without the need to interact with an additional operator such as, but not limited to, a general practitioner. For example, a general practitioner may approve a prescription for a recommended magnetic resonance treatment protocol that is generated at the MR system server 132 and prescribe the subject 104 to receive this recommended treatment. The MR device 102 may be a portable or stationary device. The subject will have the flexibility of initiating and receiving this treatment by using the client computer 108 to operate the MR device 102 at his/her convenience.

In another example, a general practitioner may pre-program a portable or stationary MR device 102 with a recommended MR treatment that is generated at the MR system server 132. The subject 104 can operate the pre-programmed MR device 102 and receive the prescribed treatment at his or her convenience.

Magnetic Assemblies According to Various Embodiments

In some embodiments, the magnetic assembly comprises one or more coils. The coils may be arranged in a variety of ways. Some examples are depicted in FIGS. 10a through 10o, and are described herein.

FIGS. 10a through 10o depict magnetic coil assemblies 208a through 208o suitable for use as magnetic assembly 208 in MR device 102 in accordance with various embodiments. For example, some embodiments include various types of coils, which may include modified and/or multi-axis coils. Generally, the subject is positioned between at least two sets of coils to receive MR.

According to some embodiments, each magnetic assembly (e.g., such as those depicted as 208a through 208o) produces a magnetic field proportional to the electric current within it, over a volume sufficient to accommodate a magnetic therapy subject, which may be an entire person, a human limb or other body part, or any living or inanimate object. The scope of the present invention is not limited to the specific embodiments of magnetic assembly 208a through 208o as expressly depicted in FIG. 10a through 10o, but also pertains to any combination of these, any combination of any sub-components of any of these assemblies that produces a magnetic field, or any magnetic assembly or combination of magnetic assemblies known in the art.

In some embodiments, each magnetic assembly 208a through 208o includes a number of magnetic elements. For example, a magnetic assembly may comprise a magnetic coil or plate that produces magnetic flux. In the case of a coil, each coil possesses a single or multiple windings. In one embodiment, the coil comprises a coil consisting of 30-turns of 30-gauge solid-core copper wire (not shown) having a diameter ranging from three inches to twelve feet or more. In the case of a plate, each plate may be constructed of a conductive material, such as copper, or a magnetic material such as ferrite.

However, coils and plates other than those depicted in 208a through 208o, are possible in accordance with the present invention. In various embodiments, the relative orientations of the coils in each magnetic assembly 208a through 208o, described in the following as "parallel" or "perpendicular", is configurable, such that the physical orientation of the coils is adjustable to any relative angle.

In various different embodiments (not shown), each magnetic assembly 208a through 208o is electrically connected to MR driver 218, and optionally wired in parallel with compensation network 214 within MR device 102 of the present invention.

In the embodiment shown in FIG. 10a, the magnetic assembly 208a includes discrete coils 302 and subject support 304. Discrete coils 302 may be further composed of a number of individual coils positioned in a co-axial configuration, at a relative distance from one another that is less than the diameter of the coils, rather than a single continuous spiral. In some embodiments, the subject support 304 is a device, such as a chair, platform or patient bed. The subject support 304 may be constructed of a non-magnetic material. The subject support 304 may be capable of physically supporting a magnetic therapy subject in any position within discrete coils 302. In addition, the subject support 304, may be a tub structure used to submerge the subject in a fluid, such as water, for submersed magnetic therapy. Although not shown in FIG. 10a, subject support may be supported using lateral connections that emerge from the ends of the coil to connect to a stand or other structural component.

Figure 10B:
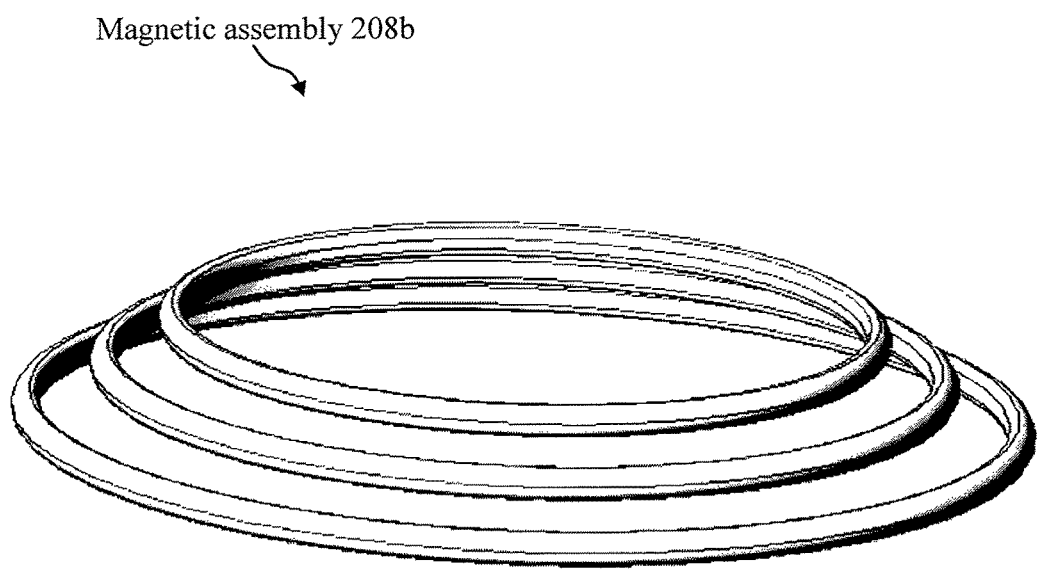
FIGS. 10*a* through 10*o* depict magnetic coil assemblies suitable for use in various embodiments of the present invention.

In the embodiment shown in FIG. 10b, the magnetic assembly 208b includes a plurality of discrete coils 306. The discrete coils 306 are further composed of a number of individual coils. The individual coils may be of different diameters. In some embodiments, the individual coils are positioned in a co-axial configuration, at a relative distance from one another that is smaller than the diameter of the coils. The diameters of individual coils within discrete coils 306 may increase or decrease in a regular along the axis of magnetic assembly 208b.

In the embodiment shown in FIG. 10c, the magnetic assembly 208c includes housing-A 306, housing-B 307, hinged mechanism-A 308, and hinged mechanism-B 309. In one embodiment, the construction of housing-A 306 and housing-B 307 is "D-shaped" such that their flat portions may rest upon a horizontal surface such as a floor surface. In some embodiments, one or more internal "D-shaped" coils (not shown) are enclosed within housing-A 306 and housing-B 307. Additionally, housing-A 306 and housing-B 307 may be segmented, at least once, with a hinged mechanism 308 so that they may be folded one or more times to ease handling for storage, re-positioning or shipment.

Figure 10D:
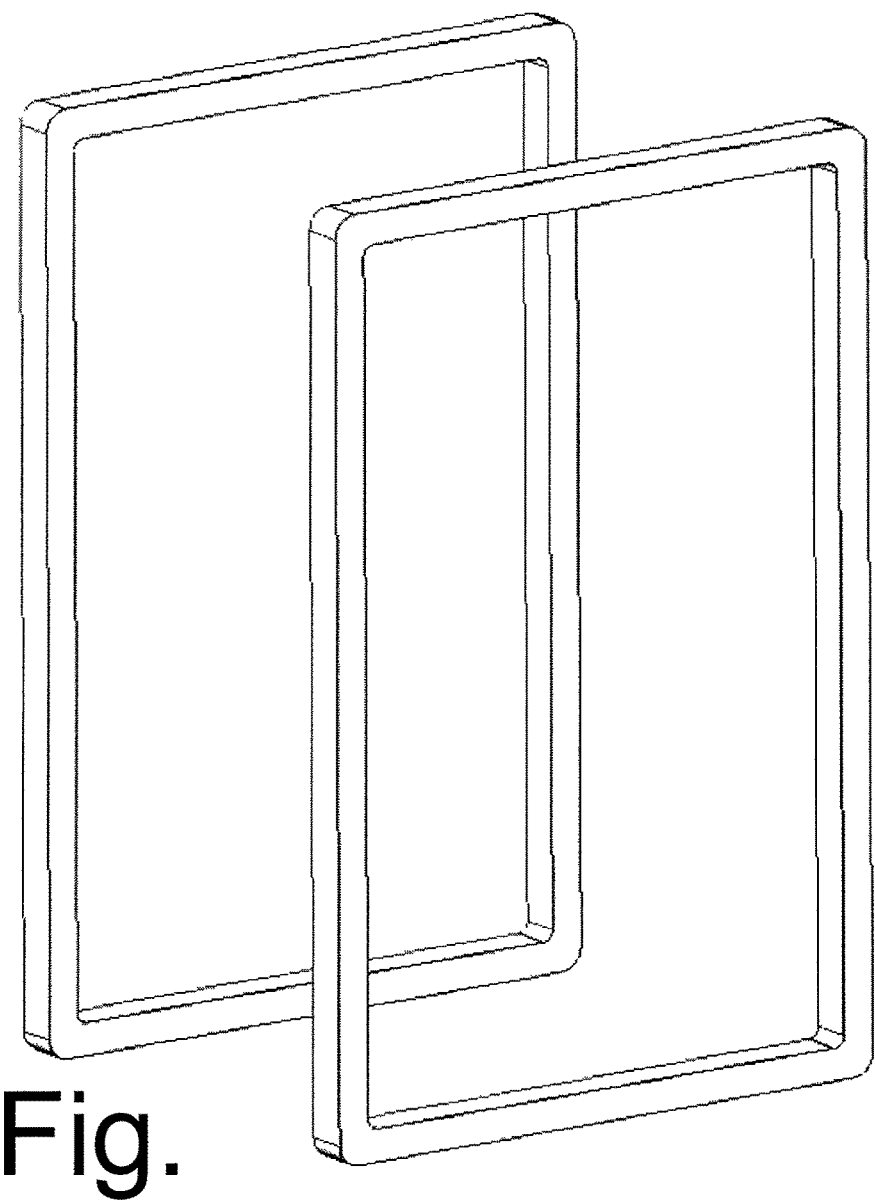

In the embodiment shown in FIG. 10d, the magnetic assembly 208d includes paired individual coils of a non-circular shape. The magnetic assembly 208d may be of any non-circular shape including a rectangular shape as shown in FIG. 10d.

Figure 10E:
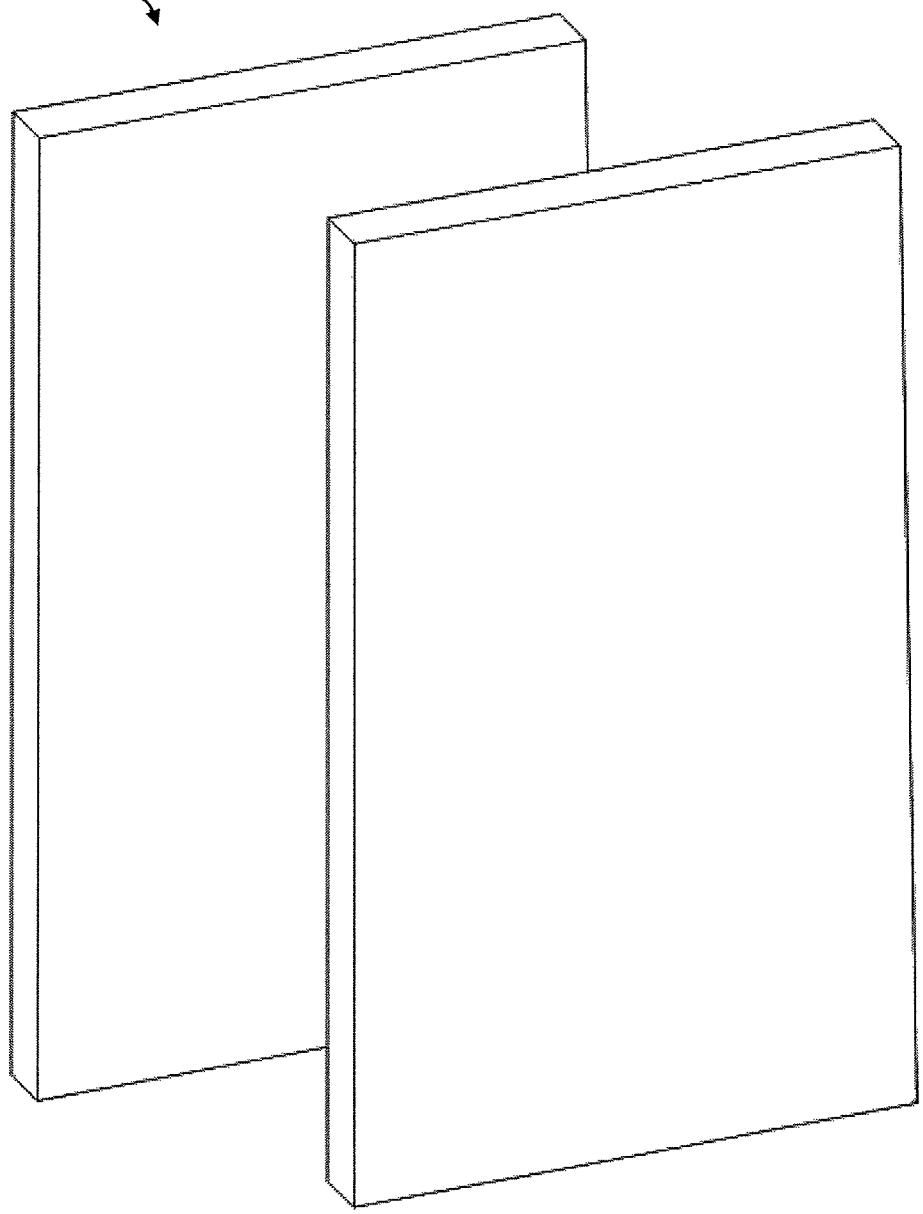

In the embodiment shown in FIG. 10e, the magnetic assembly 208e includes paired plates which produce magnetic flux. The plates of magnetic assembly 208e may optionally contain slots, perforations, punctures or other voids of any size, shape or pattern, i.e. regularly or random randomly placed throughout the plate (not shown).

Figure 10F:
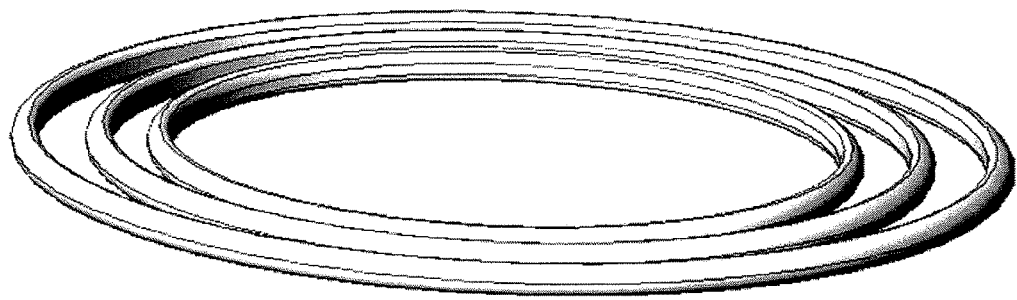
Figure 10F:
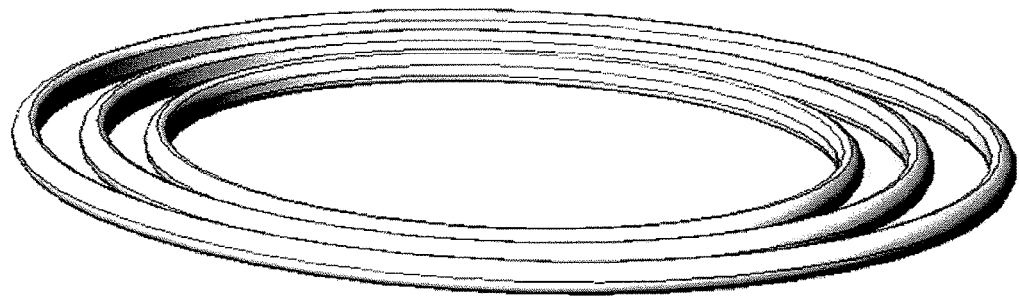

In the embodiment shown in FIG. 10f, the magnetic assembly 208f depicts a set of at least four individual coils that are arranged in an overall coaxial configuration. In one embodiment, the coaxial coils of magnetic assembly 208f are further subdivided into at least two sub-groups of two individual coils which are concentric and co-planar, and in addition, possess differing diameters. The spacing between individual coils within each set of coils of magnetic assembly 208f may be spaced in a variety of ways, for example, evenly spaced, regularly spaced, or randomly spaced apart. Regularly spaced coils may include, for example, coils whose spacing increases at a constant rate of displacement, or alternatively at an exponential rate.

Figure 10G:
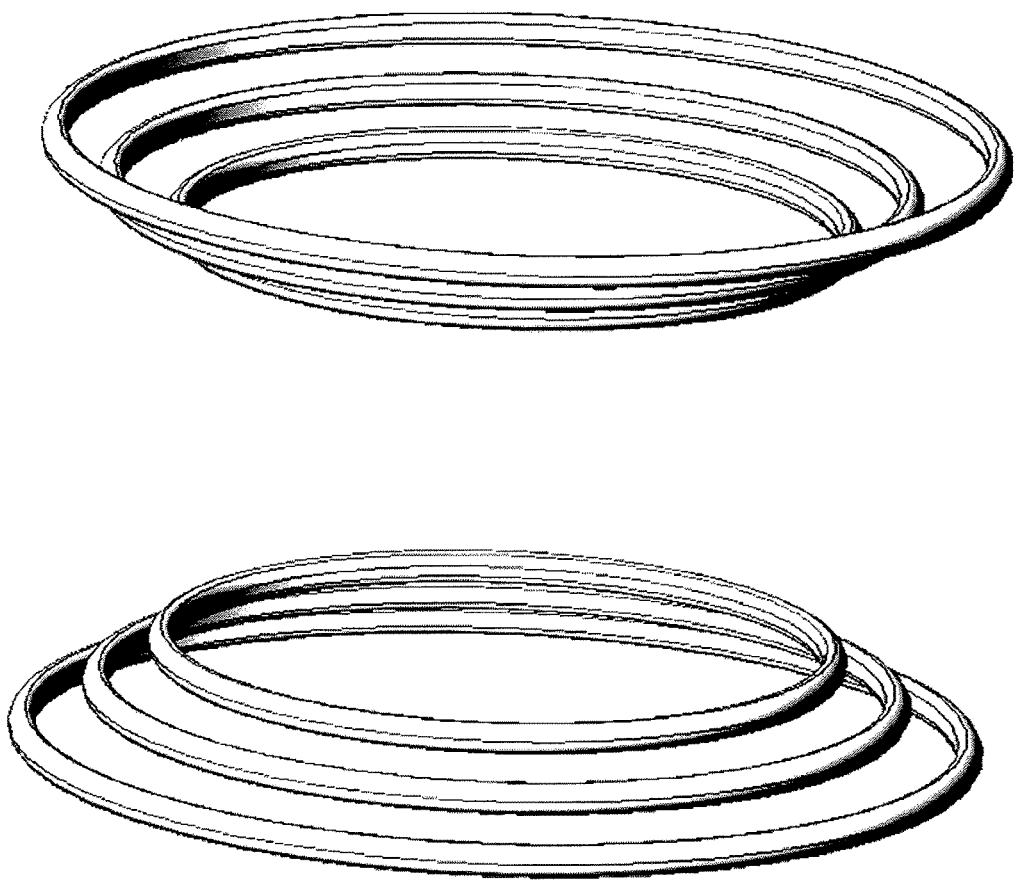

In the embodiment shown in FIG. 10g, the magnetic assembly 208g depicts a set of at least four individual coils that are arranged in an overall coaxial configuration. In one embodiment, the coaxial coils of magnetic assembly 208f are further subdivided into at least two sub-groups of coils. Individual coils within each sub-group may be spaced at a relative distance that is less than the diameter of the smallest individual coils, while groups of coils are spaced further apart, as shown in FIG. 10g. The order of individual coils may vary by size, for example the smallest coil may be the innermost coil, or the outmost coil (or in any other position) in magnetic assembly 208g.

Figure 10H:
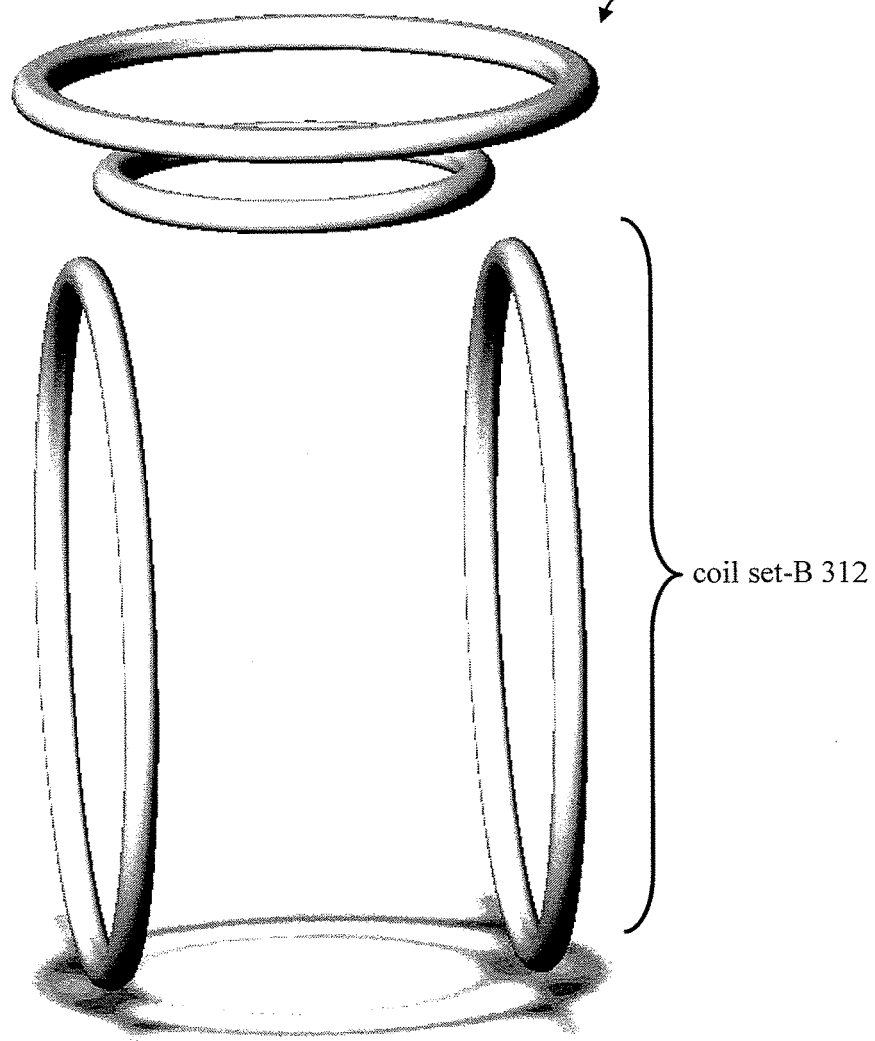

In the embodiment shown in FIG. 10h, the magnetic assembly 208h includes two sets of two coaxial coils, coil set-A 310 and coil set-B 312. In one embodiment, the axes of coil set-A 310 and coil set-B 312 are perpendicular to one another and lie on a common plane. In some embodiments, the axis of coil set-A 310 intersects the midpoint between the coils of coil set-B 312, while the axis of coil set-B 312 lies outside the midpoint between the coils of coil set-A 310, as shown in FIG. 10h. The subject may be positioned in the center of the assembly.

Figure 10I:
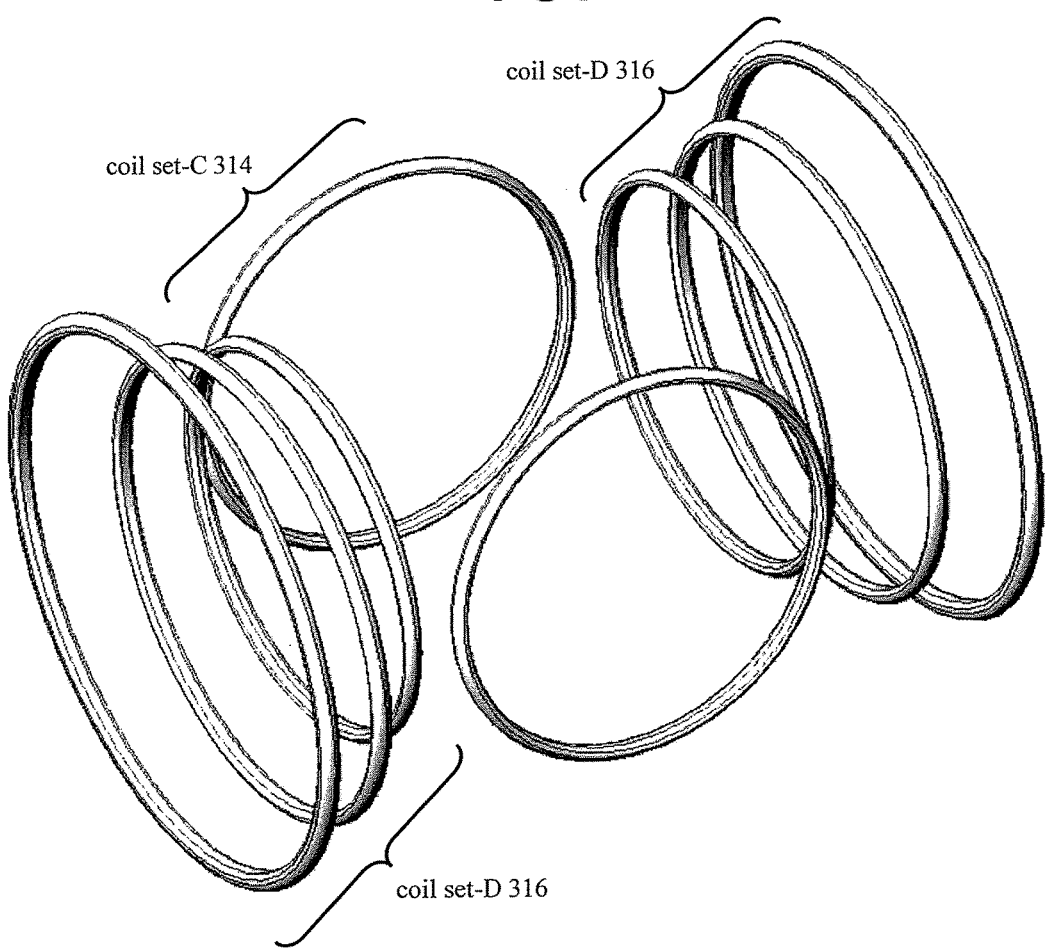

In the embodiment shown in FIG. 10i, the magnetic assembly 208i includes two sets of coaxial coils, coil set-C 314 and coil set-D 316. In one embodiment, coil set-C 314 is a pair of opposing single coils, while coil set-D 316 is a pair of opposing triple coils, six coils total. In some embodiments, the axes of coil set-C 314 and coil set-D 316 are perpendicular to one another and lie on a common plane. The axis of coil set-C 314 and coil set-D 316 may intersect at a common midpoint as shown in FIG. 10i. The subject may be positioned in the center of the assembly.

In the embodiment shown in FIG. 10j, the magnetic assembly 208j includes three sets of orthogonal coil pairs, coil set-E 318, coil set-F 320, and coil set-G 322. The axis of coil set-E 318, coil set-F 320, and coil set-G 322 may intersect at a common midpoint as shown in FIG. 10j. The subject may be positioned in the center of the assembly.

In the embodiment shown in FIG. 10k, the magnetic assembly 208k includes three sets of orthogonal coil pairs, coil set-H 324, coil set-I 326, and coil set-J 328. The axis of coil set-H 324, coil set-I 326, and coil set-J 328 may intersect at a common midpoint as shown in FIG. 10k. Coil set-I 326 may include two sets of coaxially placed coils; each set may comprise two or more parallel coils. The subject may be positioned in the center of the assembly.

In the embodiment shown in FIG. 10L, the magnetic assembly 208l includes discrete coils 330 and subject support 332, coil set-K 334 and coil set-L 336. In one embodiment, discrete coils 330 are further composed of a number of individual coils positioned in a co-axial configuration. In some embodiments, subject support 332 is a device, such as a chair, platform, patient bed and/or tub filled with a fluid (such as water), constructed of a non-magnetic material, and capable of physically supporting a magnetic therapy subject in any position within discrete coils 330. Coil set-K 334 and coil set-L 336 may be two sets of single coaxial coils. The axes of coil set-K 334 and coil set-L 336 may be perpendicular to one another and lie on a common plane. In one embodiment, the axis of discrete coils 330, coil set-K 334, and coil set-L 336 are orthogonal and intersect at a common midpoint as shown in FIG. 10L. The subject may be positioned in the center of the assembly.

Figure 10M:
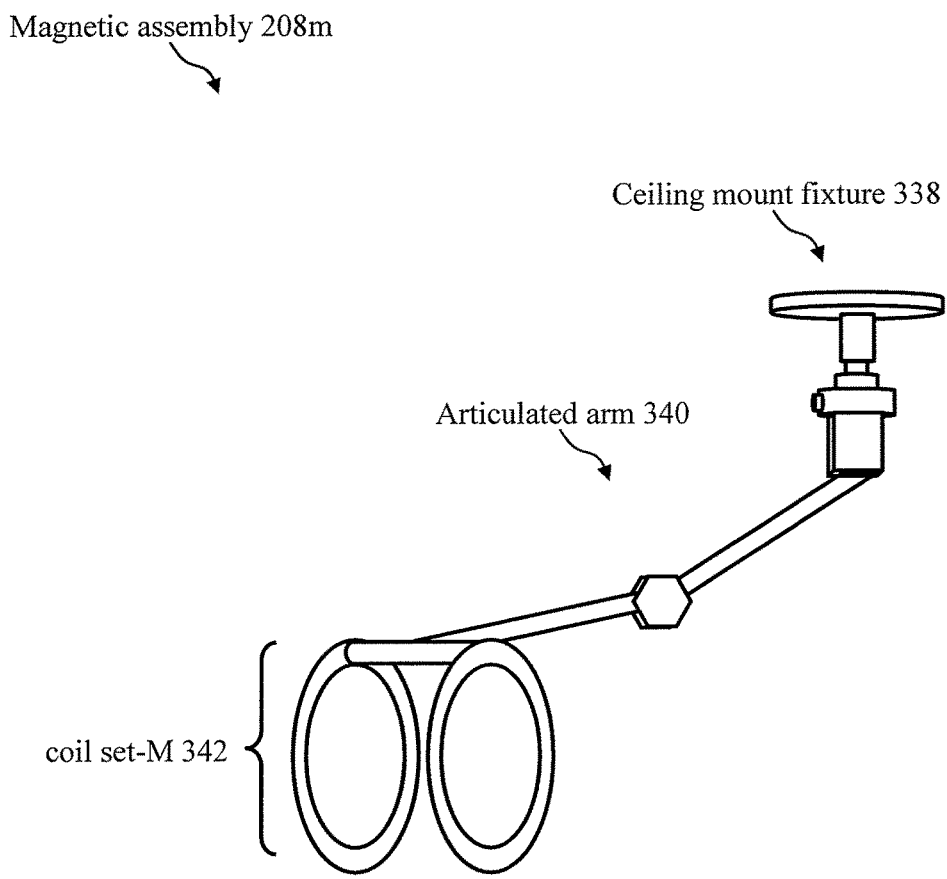

In the embodiment shown in FIG. 10m, the magnetic assembly 208m includes ceiling mount fixture 338, articulated arm 340 and coil set-M 342. In one embodiment, the magnetic assembly 208m is an articulated positioning device, as shown in FIG. 10m, in which ceiling mount fixture 338 provides fixture to any surface, such as a floor, ceiling or wall. The articulated arm 340 may provide a free range of motion such that coil set-M 342 may be positioned in any number of positions and orientations. Although shown with single circular coils, this type of assembly can be used with any of the coils of the present invention.

Figure 10N:
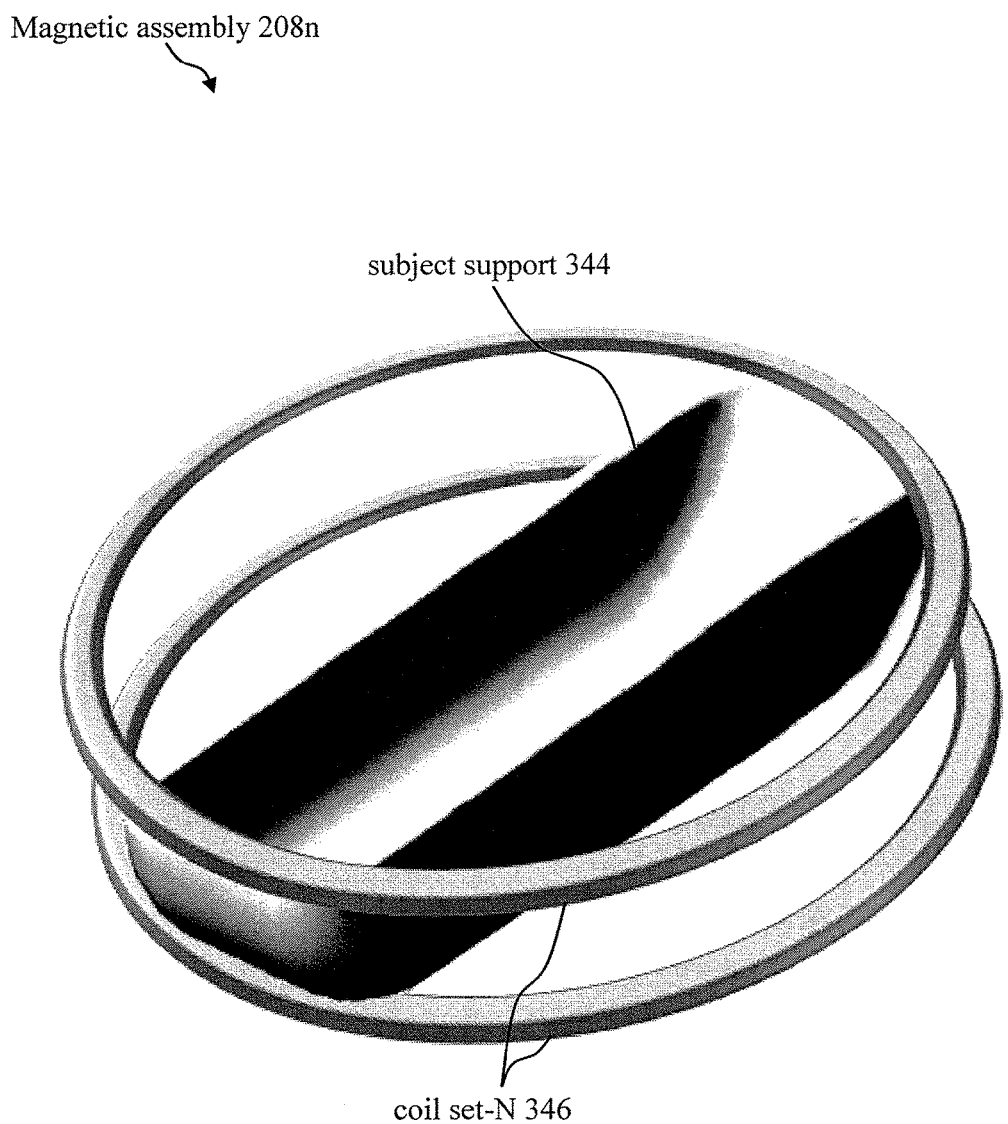
Figure 10O:
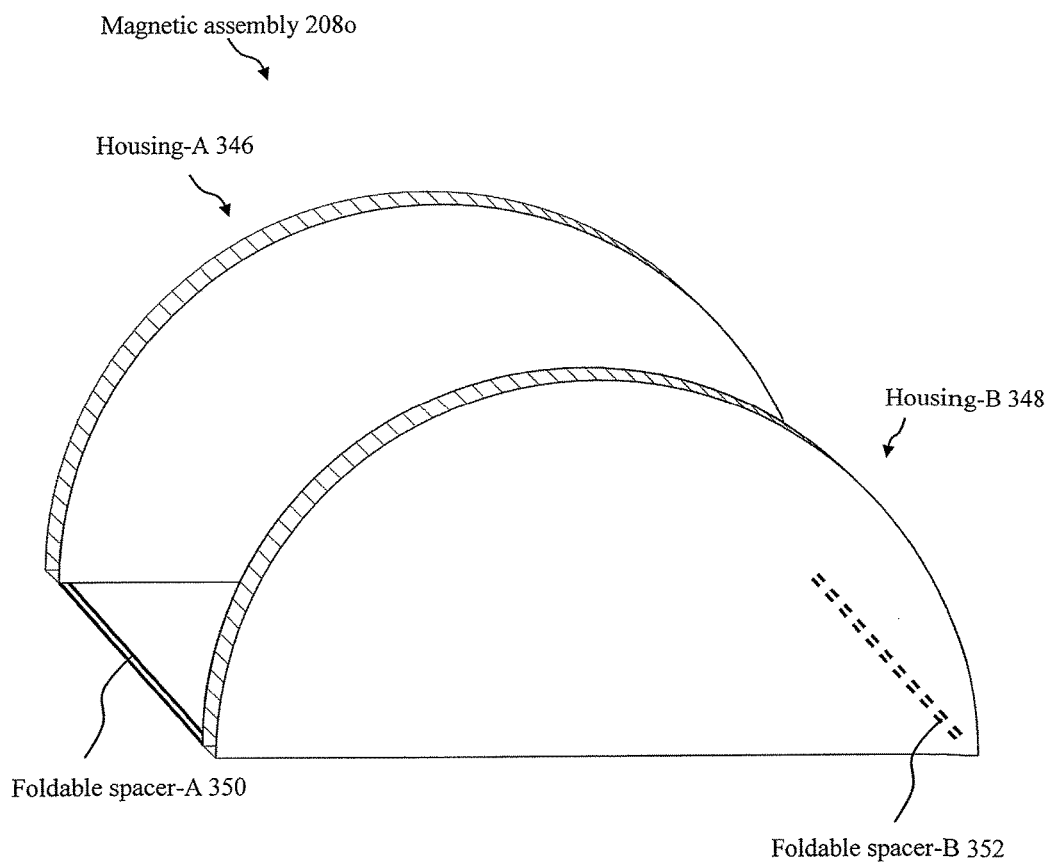

In the embodiment shown in FIG. 10n, the magnetic assembly 208n includes subject support 344, and coil set-N 346. In one embodiment, coil set-N 346 comprises one or more sets of horizontally oriented coaxial coils. In some embodiments, subject support 344 is a device, such as a chair, platform, patient bed and/or tub filled with a fluid (such as water), constructed of a non-magnetic material, and capable of physically supporting a magnetic therapy subject in any position within the axis of coil set-N 346 as shown in FIG. 10n.

In the embodiment shown in FIG. 10o, the magnetic assembly 208o includes housing-C 346, housing-D 348, foldable spacer-A 350, and foldable spacer-B 352. In some embodiments, the construction of housing-C 346 and housing-D 348 is "D-shaped" such that their flat portions may rest upon a horizontal surface such as a floor surface. Internal "D-shaped" coils (not shown) may be enclosed within housing-C 346 and housing-D 348. In some embodiments, housing-C 346 and housing-D 348 are connected via two hinged spacers, foldable spacer-A 350 and foldable spacer-B 352, that are hinged at all four connection points (not shown) to housing-C 346 to housing-D 348. These hinged connections allow magnetic assembly 208o to be folded flat for storage, re-positioning or shipment.

Referring to FIGS. 10a through 10o, as well as FIG. 2, the operation of magnetic assemblies 208a through 208o according to some embodiments may be summarized as follows. In operation, the client computer 108 may communicate operational commands, such as normal operation on/off, AC calibration, and DC calibration to the MR driver 218. For normal operation according to one embodiment, the client computer 108 further communicates specific magnetic waveform parameters, such as waveform type (e.g., sinusoidal, rectilinear, square), amplitude (e.g., 1 milli-volt) and frequency (e.g., 10 Hz) to MR driver 218. The MR driver 218 may provide the specific waveform to magnetic assembly 208. The magnetic assembly 208 may be connected in parallel with the compensation network 214, for example wired via cables 216. In some embodiments, the internal coil configuration of the magnetic assembly 208 is one or more of magnetic assemblies 208a through 208o. The individual coils and/or plates of each magnetic assemblies 208a through 208o may be energized in any order, by any waveform, continuous or discontinuous.

From the foregoing, one of ordinary skill in the art will appreciate that the present disclosure sets forth a system for providing MR with a plurality of MR devices and a method of using a MR system with a plurality of MR devices. The teachings of this disclosure shall not be considered to be limited to the specific examples disclosed herein, but to include all applications within the spirit and scope of the invention.

We claim:

1. A method of providing a magnetic resonance treatment to a subject, comprising:
    querying a database of a plurality of magnetic resonance treatment protocols and parameters;
    generating a magnetic resonance treatment protocol based at least in part on a result of the query;
    providing a first magnetic resonance treatment to the subject using a magnetic resonance device comprising a magnetic assembly;
    controlling, by a magnetic resonance driver, the magnetic resonance device according to the magnetic resonance treatment protocol, wherein the magnetic resonance driver comprises an electronic waveform generator;
    compensating using a compensation network comprising a resistor and capacitor network configured to match an impedance of the magnetic resonance driver, wherein the magnetic assembly is coupled in parallel with the compensation network;
    determining a magnetic field strength output by the magnetic resonance device; and
    modifying the magnetic resonance treatment based in part on a biometric measurement and the determined magnetic field strength.

2. The method of claim 1, wherein the biometric measurement comprises a measurement received from one or more of:
    a blood pressure sensor;
    a perspiration sensor;
    a body weight sensor;
    a body temperature sensor;
    a haptics glove sensor;
    an electroencephalograph; or
    an electrocardiograph.

3. The method of claim 1, wherein querying the database comprises at least one of:
    searching the database for prior treatment data of the subject;
    searching the database for a treatment of a like-situated subject with a medical history similar to the subject; or
    searching the database for a subject population trend.

4. The method of claim 1, wherein modifying the magnetic resonance treatment comprises applying a second magnetic resonance treatment to the subject at a different magnetic field strength than the first magnetic resonance treatment.

5. The method of claim 4, wherein modifying the magnetic resonance treatment further comprises:
    monitoring the subject during the treatment;
    providing subject data to a processor; and
    determining whether a treatment adjustment is needed, and if it is determined that the treatment adjustment is needed, identifying the needed adjustment.

6. The method of claim 5, wherein determining whether a treatment adjustment is needed comprises comparing an intended result of the treatment to an actual result of the treatment.

7. The method of claim 1, further comprising ending treatment, wherein ending the treatment of the subject comprises:
    commanding a processor to end the treatment;
    using a processor to collect and store subject data; and
    providing the subject data to a database.

8. The method of claim 1, further comprising obtaining access to the magnetic resonance treatment protocol.

9. The method of claim 8, wherein obtaining access to the magnetic resonance treatment protocol comprises determining whether an operator has a subscription to the magnetic resonance treatment protocol.

10. The method of claim 1, further comprising:
    executing a sweep protocol; and
    generating the magnetic resonance treatment protocol based at least in part based on a result of the subject's feedback during the sweep protocol.

11. A system for providing a magnetic resonance to a subject, the system comprising:
    a processor configured to:
        query a database of a plurality of magnetic resonance treatment protocols and parameters;
        generate a magnetic resonance treatment protocol based at least in part on a result of the query;
        provide a first magnetic resonance treatment to the subject using a magnetic resonance device comprising a magnetic assembly;
        control a magnetic resonance driver to control the magnetic resonance device according to the magnetic resonance treatment protocol, wherein the magnetic resonance driver comprises an electronic waveform generator;

determine a magnetic field strength output by the magnetic resonance device; and modify the magnetic resonance treatment based in part on a biometric measurement and the determined magnetic field strength; and a compensation network comprising a resistor and capacitor network configured to match an impedance of an magnetic resonance driver, wherein the magnetic assembly is coupled in parallel with the compensation network.

12. The system of claim 11, wherein the biometric measurement comprises a measurement received from one or more of:

a blood pressure sensor;
a perspiration sensor;
a body weight sensor;
a body temperature sensor;
a haptics glove sensor;
an electroencephalograph; or
an electrocardiograph.

13. The system of claim 11, wherein querying the database comprises at least one of:

searching the database for prior treatment data of the subject;
searching the database for a treatment of a like-situated subject with a medical history similar to the subject; or
searching the database for a subject population trend.

14. The system of claim 11, wherein modifying the magnetic resonance treatment comprises applying a second magnetic resonance treatment to the subject at a different magnetic field strength than the first magnetic resonance treatment.

15. The system of claim 14, wherein modifying the magnetic resonance treatment further comprises:

monitoring the subject during the treatment;
providing subject data to a processor; and
determining whether a treatment adjustment is needed, and if it is determined that the treatment adjustment is needed, identifying the needed adjustment.

16. The system of claim 15, wherein determining whether a treatment adjustment is needed comprises comparing an intended result of the treatment to an actual result of the treatment.

17. The system of claim 11, wherein the processor is further configured to end treatment, wherein ending treatment comprises:

ending magnetic resonance treatment;
collecting and storing subject data; and
providing the subject data to a database.

18. The system of claim 11, wherein the processor is further configured to obtain access to the magnetic resonance treatment protocol.

19. The system of claim 18, wherein obtaining access to the magnetic resonance treatment protocol comprises determining whether an operator has a subscription to the magnetic resonance treatment protocol.

20. The system of claim 11, wherein the processor is further configured to:

execute a sweep protocol; and
generate the magnetic resonance treatment protocol based at least in part based on a result of the subject's feedback during the sweep protocol.

* * * * *